United States Patent [19]

Coughlin et al.

[11] Patent Number: 5,688,768
[45] Date of Patent: Nov. 18, 1997

[54] RECOMBINANT THROMBIN RECEPTOR AND RELATED PHARMACEUTICALS

[75] Inventors: Shaun R. Coughlin, San Francisco; Robert M. Scarborough, Belmont, both of Calif.

[73] Assignee: COR Therapeutics, Inc., South San Francisco, Calif.

[21] Appl. No.: 789,184

[22] Filed: Nov. 7, 1991

Related U.S. Application Data

[63] Continuation-in-part of Ser. No. 657,769, Feb. 19, 1991, Pat. No. 5,256,766.

[51] Int. Cl.[6] .................. A61K 36/00; C07K 7/06; C07K 7/08; C07K 7/10
[52] U.S. Cl. .................. 514/15; 530/327; 530/328; 530/329; 530/330; 530/331; 514/14; 514/15; 514/16; 514/17; 514/18
[58] Field of Search .................. 530/327, 328, 530/330, 331; 514/14–18

[56] References Cited

U.S. PATENT DOCUMENTS

| | | | |
|---|---|---|---|
| 4,783,330 | 11/1988 | Furie | 424/1.1 |
| 4,859,609 | 8/1989 | Dull et al. | |
| 5,256,766 | 10/1993 | Coughlin | 530/327 |

FOREIGN PATENT DOCUMENTS

| | | |
|---|---|---|
| 0 205 270 | 12/1986 | European Pat. Off. |
| 0 272 703 | 6/1988 | European Pat. Off. |
| 0272703 | 6/1988 | European Pat. Off. |

OTHER PUBLICATIONS

Vu et al, Nature, vol. 353, 674–677 (1991).
Edgington, Biotechnology, 1992, vol. 10. pp. 383–386, 388–389.
Khai et al, Nature, 1991, vol. 353, pp. 674–677.
Scarborough, et al, J. Biol. Chem, vol. 267, No. 15, 1992 pp. 13146–13149.
Hui et al, Biochemical and Biophysical Research Communication, vol. 184. No. 2, 1992, pp. 790–796.
Masu et al., Nature (1987) 329836–838.
Ruda et al., Biochemical Pharmacology (1990) 39(2):373–381.
Ruda et al., Annals New York Academy of Sciences (1986) 485:439–442.
Walz et al., Annals New York Academy of Sciences (1986)485:323–334.
Bar–Shavit et al., Journal of Cell Biology (1991) 112(2):335–344.
Vu et al., Domains Specifying Thrombin–Receptor Interaction; Nature 353:674–677 (1991).
Ruda et al., Identification of Small Peptide Analogues Having Agonist and Antagonist Activity at the Platelet Thrombin Receptor; Biochem. Pharmacol. 37(12):2417–2426.

Baniyash et al., J. Biol. Chem., vol. 264, pp. 13252–13257 (1989).
D. Cosman, DNA and Protein Engeneering Techniques, vol. 2, No. 1, pp. 1–3 (1990).
Foster et al., id., vol. 82, pp. 4673–4677 (1985).
Frost et al., J. Cell. Biol., vol. 105, pp. 2551–2558 (1987).
Gearing et al., EMBO Journal, vol. 8, pp. 3667–3676 (1989).
Jackman et al., Proc. Natl. Acad. Sci., vol. 84, pp. 6425–6429 (1987).
Rasmussen et al.,FEBS Letters, vol. 288, pp. 123–128 (1991).
Seed et al., id., vol. 84, pp. 3365–3369 (1987).
Sevier, Clin. Chem., vol. 27, pp. 1797–1806 (1981).
Suzuki, Acta Haematol., vol. 51, pp. 1655–1664 (1988).
Yamamoto et al., Thrombosis and Haemostasis, vol. 55(2), pp. 162–167 (1986).
Young et al., Proc. Natl. Acad. Sci. USA, vol. 80, pp. 1194–1198 (1983).
Vu et al., Molecular Cloning of a Functional Thrombin Receptor Reveals a Novel Proteolytic Mechanism of Receptor Activation; Cell 64:1057–1058.
Gronke et al., J. Biol. Chem. (1987) 262(7):3030–3036.
Okamura et al., J. Biol. Chem. (1978) 253(10):3435–3443.
Berndt et al., "Platelets in Biology and Pathology" (1981)J.T. Dingle et al., Eds. Elsevier/North Holland Biomedical Press, vol. 5, pp. 43–74.
Martin et al., Biochem. (1975) 14(6):1308–1314.
Tollefsen et al., J. Biol. Chem. (1974) 249(8):2646–2651.
Phillips, Thrombin Diath. haemorrh. (1974) 32:207–215.
Workman et al., J. Biol. Chem. (1977) 252(20):7118–7123.
Greco et al., Blood (1990) 75(10):1983–1990.
Bode et al., EMBO J. (1989) 8(11):3467–3475.
Van Obberghen–Schilling et al., FEBS Letters (1990) 262(2):330–334.
Pipili–Synetos et al., Biochem. Biophys. Res. Comm. (1990)171(3):913–919.

Primary Examiner—Cecilia J. Tsang
Assistant Examiner—S. G. Marshall
Attorney, Agent, or Firm—Morrison&FoersterLLP

[57] ABSTRACT

The DNA encoding the cell surface receptor for thrombin has been cloned and sequenced. The availability of this DNA permits the recombinant production of thrombin receptor which can be produced at cell surfaces and is useful in assay systems both for the detection of thrombin and for the evaluation of candidate thrombin agonists and antagonists. Further, the elucidation of the structure of the thrombin receptor permits the design of agonist and antagonist compounds which are useful diagnostically and therapeutically. The availability of the thrombin receptor also permits production of antibodies specifically immunoreactive with the receptor per se or with specific regions thereof which are also useful diagnostically or therapeutically.

9 Claims, 11 Drawing Sheets

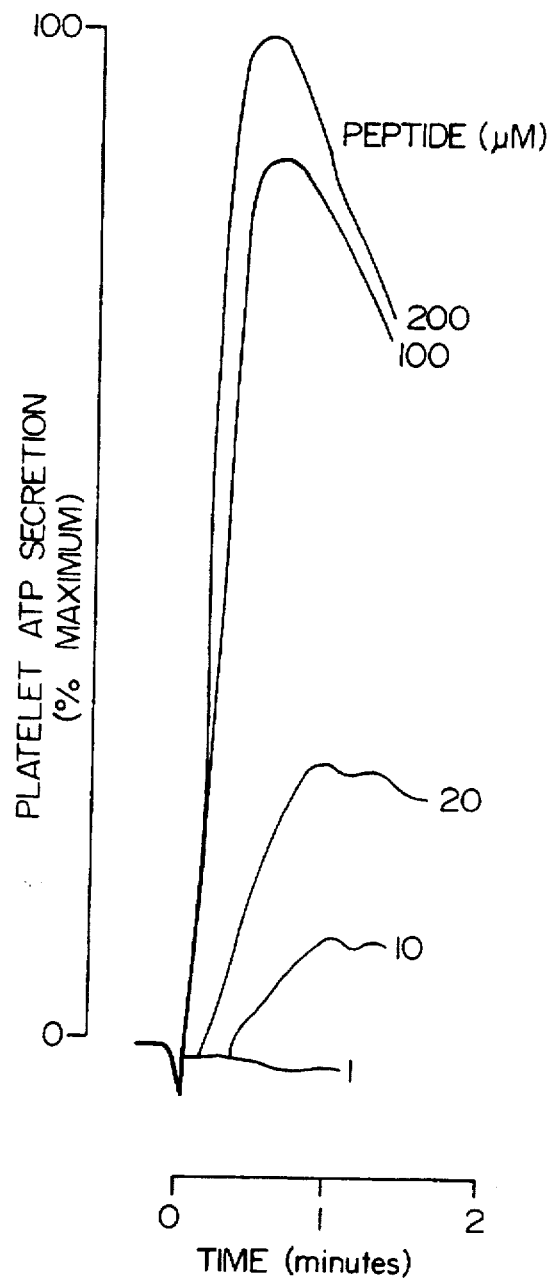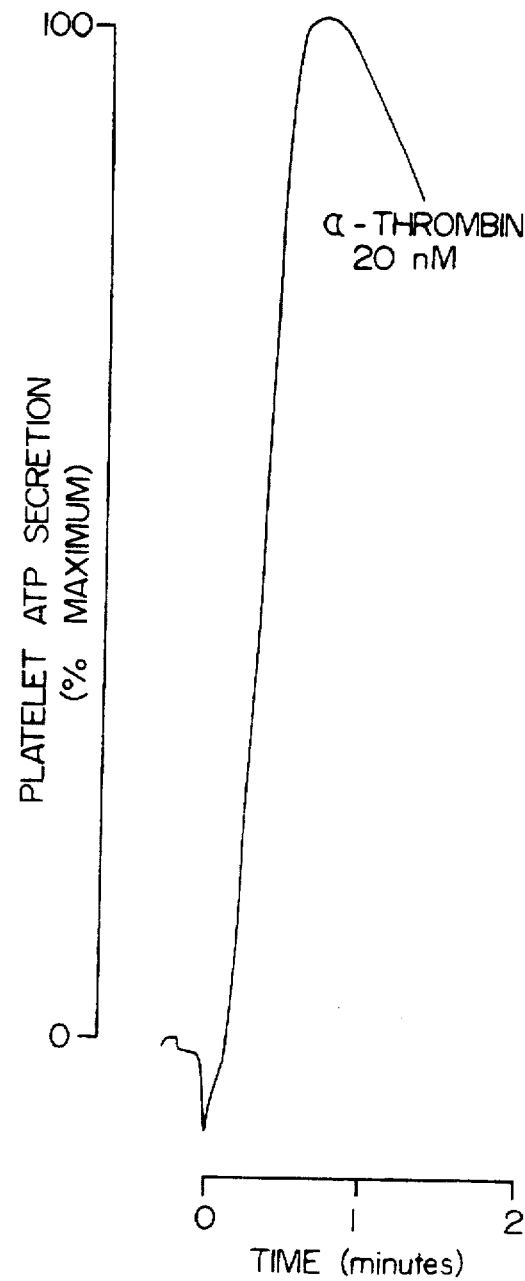
FIG. 4B
FIG. 4C

RECOMBINANT THROMBIN RECEPTOR AND RELATED PHARMACEUTICALS

This is a continuation-in-part of U.S. patent application Ser. No. 07/657,769, filed 19 Feb. 1991, now U.S. Pat. No. 5,256,766.

This invention was made with Government support under NIH Contract No. HLBI RO1-44907 awarded by the National Institutes of Health. The Government has certain rights in this invention.

TECHNICAL FIELD

The invention relates to materials involved in the control of the cardiovascular system, and in particular to activities mediated by thrombin and its cellular receptor. More specifically, it concerns recombinant materials useful for production of the thrombin receptor, use of the receptor as a diagnostic tool, and therapeutic agents which either stimulate or block thrombin receptor activation and diagnostic compositions relevant to the receptor.

BACKGROUND ART

Thrombin is a powerful factor in regulating the state of the cardiovascular system. It is clear that thrombin aids in the formation of blood clots by catalyzing the conversion of fibrinogen to fibrin, which is an integral part of most clots. In addition, thrombin is known to act directly on cells in the blood and in the interior blood vessel wall, and specifically to activate platelets to form clots. Thrombin-induced platelet activation is particularly important for arterial thrombus formation, a process that causes myocardial infarction and some forms of unstable angina and stroke. In addition thrombin promotes inflammation and other cellular activities. Thrombin is chemotactic for monocytes, mitogenic for lymphocytes, and causes endothelial cells to express the neutrophil adhesive protein GMP-140 on their surfaces and inhibits the growth of these cells. Thrombin elicits platelet-derived growth factor from the endothelium and is a mitogen for mesenchymal cells.

Because thrombin is capable of direct activation of cells, it is assumed that at least one thrombin receptor exists. However, it has not been possible to detect the presence of thrombin receptor by traditional binding studies, since thrombin is capable of binding a large number of materials present on cells which do not directly mediate the cellular responses to thrombin, and thus the background levels of binding are prohibitively high.

The thrombin-binding proteins that have been identified do not seem to function as transduction molecules (Gronke, R. S., et al., *J Biol Chem* (1987) 262: 3030–3036; Okamura, T., et al., *J Biol Chem* (1978) 253: 3435). Modified thrombins that are physiologically inactive seem to bind to platelets in the same way as thrombin itself. Thus, the binding sites identified by traditional binding studies may not be related to functional thrombin receptors. Also, since thrombin is a protease, if the receptor were proteolytically cleaved by the interaction with thrombin, the receptor's ability to bind tightly to thrombin would be decreased. All of the foregoing factors suggest that traditional binding studies in an effort to find a thrombin receptor might ultimately be unproductive.

While it has been assumed that a thrombin receptor might exist, it has been unclear, even from the studies conducted so far, whether proteolytic cleavage by thrombin is involved in its receptor activation. When thrombin is treated with reagents which covalently modify and render it proteolytically inactive, its ability to stimulate platelets is abolished (Berndt, M. C., et al., "Platelets in Biology and Pathology" (1981) Elsevier/North Holland Biomedical Press, pp. 43–74; Martin, B. M., et al., *Biochemistry* (1975) 14: 1308–1314; Tollefsen, D. M., et al., *J Biol Chem* (1974) 249: 2646–2651; Phillips, D. R., *Thrombin Diath Haemorrh* (1974) 32: 207–215; Workman, E. F., et al., *J Biol Chem* (1977) 252: 7118–7123; Greco, N.J., et al., *Blood* (1990) 75: 1983–1990). The modified forms of thrombin described in the reports above contain bulky or charged moieties that occupy the active site and also obscure additional regions of the surface of thrombin that bind substrate (Bode, W., et al., *Embo J* (1989) 8: 3467–3475). Some of the chemically-modified thrombins do not, in fact, block thrombin-induced platelet activation and one modified nonproteolytic thrombin which does block platelet activation, D-phenylalanyl-L-prolyl-L-arginyl chloromethyl ketone (PPACK) thrombin fails to bind substrate. Thus, it cannot be concluded that a lack of protease activity accounts for failure to activate platelets.

During the course of the work described in the present application, two groups have reported that messenger RNA prepared from thrombin-responsive cell lines, when microinjected into Xenopus oocytes, conferred thrombin responsiveness on the oocytes. The mRNA was prepared either from a hamster lung fibroblast cell line, CCL39 (Van Obberghen-Schilling, E., et al., *FEBS Letters* (1990) 262: 330–334) or from human umbilical venous endothelial cells (Pipili-Synetos, E., et al., *Biochem Biophys Res Commun* (1990) 171: 913–919).

The identification and characterization of the thrombin receptor, as described herein, permits the design of systems and substances which can regulate thrombosis in the cardiovascular system. In addition, new diagnostic reagents for assessing cardiovascular status are provided by this work.

DISCLOSURE OF THE INVENTION

The invention provides methods and materials useful in the regulation of the cardiovascular system in mammals. The isolation, recombinant production, and characterization of the thrombin receptor associated with surfaces of cells activated by thrombin permits effective regulation of these functions.

Thus, in one aspect, the invention is directed to recombinant materials associated with the production of thrombin receptor. These include, for example, transfected cells which can be cultured so as to display the thrombin receptor on their surfaces, and thus provide an assay system for the interaction of materials with native thrombin receptor. These cells, or peptides which represent relevant portions of the receptors, can be used as diagnostics to determine the level of thrombin in samples, as well as screening tools for candidate substances which affect thrombin activity in vivo.

In another aspect, the invention is directed to thrombin receptor agonists which mimic the activated form of the extracellular portion of the receptor protein. These agonists are useful in encouraging platelet aggregate formation, for example, in localized application at internal bleeding sites of hemophiliacs. The agonists also mimic thrombin's ability to stimulate fibroblast proliferation and thus may be useful in promoting wound healing.

In still another aspect, the invention is directed to thrombin receptor antagonists. These antagonists comprise modified forms of thrombin receptor agonist peptides which lack the essential features required for activation of the receptor. These antagonists bind to receptor, do not activate it, and prevent receptor activation by thrombin.

A second group of compounds of the invention that antagonize the action of thrombin are, in effect, thrombin inhibitors. This group includes mimics of the receptor which would ordinarily represent cleavage and thrombin-binding regions of the receptor, including noncleavable peptides and peptides with enhanced binding for thrombin. These peptides are capable of binding directly to thrombin so as to diminish the levels of thrombin capable of binding to receptor. They thus diminish or prevent thrombin-mediated events such as thrombin-induced platelet aggregation, fibrinogen clotting and cell proliferation.

A third group of compounds which behave as antagonists blocks the binding of thrombin to its receptor by providing alternate anionic regions to replace those of the thrombin receptor. These antagonists are mimics of the anionic region included in the thrombin-binding portion of the receptor. These antagonists also bind to thrombin, thereby preventing thrombin interaction with the intact receptor.

Conversely, alternate cationic regions which mimic those present in the thrombin ligand can be included in antagonists which occupy the binding region of the receptor and thus prevent binding of thrombin.

A fifth group of antagonists will include antibodies which are designed to bind specific regions of receptor protein. In general, these are monoclonal antibody preparations which are highly specific for any desired region of the thrombin receptor. The antibodies of the invention are also useful in immunoassays for the receptor protein, for example in assessing successful expression of the gene in recombinant systems.

A sixth group of antagonists comprises modified forms of thrombin lacking proteolytic activity.

In another aspect, the invention is related to assay systems which utilize recombinant thrombin receptor to screen for agonists and antagonists. Some systems include the use of the agonist peptides to screen for antagonists which inhibit the agonistic effect.

Another aspect of the invention relates to the diagnosis of cardiovascular disease by detection, in fluids such as blood or urine, of the peptide cleaved from the thrombin receptor when activated as a measure of thrombosis. Another diagnostic method included in the invention is visualization of activated forms of receptor and detecting clots in the body by localizing and imaging these targets in situ using antibodies specific to the activated receptor.

Additional aspects of the invention are directed to pharmaceutical compositions containing the compounds of the invention. The compounds of the invention which serve as antagonists to the activation of the thrombin receptor are useful as anti-thrombotics and are helpful in a variety of clinical indications including treatment of abrupt closure in the context of angioplasty, the treatment of restenosis in the context of angioplasty, the treatment of unstable angina, the treatment of myocardial infarction, and treatment of some forms of thrombotic or thromboembolytic stroke. The compounds of the invention can be used alone or in combination with other therapeutic agents such as urokinase and tPA.

BRIEF DESCRIPTION OF THE DRAWINGS

FIGS. 1a and b shows the DNA and deduced amino acid sequence of a human thrombin receptor SEQ ID NO: 219–SEQ ID NO: 220.

FIGS. 4a–c shows platelet response to agonist peptide.

MODES OF CARRYING OUT THE INVENTION

Figure 1A:
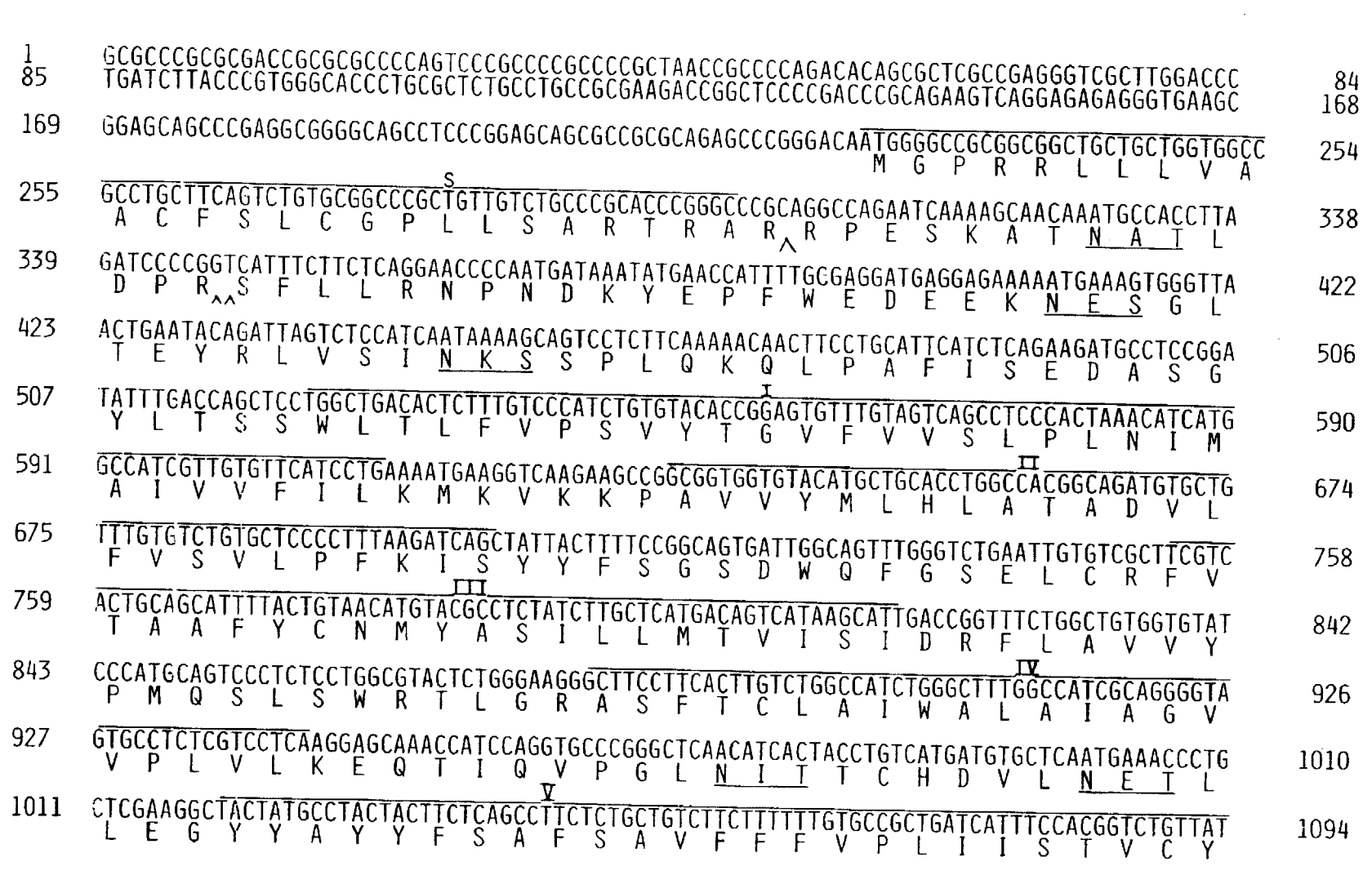
Figure 1B:
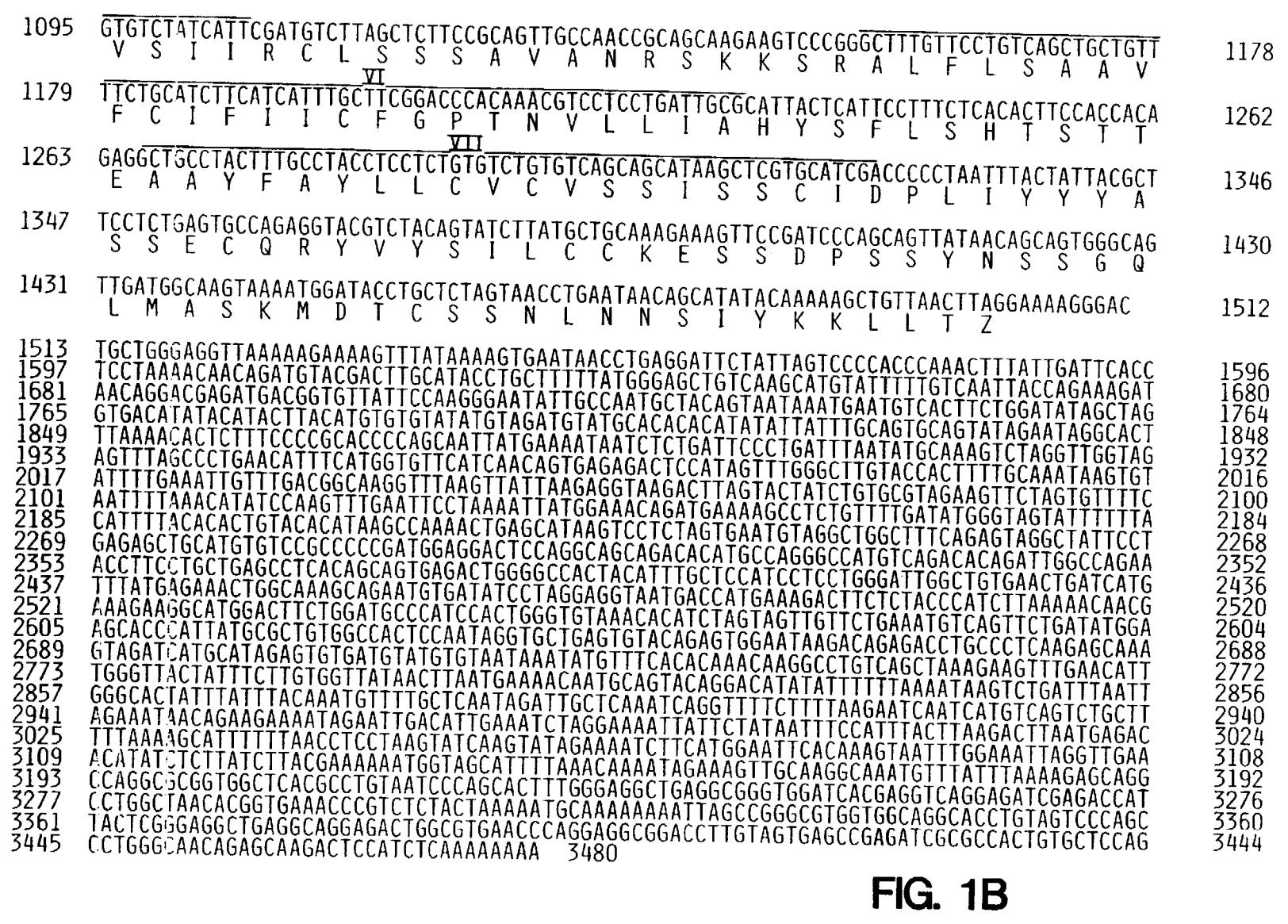
Figure 2:
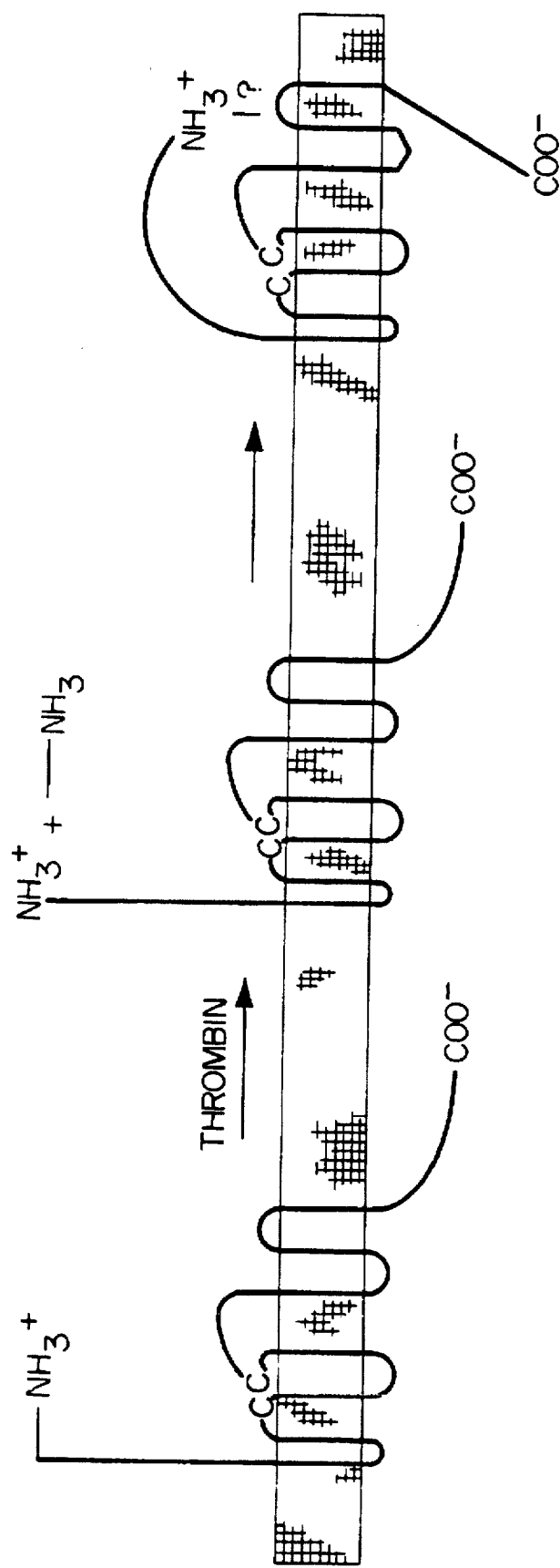
FIG. 2 shows a proposed model of thrombin receptor activation based on the deduced amino acid sequence.

The characteristics of the thrombin receptor elucidated by the invention herein are summarized in FIGS. 1 and 2. FIG. 1 shows the complete DNA sequence of the clone encoding the receptor along with the deduced amino acid sequence. The entire amino acid sequence contains 425 amino acids, including a 24 or 26 amino acid signal sequence which provides an approximately 400 amino acid mature receptor protein.

Hydrophobicity/hydrophilicity plots of the sequence shown in FIG. 1 indicate that the mature receptor is a member of the 7-transmembrane domain receptor family and has a relatively long (approximately 75 amino acid) extracellular amino acid extension containing several consensus sites for asparagine-linked glycosylation. A disulfide bond linking cysteine-175 in the first extracellular loop with cysteine-254 in the second extracellular loop would be analogous to rhodopsin and β-2 adrenergic receptor. A proposed model of the in situ receptor is shown in FIG. 2.

Referring again to FIG. 1, the thrombin-catalyzed cleavage site is represented by the Arg-Ser linkage at positions 41 and 42. cleavage at this site results in the liberation of a peptide fragment of the receptor designated an "activation peptide" extending from position 1 of the mature peptide to the cleavage site. The precise processing site of the receptor is not known and thus the N-terminus of the mature protein is somewhat uncertain. However, it is probably the arginine residue at position 28. The "activation peptide" would thus have the sequence SEQ ID NO: 1. The precise location of the N-terminus is unimportant for the design of the compounds of the invention. This "activation peptide" is likely to be freely filtered by the kidney and possibly concentrated in the urine, and can be used as an index to platelet activation by thrombin.

The amino acid sequence destined to be cleaved by thrombin—i.e., the cleavage site—binds to thrombin's active site/"oxyanion hole" region which is contained in an extended binding pocket. This oxyanion hole binds large substrates via hydrophobic, hydrogen bonding, and charge interactions. Typically, the sequence to be cleaved interacts with the amino acids of the active site, while sequences carboxyl to this cleavage site interact with the more extended "anion binding exosite." The thrombin receptor contains the anionic sequence SEQ ID NO: 2 at positions 52–60, as shown in FIG. 1. This region is just carboxyl to the cleavage site between positions 41 and 42. The location and the composition of this SEQ ID NO: 2 sequence (aromatic/hydrophobic residues and anionic residues) strongly suggest that this sequence contains regions that mediate thrombin binding to the receptor via thrombin's anion-binding exosite. This hypothesis is confirmed hereinbelow by showing that peptides representing at least a portion of this region of the receptor bind thrombin and inhibit its actions. This observation also predicts that polycationic substances that bind to this portion of the receptor may block thrombin binding and receptor activation.

Release of the activation peptide permits refolding of the receptor protein to activate the receptor. This is shown schematically in FIG. 2, which also shows that the conformational changes resulting from the liberation of the activation peptide and refolding results in an intracellular conformational change of the receptor. This hypothesis is confirmed by the finding that the thrombin receptor can be activated by a peptide mimicking the new amino terminus created by the activation. Accordingly, mimics of the N-terminus of the new amino terminus on the activated receptor behave as agonists therefor. The importance of the first two amino acids in the newly created amino terminus in the receptor for receptor activation has also been confirmed hereinbelow. Switching the positions of the amino terminal serine and phenylalanine results in complete loss of agonist activity for the above agonist peptides. Based on this information, and by analogy with the mechanisms underlying trypsinogen activation to trypsin, it appears that the positively charged amino group on serine that is newly exposed when thrombin cleaves the receptor plays an important role in receptor activation. Peptides based on the agonist peptide sequence that bind the thrombin receptor but are modified to be lacking the α-amino group can function as antagonists of the thrombin receptor. Thus, modifications of the agonist peptides which lack the capacity for specific activating interaction serve as thrombin receptor antagonists.

COMPOUNDS OF THE INVENTION

The nomenclature used to describe the peptide compounds of the invention follows the conventional practice where the N-terminal amino group is assumed to be to the left and the carboxy group to the right of each amino acid residue in the peptide. In the formulas representing selected specific embodiments of the present invention, the amino- and carboxy-terminal groups, although often not specifically shown, will be understood to be in the form they would assume at physiological pH values, unless otherwise specified. Thus, the N-terminal $H^+_2$ and C-terminal $O^-$ at physiological pH are understood to be present though not necessarily specified and shown, either in specific examples or in generic formulas. Free functional groups on the side chains of the amino acid residues can also be modified by amidation, acylation or other substitution, which can, for example, change the solubility of the compounds without affecting their activity.

In the peptides shown, each gene-encoded residue, where appropriate, is represented by a single letter designation, corresponding to the trivial name of the amino acid, in accordance with the following conventional list:

| Amino Acid | One-Letter Symbol | Three-letter Symbol |
|---|---|---|
| Alanine | A | Ala |
| Arginine | R | Arg |
| Asparagine | N | Asn |

-continued

| Amino Acid | One-Letter Symbol | Three-letter Symbol |
|---|---|---|
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The amino acids not encoded genetically are abbreviated as indicated in the discussion below.

In the specific peptides shown in the present application, the L-form of any amino acid residue having an optical isomer is intended unless the D-form is expressly indicated by a dagger superscript (†).

The compounds of the invention are peptides which are partially defined in terms of amino acid residues of designated classes. Amino acid residues can be generally subclassified into four major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/nonpolar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

For the naturally occurring protein amino acids, subclassification according to the foregoing scheme is as follows.

Acidic: Aspartic acid and Glutamic acid;

Basic/noncyclic: Arginine, Lysine;

Basic/cyclic: Histidine;

Neutral/polar/small: Glycine, serine, cysteine;

Neutral/nonpolar/small: Alanine;

Neutral/polar/large/nonaromatic: Threonine, Asparagine, Glutamine;

Neutral/polar/large aromatic: Tyrosine;

Neutral/nonpolar/large/nonaromatic: Valine, Isoleucine, Leucine, Methionine;

Neutral/nonpolar/large/aromatic: Phenylalanine, and Tryptophan.

The gene-encoded secondary amino acid proline, although technically within the group neutral/nonpolar/large/cyclic and nonaromatic, is a special case due to its known effects on the secondary conformation of peptide chains, and is not, therefore, included in this defined group.

Certain commonly encountered amino acids, which are not encoded by the genetic code, include, for example, beta-alanine (beta-Ala), or other omega-amino acids, such as 3-amino propionic, 4-amino butyric and so forth, alpha-aminisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), cysteic acid (Cya) 2-naphthylalanine (2-Nal); 1,2,3,4-tetrahydroisoquinoline-3-carboxylic acid (Tic); β-2-thienylalanine (Thi); and methionine sulfoxide (MSO). These also fall conveniently into particular categories.

Based on the above definitions,

Sar and beta-Ala and Aib are neutral/nonpolar/small;

t-BuA, t-BuG, N-MeIle, Nle, Mvl and Cha are neutral/nonpolar/large/nonaromatic;

Orn is basic/noncyclic;

Cya is acidic;

Cit, Acetyl Lys, and MSO are neutral/polar/large/nonaromatic; and

Phg, Nal, Thi and Tic are neutral/nonpolar/large/aromatic.

The various omega-amino acids are classified according to size as neutral/nonpolar/small (beta-Ala, i.e., 3-aminopropionic, 4-aminobutyric) or large (all others).

Other amino acid substitutions of those encoded in the gene can also be included in peptide compounds within the scope of the invention and can be classified within this general scheme according to their structure.

All of the compounds of the invention, when an amino acid forms the C-terminus, may be in the form of the pharmaceutically acceptable salts or esters. Salts may be, for example, $Na^+$, $K^+$, $Ca^{+2}$, $M^{+2}$ and the like; the esters are generally those of alcohols of 1–6C.

A. Agonists

The agonists of the invention comprise a series of peptides of the formula

(1)

wherein $AA_x$ is a small amino acid or threonine, preferably selected from ser, ala, gly and, and thr and $AA_y$ is a neutral/nonpolar/aromatic amino acid residue or is a neutral/nonpolar/large/nonaromatic amino acid containing a cyclic portion (preferably a neutral/nonpolar/aromatic amino acid residue);

wherein AA represents an amino acid residue and the subscript i is an integer which denotes the position of the referent amino acid residue downstream (N→C) of the $AA_y$ residue of formula (1), and n is an integer of 2–12, with the proviso that if n=2, Z must comprise an amidated C terminus of the formula NR'R' wherein at least one R' is alkyl containing at least one polar substituent; and in general, Z is a noninterfering substituent.

$AA_1$ and $AA_2$ must, therefore, be present in the compounds of formula 1; $AA_3$–$AA_{12}$ are optional. $AA_1$ and $AA_2$ are relatively precisely defined; however $AA_3$–$AA_{12}$ are, generally, L-amino acid residues. The position of $AA_1$ is also relatively tolerant; therefore, $AA_1$ is a neutral or basic amino acid having a free α-amino group in the L-configuration;

$AA_2$ is a neutral or basic L-amino acid residue; and $AA_3$–$AA_{12}$ are L-amino acid residues, wherein preferably $AA_3$ is a basic or neutral amino acid residue;

$AA_4$ and $AA_6$ are each independently neutral/polar/large/nonaromatic amino acids or $AA_4$ may be a basic amino acid;

$AA_5$ and $AA_{11}$ are each independently proline or small amino acid residues;

$AA_7$ and $AA_{10}$ are each independently acidic amino acid residues;

$AA_8$ is a basic amino acid residue; and $AA_9$ and $AA_{12}$ are each independently neutral/aromatic amino acid residues.

The peptide of formula 1 can be extended (shown as included in Z) at the C-terminus (but not the N-terminus) by further amino acid sequence to comprise a noninterfering substituent.

At the C-terminus of the compounds of formula 1, the carboxyl group may be in the underivatized form or may be amidated; in the underivatized form the carboxyl may be as a free acid or a salt, preferably a pharmaceutically acceptable salt.

If the C-terminus is amidated, the nitrogen atom of the amido group, covalently bound to the carbonyl carbon at the C-terminus, will be NR'R', wherein each R' is independently hydrogen or is a straight or branched chain alkyl of 1–6C, such alkyls are 1–6C straight- or branched-chain saturated hydrocarbyl residues, such as methyl, ethyl, isopentyl, n-hexyl, and the like. Representatives of such amido groups are: —$NH_2$, —$NHCH_3$, —$N(CH_3)_2$, —$NHCH_2CH_3$, —$NHCH_2CH(CH_3)_2$, and —$NHCH_2CH(CH_3)CH_2CH_3$, among others. Furthermore, either or both R' may in turn optionally be substituted by one or more substituents such as, for example, —OR', —NR'R', halo, —NR'CNR'NR'R' and the like, wherein each R' is as independently defined above. Thus, Z may be —OH (or an ester or salt form), or —NR'R' wherein R' is as above defined.

Preferred embodiments of $AA_x$–$AA_y$ include GF, AF, SF, TF, G(pClPhe), A(pClPhe), S(pClPhe), T(pClPhe), GThi, AThi, SThi, and TThi. Preferred embodiments of $AA_1$ and $AA_2$ are large nonpolar amino acids. Preferred embodiments for the residues in the remainder of the compound of formula (1) are those wherein $AA_1$ and $AA_2$ are each independently Leu, Val, Ile, Cha, Phe, 2-Nal or Tic; or $AA_3$ is Arg, Lys, Orn, Har or Ala. For the remaining amino acids, preferred are embodiments wherein $AA_4$ and $AA_6$ are each independently Gln, Asn or Lys; or $AA_7$ and $AA_{10}$ are each independently Asp or Glu; $AA_8$ is Arg or Lys; or $AA_{12}$ is Phe and $AA_9$ is Tyr; or Z is OH, or NR'R' wherein R' is as defined above; or Z further includes some or all of $AA_{13}$–$AA_{17}$ as defined below. Particularly preferred are compounds of formula (1) which are selected from the group consisting of SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; and the amidated forms thereof.

B. Antagonists

Compounds of the invention which interfere with platelet activation and other cellular activities mediated by the thrombin receptor include the following:

1) Antagonists for the thrombin receptor which represent modified agonist peptides lacking the N-terminal serine residue;

2) Thrombin inhibitors which represent noncleavable and/or enhanced binding forms of the extracellular portions of the thrombin receptor which behave as decoys for the circulating thrombin;

3) Anionic and hydrophobic/anionic peptides which mimic at least a portion of the SEQ ID NO: 2; anionic-binding exosite region and which also behave as decoys for circulating thrombin;

4) Cationic or extended cationic peptides which mimic the anionic-binding exosite of thrombin itself and bind to the receptor in competition with thrombin;

5) Antibodies which are immunoreactive with various critical positions on the thrombin receptor; and 6) Thrombin mutants lacking proteolytic activity which compete with native thrombin for the receptor.

Thrombin Receptor Antagonists

The antagonists of the first group—modified agonists—can be represented by the formula:

$$X\text{-}AA_y\text{-}(AA_i)_n\text{-}Z \qquad (2)$$

wherein

X is an amino acid residue other than Ser, Ala, Thr, Cys or Gly or is a desamino or N-acylated amino acid;

$AA_y$ is a neutral nonpolar large amino acid residue containing a cyclic portion, preferably aromatic;

AA represents an amino acid residue and the subscript i is an integer which denotes the position of the referent amino acid residue downstream (N→C) of the $AA_y$ residue of formula (2) and n is an integer of 4–12; and wherein $AA_1$ and $AA_2$ are each independently neutral or basic L-amino acid residues wherein $AA_1$ has a free α-amino group;

$AA_3$ and $AA_8$ are each independently basic or neutral amino acid residues;

$AA_4$ and $AA_6$ are each independently basic or nonaromatic amino acids;

$AA_5$ and $AA_{11}$ are each independently proline residues or small amino acids;

$AA_7$ and $AA_{10}$ are each independently acidic amino acid residues;

$AA_9$ and $AA_{12}$ are each independently neutral/aromatic amino acid residues; and Z is a noninterfering substituent.

Preferred embodiments of X include residues of 3-mercaptopropionic acid (Mpr), 3-mercaptovaleric acid (Mvl), 2-mercaptobenzoic acid (Mba) and S-methyl-3-mercaptopropionic acid (SMeMpr).

Preferred embodiments for this group of anti-thrombin activity compounds include those wherein $AA_1$ and $AA_2$ are each independently Leu, Val, Ile, Phe, Cha, 2-Nal or Tlc; or $AA_3$ and $AA_8$ are each independently Arg, Lys, Orn or Har; or $AA_4$ and $AA_6$ are each independently Lys, Arg, Orn, Har, Gly, Gln or Asn; or $AA_5$ and $AA_{11}$ are each independently Pro or Ala; or $AA_7$ and $AA_{10}$ are each independently Asp, Glu, β-Asp or β-Glu; or $AA_{12}$ is Phe and $AA_9$ is Tyr; or Z is OH (or an ester or salt form), $NH_2$, or NR'R' wherein each R' is independently H or straight- or branched-chain alkyl of 1–6C optionally substituted as described above.

Particularly preferred embodiments are those peptides wherein X is Mpr, S-Me Mpr or Mba, $AA_y$ is Phe, $AA_1$ is Cha, and $AA_2$ is Cha.

Particularly preferred are embodiments of $AA_1$–$AA_{12}$ which are encoded by the gene, or wherein $AA_1$ and $AA_2$ can each independently be Cha. Particularly preferred among the antagonist peptides of this class are those selected from the group consisting of SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; XFL; SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, , X-F(Cha) (Cha)RKPNDK-$NH_2$ SEQ ID NO: 45, SEQ ID NO: 46, X-F(Cha) (Cha)RNPADK-$NH_2$ SEQ ID NO: 47, SEQ ID NO: 48, X-F(Cha) (Cha)RKPNEK-$NH_2$ SEQ ID NO: 49, and SEQ ID NO: 50; especially wherein X is Mpr.

Especially preferred are SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, and SEQ ID NO: 67.

Thrombin Inhibitors

The thrombin inhibitors of group 2) represent compounds that bind thrombin in competition with receptor but are noncleavable and/or exhibit enhanced binding properties. These compounds are of the formula:

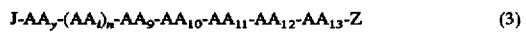

$$J\text{-}AA_y\text{-}(AA_i)_n\text{-}AA_9\text{-}AA_{10}\text{-}AA_{11}\text{-}AA_{12}\text{-}AA_{13}\text{-}Z \qquad (3)$$

wherein J is a peptide extension of 2–5 amino acid residues or an acylated or desamino form thereof.

In the compounds of formula (3), as above, $AA_y$ is a neutral nonpolar large amino acid residue containing a cyclic portion, preferably aromatic; and n is 8.

As above,

AA represents an amino acid residue and the subscript i is an integer denoting position downstream from $AA_y$.

As above, $AA_1$ and $AA_2$ are each independently neutral or basic amino acid residues;

$AA_3$ and $AA_8$ are each independently neutral or basic amino acid residues;

$AA_4$ and $AA_6$ are each independently basic or neutral nonaromatic amino acids;

$AA_5$ and $AA_{11}$ are each independently proline residues or small amino acids;

$AA_7$ and $AA_{10}$ are each independently acidic amino acid residues;

$AA_9$ and $AA_{12}$ are each independently neutral/aromatic amino acid residues;

AA$_{13}$ is an aromatic or small nonpolar amino acid residue; and

Z is a noninterfering substituent.

For these thrombin inhibitors which are of group (2) above, wherein the peptide mimics the thrombin receptor extracellular chain but lacks a proteolytic site and/or has enhanced binding for thrombin, particularly preferred embodiments are those which include downstream anionic amino acid residues and wherein J is a peptide extension of 4–5 amino acid residues. Particularly preferred are those wherein the residues immediately upstream of AA$_y$ have the sequence pro-arg-pro (PRP) preceded by residues selected from the group consisting of dipeptide sequences consisting of a large/nonaromatic/nonpolar/neutral amino acid residue conjugated through a peptide bond to an acidic amino acid residue downstream. Particularly preferred embodiments of this dipeptide sequence are ile-asp, val-asp, ile-glu, and leu-asp, especially wherein said peptide extension represented by J is selected from the group consisting of SEQ ID NO: 68, SEQ ID NO: 69, SEQ ID NO: 70, SEQ ID NO: 71, SEQ ID NO: 72 and SEQ ID NO: 73.

In addition, where the peptide extension includes the immediately upstream sequence pro-arg-pro, an additional preferred upstream further extension is a D amino acid. Particularly preferred are D amino acids which are large/ nonpolar/neutral/aromatic, particularly tryptophan or phenylalanine, and in particular phenylalanine.

Z is preferably OH (or an ester or salt form) or NR'R', where R' is defined as above, which may optionally be preceded by a peptide extension mimicking the receptor sequence downstream from AA$_{13}$.

Particularly preferred compounds of formula (3) are peptides which are selected from the group consisting of SEQ ID NO: 74; SEQ ID NO: 75; SEQ ID NO: 76; SEQ ID NO: 77; SEQ ID NO: 78; SEQ ID NO: 79; and SEQ ID NO: 80, and the amidated or acylated forms thereof. Also preferred are those which are selected from the group consisting of
F†PRPFLLRNPNDKYEPFWEDEEKNES,
F†PRPFLLRNPNDKYEPFWEDEEKNE,
F†PRPFLLRNPNDKYEPFWEDEEKN,
F†PRPFLLRNPNDKYEPFWEDEEK,
F†PRPFLLRNPNDKYEPFWEDEE,
F†PRPFLLRNPNDKYEPFWEDE, and
F†PRPFLLRNPNDKYEPFWED;        and
F†PRPFLLRNPNDKYEPFWEDEEKNES,
F†PRPFLRNPNDKYEPFWEDEEKNES,
F†PRPFRNPNDKYEPFWEDEEKNES,
F†PRPFNPNDKYEPFWEDEEKNES,
F†PRPFPNDKYEPFWEDEEKNES,
F†PRPFNDKYEPFWEDEEKNES,
F†PRPFDKYEPFWEDEEKNES,
F†PRPFKYEPFWEDEEKNES,
F†PRPFYEPFWEDEEKNES,             and
F†PRPFEPFWEDEEKNES, and the amidated and acylated forms thereof.

Anion Exosite-Binding Antagonists

Antagonists which represent peptides mimicking the binding region of the receptor, SEQ ID NO: 81, optionally including the anionic extension (SEQ ID NO: 82) thereof (group 3), are represented by the formula:

B-AA$_9$-AA$_{10}$-AA$_{11}$-AA$_{12}$-AA$_{13}$-Z    (4)

wherein AA$_9$, AA$_{12}$ and AA$_{13}$ are each, independently, neutral aromatic or small amino acid residues, AA$_{10}$ is an acidic amino acid residue, AA$_{11}$ is proline or a small amino acid residue; and wherein B and Z are noninterfering substituents, typically peptide extensions, but can also include noninterfering organic radicals in general. B can also be H or acyl (including said peptide extension if present); Z may also be OH (or an ester or salt form thereof) or NR'R' (also including said peptide extension if present), as set forth hereinabove.

Preferred forms of compounds of formula (4) are those wherein each of AA$_9$, AA$_{12}$ and AA$_{13}$ is phe, trp, ala or tyr; and AA$_{10}$ is glu, asp, β-glu or β-asp. Particularly preferred are embodiments wherein AA$_9$–AA$_{13}$ is SEQ ID NO: 81, SEQ ID NO: 83, SEQ ID NO: 84, SEQ ID NO: 85, SEQ ID NO: 86, SEQ ID NO: 87 or SEQ ID NO: 88. Z may include the peptide sequence SEQ ID NO: 89, SEQ ID NO: 90, SEQ ID NO: 91, SEQ ID NO: 92, SEQ ID NO: 93, SEQ ID NO: 94, SEQ ID NO: 95, or SEQ ID NO: 96.

Preferred embodiments of B include those wherein B is H or a peptide extension of 1–4 amino acids or the acylated form thereof.

These antagonists serve as decoys for thrombin, thus lowering its effective concentration.

Anionic-Binding Exosite Mimics

The cationic peptides mimicking a portion of the anionic-binding exosite of thrombin (group 4) are of the formula:

B-AA$_a$-AA$_b$-AA$_c$-AA$_d$-AA$_e$-Z    (5)

wherein B and Z are defined as above, and wherein AA$_a$ and AA$_e$ are each independently hydrophobic amino acids or basic amino acids, and where each of AA$_b$, AA$_c$, and AA$_d$ is independently a basic amino acid.

Preferred are compounds of formula (5) wherein B comprises acyl or H; or Z comprises OH (or an ester or salt) or NR'R' wherein each R' is defined as above; or AA$_a$ and AA$_e$ are each independently selected from phe, trp and ala; or AA$_b$–AA$_d$ are each independently selected from the group consisting of arg, lys and gln; especially wherein AA$_a$–AA$_e$ has the sequence SEQ ID NO: 97, SEQ ID NO: 98, SEQ ID NO: 99, or SEQ ID NO: 100.

The noninterfering substituents represented by B and Z may be further peptide extensions which are compatible with the binding pattern of the thrombin anionic-binding exosite. As they mimic this capacity of thrombin to bind its substrate, these antagonists are operative by virtue of their ability to bind the relevant regions of the thrombin receptor protein, and, in particular, the region SEQ ID NO: 2 at positions 52–60, as shown in FIG. 1.

Antibodies

Antagonists which are antibodies immunoreactive with critical positions of the thrombin receptor (group 5) are obtained by immunization of suitable mammalian subjects with peptides containing as antigenic regions those portions of the thrombin receptor intended to be targeted by the antibodies. Critical regions include the region of proteolytic cleavage, the binding site at the SEQ ID NO: 2 box, the segment of the extracellular segment critical for activation (this includes the cleavage site), and the portions of the sequence which form the extracellular loops, in particular, that region which interacts with the N-terminus of the activated receptor extracellular region. The agonist peptides of the invention may be used as immunogens in this case.

Thus, suitable peptides to use as immunogens to prepare the desired antibodies include those peptides representing portions of the mature sequence of the extracellular region from positions 28 to position 68, at the C-terminal end of the SEQ ID NO: 2 region. This region has the sequence:

SEQ ID NO: 101

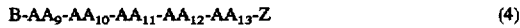

and peptides which include the sequence LDPRSFLL (which includes the cleavage site) and YEPFWEDEE (which includes the binding site) are particularly useful. Alternative regions which are useful as immunogens include the segment representing amino acids 161–176; 240–265; and 336–346. These peptides of the sequences, respectively, SEQ ID NO: 102, SEQ ID NO: 103, and SEQ ID NO: 104, represent the proposed extracellular loops.

The antibodies are prepared by immunizing suitable mammalian hosts in appropriate immunization protocols using the peptide haptens alone, if they are of sufficient length, or, if desired, or if required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the hapten. The hapten peptides can be extended at the amino or carboxy terminus with a Cys residue or interspersed with cysteine residues, for example, to facilitate linking to carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein or modifications which effect immortalization of lymphocytes or spleen cells, as is generally known. The immortalized cell lines secreting the desired antibodies are screened by immunoassay in which the antigen is the peptide hapten or is the thrombin receptor itself displayed on a recombinant host cell. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of F(ab')$_2$ fragments is often preferable, especially in a therapeutic context, as these fragments are generally less immunogenic than the whole immunoglobulin.

The antibodies or fragments may also be produced, using current technology, by recombinant means. Regions that bind specifically to the desired regions of receptor can also be produced in the context of chimeras with multiple species origin.

Nonclearable Thrombin

In addition to the foregoing, antagonists comprise thrombin mutants lacking proteolytic activity that compete with native thrombin for the receptor (group 6). As set forth above, it is understood that the participants in the proteolytic cleavage site of thrombin include the serine residue at B-chain position 205, the histidine residue at position 57, and the aspartic acid residue at position 99. Mutants of thrombin containing replacements for these residues which render the thrombin molecule proteolytically inactive are prepared using standard site-directed mutagenesis techniques, and the mutant genes used to produce the modified thrombin using recombinant techniques. The relevant substitutions are denoted by the position number preceded by the native residue and followed by the substituted residue. Thus, thrombin with serine at position 205 replaced by alanine is denoted S205A.

Preferred Embodiments

In both the agonists and antagonists of groups (1)–(4) of the invention, some of the preferred embodiments of the amino acid sequences are those wherein the amino acid in the peptides are those encoded by the gene. Also included are those wherein one, two, three or more of the amino acid residues is replaced by one which is not encoded genetically.

In more detail, for these preferred embodiments, preferred embodiments of $AA_1$ and $AA_2$ are leu, val, or ile; especially preferred is leu. Preferred embodiments of $AA_3$ and $AA_8$ are arg or lys; especially preferred are embodiments wherein $AA_3$ is arg and $AA_8$ is lys. Preferred embodiments for $AA_4$ and $AA_6$ are gln or asn, and especially asn. Preferred embodiments for $AA_7$ and $AA_{10}$ are asp or glu; particularly preferred are embodiments wherein $AA_7$ is asp and $AA_{10}$ is glu. A preferred embodiment for $AA_{12}$ is phenylalanine, and of $AA_9$ is tyrosine.

Preferred acyl groups are of the formula RCO— wherein R represents a straight or branched chain alkyl of 1–6C. Acetyl is particularly preferred.

In all of the peptides of the invention, one or more amide linkages (—CO—NH—) may optionally be replaced with another linkage which is an isostere such as —CH$_2$NH—, —CH$_2$S—, —CH$_2$CH$_2$, —CH=CH— (cis and trans), —COCH$_2$—, —CH(OH)CH$_2$— and —CH$_2$SO—. This replacement can be made by methods known in the art. The following references describe preparation of peptide analogs which include these alternative-linking moieties: Spatola, A. F., *Vega Data* (March 1983), Vol. 1, Issue 3, "Peptide Backbone Modifications" (general review); Spatola, A. F., in "Chemistry and Biochemistry of Amino Acids Peptides and Proteins," B. Weinstein, eds., Marcel Dekker, New York, p. 267 (1983) (general review); Morley, J. S., *Trends Pharm Sci* (1980) pp. 463–468 (general review); Hudson, D., et al., *Int J Pept Prot Res* (1979) 14: 177–185 (—CH$_2$NH—, —CH$_2$CH$_2$—); Spatola, A. F., et al., *Life Sci* (1986) 38: 1243–1249 (—CH$_2$—S); Hann, M. M., *J Chem Soc Perkin Trans I* (1982) 307–314 (—CH—CH—, cis and trans); Almguist, R. G., et al., *J Med Chem* (1980) 23: 1392–1398 (—COCH$_2$—); Jennings-White, C., et al., *Tetrahedron Lett* (1982) 23: 2533 (—COCH$_2$—); Szelke, M., et al., European Application EP 45665 (1982) CA: 97: 39405 (1982) (—CH(OH)CH$_2$—); Holladay, M. W., et al., *Tetrahedron Lett* (1983) 24: 4401–4404 (—C(OH)CH$_2$—); and Hruby, V. J., *Life Sci* (1982) 31: 189–199 (—CH$_2$—S—).

Preparation of Peptide Agonists and Antagonists

The peptide agonists and antagonists of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Recombinant Production of Thrombin Receptor

The invention provides recombinant materials for the production of thrombin receptor for display on the surface of recombinant cells. Production of the receptor using these recombinant methods provides a useful diagnostic reagent either to determine the level of thrombin in biological samples or, more importantly, as a reagent to screen candidate substances which affect thrombin activity.

For this recombinant production, a DNA sequence encoding the thrombin receptor, as set forth in FIG. 1, or its degenerate analogs is prepared either by retrieval of the native sequence, as set forth below, or by using substantial portions of the known native sequence as probe, or can be synthesized de novo using standard procedures. The DNA is ligated into expression vectors suitable for the desired transformed host and transformed into compatible cells. The cells are cultured under conditions which favor the expression of the thrombin receptor encoding gene and the cells displaying the receptor on the surface harvested.

Use of Recombinant Thrombin Receptor as a Diagnostic and Screening Tool

The availability of the recombinant DNA encoding thrombin receptor permits expression of the receptor on host cell surfaces, thus making the cells available as a tool for evaluating the ability of candidate agonists or antagonists to bind to receptor.

In one type of easily conducted assay, competition of a candidate antagonist for binding to the receptor with either labeled thrombin, a thrombin agonist or known binding antagonist can be tested. The labeled substance known to bind the receptor can, of course, be a synthetic peptide. Varying concentrations of the candidate are supplied along with a constant concentration of labeled thrombin, thrombin agonist, or antagonist, and the inhibition of a binding of label to the receptor can be evaluated using known techniques.

In a somewhat more sophisticated approach, the effect of candidate compounds on thrombin-induced responses can be measured in the cells recombinantly expressing the thrombin receptor as described below. Assay systems for the effect of thrombin on these cells include calcium mobilization and voltage clamp which are further described in detail hereinbelow. Other suitable endpoints include thrombin-induced phosphoinositol turnover and inhibition of adenyl cyclase. These assays permit an assessment of the effect of the candidate antagonist on the receptor activity rather than simply ability to bind to thrombin.

Diagnosis of Cardiovascular Disease

In one embodiment, the availability of the recombinant thrombin receptor protein permits production of antibodies which are immunospecific to the activated form of the receptor which can then be used for diagnostic imaging of activated receptors in vivo. These antibodies are produced either to the activated form of the receptor produced recombinantly, or to the peptide representing the "new amino terminal" peptide described in Example 2 below. The resulting antibodies, or the immunospecific fragments thereof, such as the Fab, Fab', Fab'$_2$ fragments are then conjugated to labels which are detected by known methods, such as radiolabels including technetium[99] and indium[111] or other radioactive labels as is known in the art. When injected in vivo, these antibodies home to the sites of activated receptor, thus permitting localization of problem areas which are subject to thrombosis.

In another embodiment of diagnosis, the presence of the activation peptide in body fluids can be detected and measured. Antibodies are made to the activation peptide as described above and can be employed in standard ELISA or RIA assays to detect excess amounts of the activation peptide in, for example, urine.

Utility and Administration of Antagonists

The antagonists of the invention are useful therapeutically in the treatment of abrupt closure or restenosis in the context of angioplasty; in the treatment of unstable angina; and in the treatment of myocardial infarction. The peptides of the invention which behave as antagonists are administered in conventional formulations for systemic administration as is known in the art. Typical such formulations may be found, for example, in *Remington's Pharmaceutical Sciences*, Mack Publishing Co., Easton Pa., latest edition.

Preferred forms of systemic administration of peptides include injection, typically by intravenous injection. Other injection routes, such as subcutaneous, intramuscular, or intraperitoneal, can also be used. More recently, alternative means for systemic administration of peptides have been devised which include transmucosal and transdermal administration using penetrants such as bile salts or fusidic acids or other detergents. In addition, if properly formulated in enteric or encapsulated formulations, oral administration may also be possible.

The dosage range required depends on the choice of antagonist, the route of administration, the nature of the formulation, the nature of the patient's illness, and the judgment of the attending physician. Suitable dosage ranges, however, are in the range of 0.1–100 µg/kg of subject. Wide variations in the needed dosage, however, are to be expected in view of the variety of antagonists available and the differing efficiencies of various routes of administration. For example, oral administration would be expected to require higher dosages than administration by intravenous injection. Variations in these dosage levels can be adjusted using standard empirical routines for optimization as is well understood in the art.

The agonists of the invention are useful in the treatment of wounds and in other contexts wherein fibroblast proliferation is useful. Administration of these compounds is generally topical and/or localized, in the form of salves, pastes, gels and the like.

Assay Systems

Various assay systems may be used to measure the interaction of thrombin with its receptor and the affect of various candidate agonists and antagonists thereon. The role of the thrombin receptor and thrombin in platelet aggregation can be measured directly by aggregometry or the effect on blood clotting involving fibrin may be used as an index. In addition, ATP uptake by platelets can be measured. Also useful as a measure of thrombin receptor activation are assays utilizing calcium mobilization or voltage clamp assay in cell's known to express the thrombin receptor. These latter assays are especially useful in recombinant cells expressing the thrombin receptor.

Platelet Aggregation: In this assay, washed human platelets are prepared by the method of Baenzinger, M. G., *Meth Enzymol* (1974) 31: 149–155, or as described by Charo, I. F., et al., *J Clin Invest* (1977) 63: 866–873. To induce aggregation, approximately 1–20 nM thrombin or $EC_{50}$ of an alternate agonist is used to stimulate aggregation in control reactions; the results are followed by lumiaggregometry. Candidate agonists at various concentrations may be used in place of thrombin to stimulate aggregation. Candidate inhibitors are added to the reaction mixture in addition to the thrombin in order to assess their ability to prevent aggregation.

Washed platelets are suspended in modified Tyrode's buffer, pH 7.4 with 2 mM magnesium and 1 mM calcium at a concentration of $10^8$ platelets/ml. The thrombin or test compound is added in a small volume (about 20 µL) in 600 mM NaCl, 10 mM MES pH 6.0, 0.5% PEG 6000 buffer and incubated for 15 minutes at 37° C. with a platelet suspension.

Platelet Activation/ATP Secretion: Platelets prepared as above in 480 µl of suspension are added to 20 µl of phosphate buffered saline containing sufficient thrombin to give a final concentration of about 10 nM, or an alternate agonist is added at its $EC_{50}$. About 20 μl Chromolume® reagent (Chronolog Corporation, Havertown, Pa.) is added. In addition to measuring aggregation, ATP secretion is assessed. These results quantitated independently measuring changes in luminescence and light transmittance in a chronolog dual channel lumiaggregometer (Chronolog Corporation). Platelet ATP secretion is measured in a lumiaggregometer as luminescence signal. Candidate antagonists which putatively interact with thrombin are preincubated with the thrombin in 20 μl PBS at room temperature for 5 minutes before addition to the platelets. Preincubation is not necessary for testing agonists or antagonists which interact directly with the receptor.

Platelet Aggregation Assay Using Microtiter Plates: Thrombin- or agonist-mediated platelet aggregation as measured with washed platelets in 96-well microtiter plates was performed as described (Fratantoni, J. C. et al., *Am J Clin Pathol* (1990) 94: 613–617). The ability of hybridoma supernatants, purified MoAbs or peptide antagonists to block the thrombin receptor was assessed in this assay with various concentrations of antibodies or antagonists.

Fibrinogen Clotting Assay: Fibrinogen clotting reactions are performed in a total volume of 300 μl in 150 mM NaCl, 20 mM Tris, pH 7.4, 10 mM $CaCl_2$, 0.5% PEG 6000 at 37° C. and a final fibrinogen concentration of 3.3 mg/ml. Thrombin at 5 nM gives an approximately 10 second clotting time as measured by a standard Fibrosystem® coagulation timer (Fisher Scientific, Springfield, N.J.).

As described above, candidate agonists are used in place of the thrombin to stimulate fibrant formation; antagonists or inhibitors are added along with the thrombin to test their ability to prevent clot formation.

Calcium Mobilization: Agonist-induced increases in $^{45}Ca$ release by oocytes expressing cRNA encoding thrombin receptor were assessed by published techniques (Williams, J. A., et al., *Proc Natl Acad Sci USA* (1988) 85: 4939–4943). Briefly, intracellular calcium pools are labeled by incubating groups of 30 oocytes in 300 μl calcium-free MBSH containing 50 μCi $^{45}CACl_2$ (10–40 mCi/mg Ca; Amersham) for 4 hours at RT. The labeled oocytes are washed, then incubated in MBSH II without antibiotics for 90 minutes. Groups of 5 oocytes are selected and placed in individual wells in a 24-well tissue culture plate (Falcon 3047) containing 0.5 ml/well MBSH II without antibiotics. This medium is removed and replaced with fresh medium every 10 minutes; the harvested medium is analyzed by scintillation counting to determine $^{45}Ca$ released by the oocytes during each 10-minute incubation. The 10-minute incubations are continued until a stable baseline of $^{45}Ca$ release per unit time is achieved. Two additional 10-minute collections are obtained, then test medium including agonist is added and agonist-induced $^{45}Ca$ release determined.

Voltage Clamp: Agonist-induced inward chloride currents are measured in voltage-clamped oocytes expressing thrombin receptor encoding cRNA essentially as previously described (Julius, D., et al. *Science* (1988) 241: 558–563) except that the single electrode voltage-clamp technique is employed.

The following examples are intended to illustrate but not to limit the invention.

EXAMPLE 1

Preparation of cDNA Encoding Thrombin Receptor

In summary, the human cell lines HEL (Papayannopoulou, T., et al., *J Clin Invest* (1987) 79: 859–866) and Dami cells (Greenberg, S. M., et al., *Blood* (1988) 72: 1968–1977) were stimulated with phorbol 12-myristate 13-acetate (PMA) before isolation of mRNA for microinjection into Xenopus oocytes. The oocytes which had been injected with these mRNA samples were then assayed for cellular calcium mobilization to detect those eggs which were expressing the thrombin receptor encoded by the RNA at their surfaces. After size selection of the mRNA, a 40 kb mRNA fraction was used for preparation of a cDNA library. The library was assayed by conversion of plasmid DNA, cloned in *E. coli*, into capped cRNA in an in vitro system, and injection of the capped cRNA into the oocytes. An insert in a positive clone was sequenced to obtain the cDNA and deduced amino acid sequence shown in FIG. 1.

In more detail, Xenopus oocytes were harvested from female *Xenopus laevis* and processed using published techniques (Coleman, A., in Hames, B. D., and Higgins, S. J., eds., *Transcription and Translation: A Practical Approach*, IRL Press, pp. 271–302; Williams, J. A., et al., *Proc Natl Acad Sci USA* (1988) 85: 4939–4943). To remove follicular cells, oocytes were incubated for 4 hours at RT with 1 mg/ml Sigma type II collagenase in modified Barth's solution (MBSH) without calcium, then washed and incubated overnight at 18° C. in MBSH II (MBSH containing 1 mg/ml bovine serum albumin, 1 mg/ml Ficoll, 100 U/ml penicillin, 100 μl/ml streptomycin, and 50 μg/ml gentamicin).

Dumont stage V oocytes were selected and microinjected with 50 ml of the mRNA to be tested (1 μg/μl in 10 mM Hepes, pH 7.0); 5 ng of cRNA transcribed from a cDNA encoding a secreted form of alkaline phosphatase (generously provided by Dr. S. Udenfriend) was coinjected with all mRNA or cRNA samples as an internal standard for selection of healthy oocytes (Tate, S. S., et al., *FASEB J* (1990) 4: 227–231). Microinjected oocytes were cultured for 48 h at 18° C. in MBSH II in individual wells in 96-well culture plates; the oocyte-conditioned medium was then assayed for alkaline phosphatase activity as described (Tate et al., (supra)) and the "best-expressing" oocytes were selected for functional assays.

Cytoplasmic and poly A+ RNA were prepared from HEL and Dami cells by standard techniques (Sambrook, J., et al., *Molecular Cloning*, 1989, Cold Spring Harbor Laboratory Press, New York). Poly A+ RNA was fractionated by size by centrifugation through a 10–30% sucrose density gradient exactly as described by Sumikawa, K., et al., *Nucl Acids Res* (1982) 10: 5809–5822. Aliquots of each gradient fraction were analyzed for size by glyoxal gel electrophoresis. The remainder of each fraction was twice ethanol precipitated, and RNA dissolved at 1 μg/μl in 10 mM Hepes, pH 7.0. Aliquots of each fraction were assayed in the oocyte system described above for thrombin receptor activity.

A size-selected cDNA library was synthesized from the 4 kb mRNA fraction enriched for thrombin receptor activity using the method of Gubler and Hoffman (*Gene* (1983) 25: 263–269). After ligation to BstXI adapters (Aruffo and Seed, *Proc Natl Acad Sci USA* (1987) 84: 8573–8577), cDNAs of approximately 3.5 kb or greater were selected by acrylamide gel electrophoresis prior to ligation into the cloning vector pFROG. The pFROG vector was derived from pCDM6XL (a pH 4M-derived vector (Aruffo and Seed (supra)) generously provided by C. Spencer Yost, UCSF) by adding a linker inserting a restriction site for the rare cutter MluI next to the NotI site. pFROG placed the cDNA under the transcriptional control of the SP6 RNA polymerase promoter and directed the synthesis of a hybrid mRNA containing the 5'-untranslated region of Xenopus globin followed by message encoded by the cDNA insert.

The *E. coli* strain MC1061 was transformed with the cDNA library by electroporation, and plated in 50 pools of 20,000 clones per pool. MC1061 carrying a model clone, serotonin 1c receptor cDNA in pFROG, was included at one clone per 2000 as an internal standard. Plasmid DNA was prepared from each pool and made linear by digestion with NotI; capped cRNA was produced in vitro (Krieg and Melton, *Meth Enzymol* (1987) 155: 397–415) and assayed for thrombin receptor activity in the oocyte system as described above.

All pools were screened using both the voltage clamp and $^{45}Ca$ release assay. Of the first five pools screened, all showed some thrombin receptor activity; in the $^{45}Ca$ release assay, thrombin-induced increases in $^{45}Ca$ release ranged from two- to six-fold. The most active pool was replated at approximately 2000 clones per plate and rescreened in the oocyte system. Two of 10 pools screened were positive for thrombin receptor activity. The most active of these was replated at 300 clones per plate and the pools rescreened. By progressive selection and subdivision of active pools, a single clone was identified.

The 3480-nucleotide cDNA insert was subcloned into the XhoI site of pBluescript. Restriction fragments of the insert were subcloned into M13. The cDNA sequence was determined twice in each direction (three times for the coding region) by dideoxy sequencing. The results are shown in FIG. 1.

FIG. 1 shows both the nucleotide sequence and the deduced amino acid sequence for the thrombin receptor protein. Hydrophobic regions, including a putative signal sequence and seven transmembrane spans are overlined. After processing of the signal sequence by signal peptidase, it is probable that additional processing by proline-directed arginyl cleavage occurs between the arginines at positions 27 and 28, which is marked on the Figure. Thus, the amino terminus of the mature protein begins RPESK .... Possible asparagine-linked glycosylation sites are underlined, and consensus polyadenylation regions are in bold. The putative thrombin receptor cleavage site at position $R_{41}/S_{42}$ is also marked.

As set forth above, FIG. 2 provides a diagram of the disposition of the thrombin receptor in the cell membrane. As shown in FIG. 2, the amino terminal extracellular extension of the intact and unactivated thrombin receptor is cleaved by thrombin, exposing a new amino terminus and releasing the short receptor fragment designated the "activation peptide" herein. The newly exposed amino terminus then functions as an agonist, binding to an as yet undefined region of the thrombin receptor and activating it. The thrombin receptor is thus activated by a mechanism analogous to zymogen-enzyme conversion. Thus, the thrombin receptor, like other receptors which contain seven transmembrane regions, contains its own ligand with the N-terminus in the native form of $S_{42}/F_{43}$.

Figure 3:
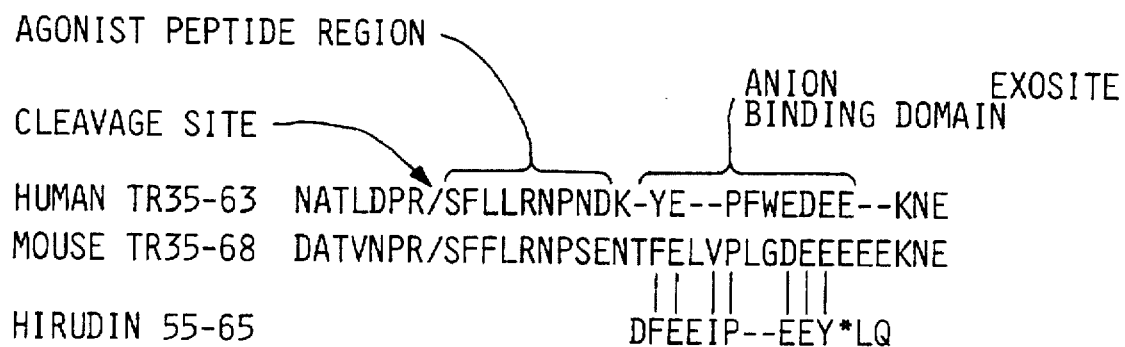
FIG. 3 shows a comparison of amino acid sequences for the cleavage site and exosite binding domains deduced from the cDNA encoding human thrombin receptor and from the cDNA encoding murine thrombin receptor. Also shown is the relevant portion of the hirudin sequence SEQ ID NO: 221, SEQ ID NO: 222 and SEQ ID NO: 223.

The availability of the human cDNA encoding thrombin receptor permitted the retrieval of the corresponding murine form. A high degree of homology is shown at the cleavage site and anion exosite binding domain. The homology of these sequences with each other and with the anion exosite binding domain of hirudin is shown in FIG. 3.

EXAMPLE 2

Synthesis of Ser-Phe-Leu-Leu-Arg-Asn-NH$_2$ (SEQ ID NO: 105)

Starting with paramethylbenzhydrylamine resin HCl (0.5 mmol synthesis, 0.77 meq/g, Applied Biosystems, Foster City, Calif.) was subjected to neutralization with diisopropylethylamine (DIEA) in N-methylpyrolidinone (NMP), followed by washings and addition of the required amino acids coupled as 1-hydroxybenzotriazole esters and introduced in order using an Applied Biosystems 431A peptide synthesizer. The Boc-amino acids had the following sidechain protection: Ser (OBzl) and Arg (Tos). Cleavage of the completed peptide resin was achieved with HF/anisole/methylethylsulfide (56/6/1 (v/v)) to afford the crude peptide which was purified by $C_{18}$ reversed-phase liquid chromatography using a gradient of acetonitrile in water containing 0.1% trifluoroacetic acid (TFA).

EXAMPLE 3

Agonist Activity of a "New Amino-Terminal" Peptide on Oocytes Expressing Wild-Type and Mutant Thrombin Receptor cRNA Oocytes were microinjected with 5 ng wild-type thrombin receptor cRNA (WT) or with 5 ng cRNA encoding a mutant thrombin receptor with the amino acid substitution R41A (R41A). The notation is analogous to that for thrombin as set forth above-alanine replaces arginine at position 41. Uninjected oocytes or oocytes expressing thrombin receptor cRNAs were then cultured for 48 hr and thrombin or peptide-induced $^{45}Ca$ release determined as described above. Candidate agonists were added at saturating concentrations: thrombin at 250 pM and the "new amino-terminal" peptide SEQ ID NO: 106 (SEQ ID NO: 109 peptide) at 25 µM. The control peptide SEQ ID NO: 107 (SEQ ID NO: 108 peptide) was added at 100 µM and elicited no response. The data shown in Table 1 represent the mean ±SEM of three replicate determinations; these results are representative of those obtained in three or four separate experiments.

TABLE 1

| Receptor | Agonist | Fold increase in $^{45}Ca$ |
|---|---|---|
| WT | Thrombin | 26 |
| WT | SEQ ID NO: 109 peptide 40 µM | 32 |
| WT | SEQ ID NO: 109 peptide 200 µM | 42 |
| R41A | Thrombin | 0 |
| R41A | SEQ ID NO: 109 peptide 200 µM | 53 |

The agonist SFLL peptide has no activity on uninjected oocytes (not shown). Qualitatively identical results were obtained when agonist-induced inward current in voltage-clamped oocytes was used as an endpoint rather than agonist-induced $^{45}Ca$ release.

EXAMPLE 4

Agonist Function of the "New Amino-Terminal" Peptide for Platelet Secretion and Aggregation and Mitogenic Effects Washed human platelets were prepared as described by Baenzinger, N. G., *Meth Enz* (1974) 31: 149–155; and Charo, I. F., et al., *J Clin Invest* (1977) 63: 866–873. Agonist-induced responses were assessed as described above.

Figure 4A:
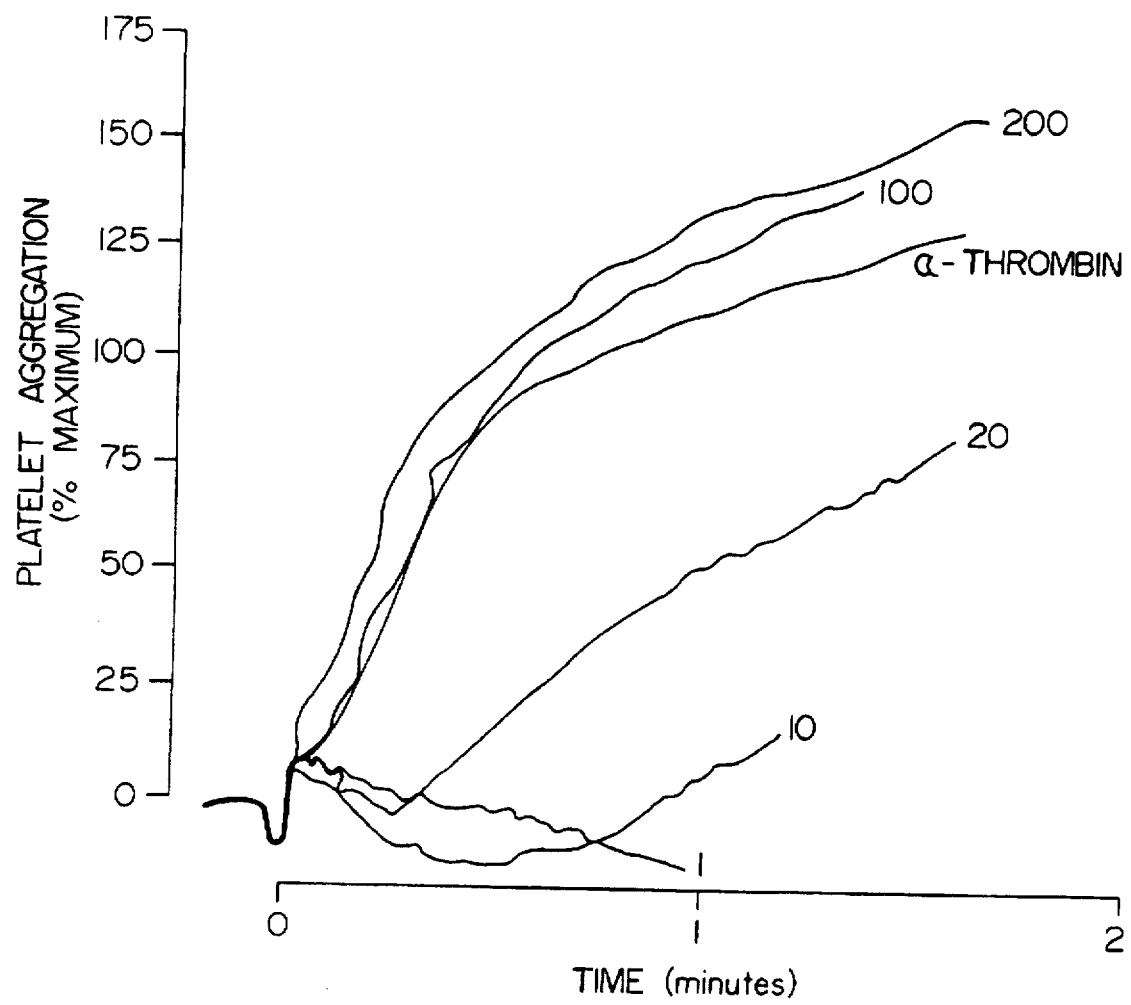

Platelet aggregation in response to 1, 10, 20, 100 or 200 µM peptide SEQ ID NO: 106 "SFLL" peptide or to 20 nM thrombin was measured in a lumiaggregometer, and the results are shown in FIG. 4A.

Platelet ATP secretion in response to the indicated final concentrations of "new amino-terminal" peptide was also followed by lumiaggregometry, and the results are shown in FIG. 4B.

The data shown in FIG. 4 are raw tracings representative of aggregation or secretion responses obtained in triplicate for each agonist concentration, and are representative of results obtained in more than five separate experiments. 100% aggregation is arbitrarily defined as that occurring in response to a saturating concentration of thrombin at one minute. 100% secretion is arbitrarily defined as the maximal response occurring in response to a saturating concentration of thrombin. The "new amino terminal" peptide is comparably active to 20 µM thrombin at concentrations of 100 µM in both assays as shown in the figure. The control peptides SEQ ID NO: 107 and SEQ ID NO: 110 were both without activity at concentrations as high as 200 µM (not shown).

In an additional determination, the mitogenic effects of the agonist peptide were demonstrated using CCL-39 cells. The fibroblast cell line CCL-39 was made quiescent in serum-free medium and then treated for 48 hours with the candidate agonist in the presence of tritiated thymidine. The incorporation of label into DNA was then determined as TCA-insoluble activity, shown as cpm in FIG. 5 using standard techniques. The data shown in the figure represent the mean of six replicate determinations plus or minus 95% confidence.

The agonists shown in the figure were:

None (serum-free);

10% fetal bovine serum (10% FCS);

100 nM α-thrombin (a-T);

1, 10 or 100 µM agonist peptide of the sequence SEQ ID NO: 106 (NTP);

100 µM "scrambled" agonist peptide, which is the foregoing with the N-terminus scrambled to FS (SEQ ID NO: 108).

Figure 5:
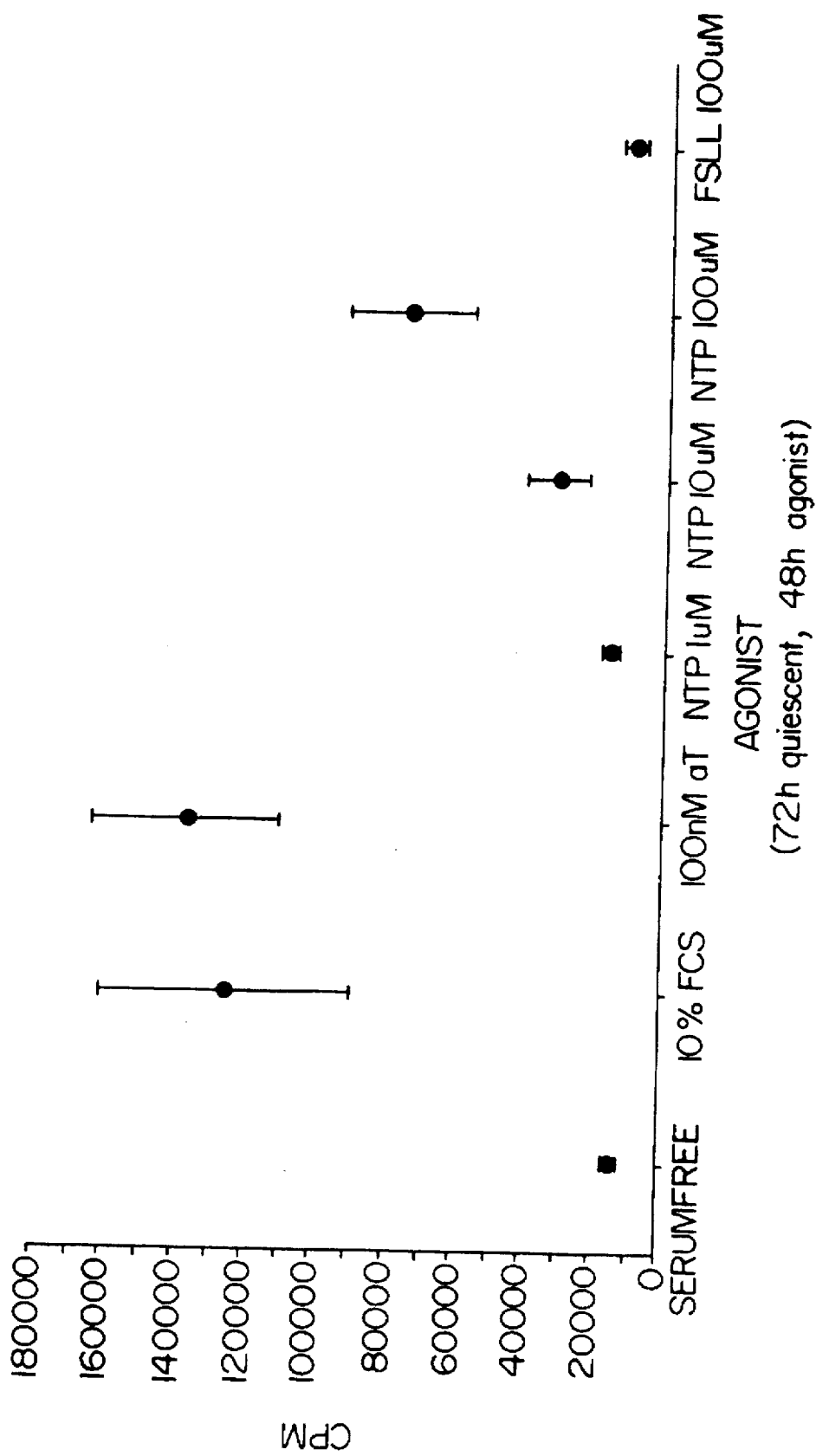
FIG. 5 shows the mitogenic effect of an agonist peptide of the invention on fibroblasts.

As shown in FIG. 5, the NTP at 100 µM gives significant stimulation of growth. Merely switching the positions of the first two residues of the agonist caused loss of activity. Thus, the agonist peptide not only simulates platelet aggregation, but also is useful in stimulating fibroblast proliferation, which is useful in wound-healing applications.

Platelet Aggregation Agonists:

Using the platelet aggregation assay described above, the concentration of various peptides required to elicit a 50% maximal aggregation was determined. The values obtained, shown as $EC_{50}$, are shown in Table 2 in micromolar units.

TABLE 2

| Agonist Peptides | |
|---|---|
| Peptide | $EC_{50}$ (µM) |
| 1. SEQ ID NO: 111 | 6.6 |
| 2. SEQ ID NO: 112 | 6.3 |
| 3. SEQ ID NO: 113 | 7.6 |
| 4. SEQ ID NO: 114 | 4.5 |
| 5. SEQ ID NO: 115 | 1.6 |
| 6. SEQ ID NO: 116 | 7.5 |
| 7. SEQ ID NO: 117 | 146 |
| 8. SEQ ID NO: 118 | Inactive |
| 9. SEQ ID NO: 119 | 796 |
| 10. SEQ ID NO: 120 | Inactive |
| 11. SEQ ID NO: 121 | 920 |
| 12. SEQ ID NO: 122 | 237 |
| 13. SEQ ID NO: 123 | 366 |
| 14. SEQ ID NO: 124 | 1000 |
| 15. SEQ ID NO: 125 | Inactive |
| 16. SEQ ID NO: 126 | Inactive |
| 17. SEQ ID NO: 127 | Inactive |
| 18. SEQ ID NO: 128 | Inactive |
| 19. SEQ ID NO: 129 | WA |

TABLE 2-continued

| Agonist Peptides | |
|---|---|
| Peptide | $EC_{50}$ (µM) |
| 20. SEQ ID NO: 130 | 2000 |
| 21. SEQ ID NO: 131 | 1500 |
| 22. SEQ ID NO: 132 | WA |
| 23. SEQ ID NO: 133 | 850 |
| 24. [D-Ser] - FLLRNPNDKYE | 172 |
| 25. SEQ ID NO: 134 | 193.0 |
| 26. SEQ ID NO: 135 | 129.2 |
| 27. SEQ ID NO: 136 | 99 |
| 28. SEQ ID NO: 137 | 7.3 |
| 29. SEQ ID NO: 138 | 8.5 |
| 30. SEQ ID NO: 139 | 12.9 |
| 31. SEQ ID NO: 140 | Inactive |
| 32. S (D-Phe) LLRNPNDKYE | Inactive |
| 33. SEQ ID NO: 141 | Inactive |
| 34. SEQ ID NO: 142 | 288 |
| 35. SEQ ID NO: 143 | 250 |
| 36. SEQ ID NO: 144 | Inactive |
| 37. SEQ ID NO: 145 | Inactive |
| 38. SEQ ID NO: 146 | Inactive |
| 39. SEQ ID NO: 147 | 140 |
| 40. SEQ ID NO: 148 | 42 |
| 41. SEQ ID NO: 149 | 46 |
| 42. SEQ ID NO: 150 | 8 |
| 43. SEQ ID NO: 151 | 7.6 |
| 44. SF (D-Leu) LRNPNDKYE | Inactive |
| 45. SF (D-Ala) LR-$NH_2$ | Inactive |
| 46. SEQ ID NO: 152 | Inactive |
| 47. SEQ ID NO: 153 | Inactive |
| 48. SEQ ID NO: 154 | Inactive |
| 49. SEQ ID NO: 155 | >1000 |
| 50. SEQ ID NO: 156 | 40.5 |
| 51. SEQ ID NO: 157 | 20.7 |
| 52. SEQ ID NO: 158 | 24 |
| 53. SEQ ID NO: 159 | 3.4 |
| 54. SEQ ID NO: 160 | 1.5 |
| 55. SEQ ID NO: 161 | 6.7 |
| 56. SEQ ID NO: 162 | 22 |
| 57. SEQ ID NO: 163 | 95 |
| 58. SEQ ID NO: 164 | 7.4 |
| 59. SEQ ID NO: 165 | 4.9 |
| 60. SEQ ID NO: 166 | 5.9 |
| 61. SEQ ID NO: 167 | 1.5 |
| 62. SEQ ID NO: 168 | 1.3 |
| 63. SEQ ID NO: 169 | 11.3 |
| 64. SFL (D-Leu) RNPNDKYE | Inactive |
| 65. SEQ ID NO: 170 | Inactive |
| 66. SEQ ID NO: 171 | Inactive |
| 67. SEQ ID NO: 172 | Inactive |
| 68. SEQ ID NO: 173 | 146.4 |
| 69. SEQ ID NO: 174 | 61 |
| 70. SEQ ID NO: 175 | 20.5 |
| 71. SEQ ID NO: 176 | 17 |
| 72. SEQ ID NO: 177 | 1000 |
| 73. SEQ ID NO: 178 | 7.5 |
| 74. SEQ ID NO: 179 | 6.0 |
| 75. SEQ ID NO: 180 | 1.1 |
| 76. SEQ ID NO: 181 | 5.4 |
| 77. SEQ ID NO: 182 | Inactive |
| 78. SFLL (D-Arg) - $NH_2$ | 594 |
| 79. SEQ ID NO: 183 | 137 |
| 80. SEQ ID NO: 184 | 44.9 |
| 81. SEQ ID NO: 185 | 20.2 |
| 82. SEQ ID NO: 186 | 11.1 |
| 83. SEQ ID NO: 187 | 3.3 |
| 84. SEQ ID NO: 188 | 1.4 |
| 85. SEQ ID NO: 189 | 0.82 |

EXAMPLE 5

Figure 6:
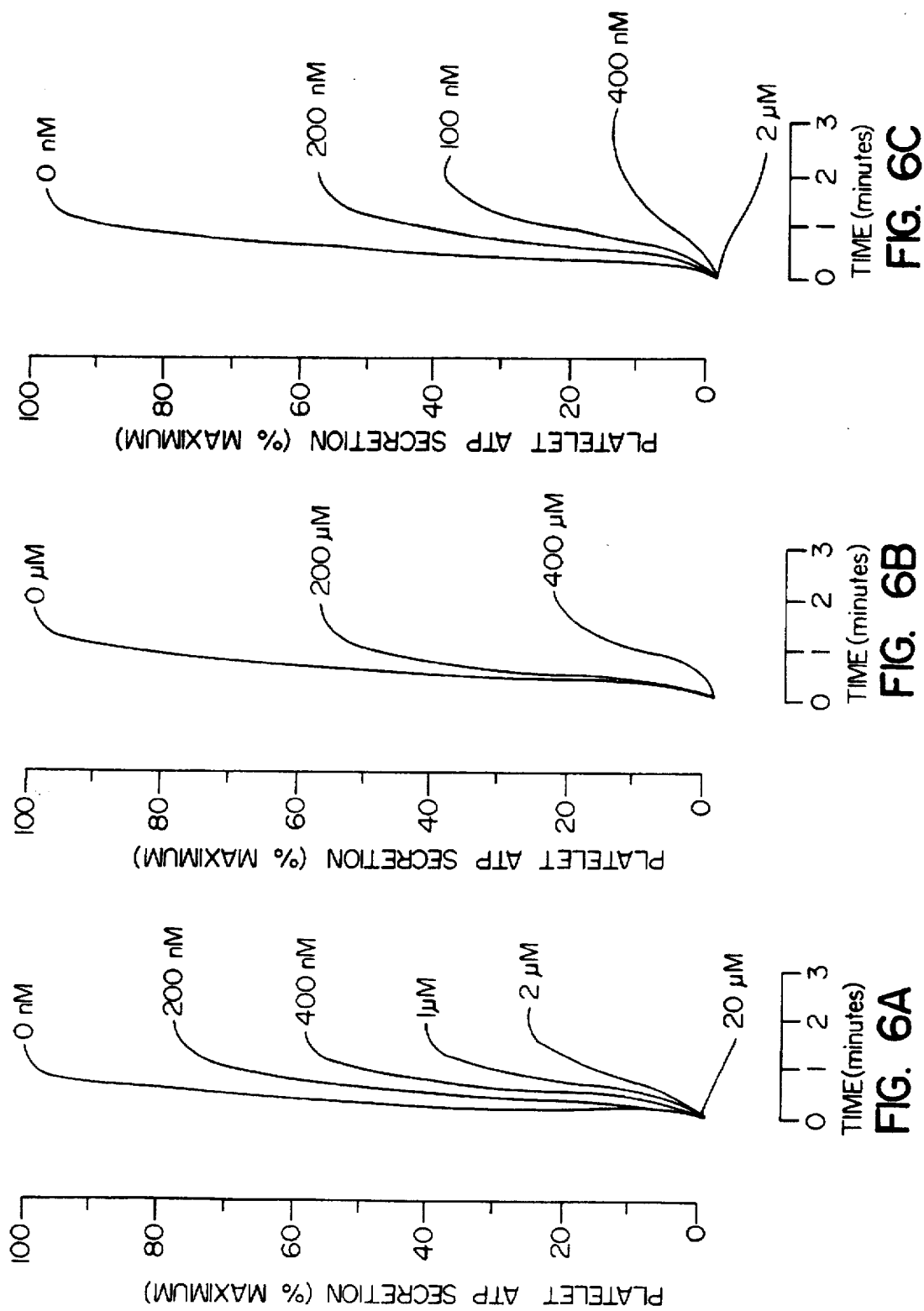
FIGS. 6A, 6B and 6C show the effects of three thrombin inhibitor peptides on thrombin-induced platelet activation.

Inhibition of Thrombin-Induced Platelet Activation by Thrombin Inhibitor Peptides Three antagonist peptides of the invention, SEQ ID NO: 74 (SEQ ID NO: 68 peptide), F⁺PRPFLLRNPNDKY EPF- WEDEEKNES (F†PRP peptide) and SEQ ID NO: 190 (shortened SEQ ID NO: 68 peptide), were tested for their ability to inhibit thrombin-induced platelet activation. Thrombin was incubated with the candidate inhibitory peptide for 5 minutes, then the mixture was added to washed platelets and platelet activation was followed as platelet ATP secretion by lumiaggregometry. The mixtures were added in a total volume of 20 µl phosphate buffered saline to 480 µl of platelets prepared and suspended as described in the description under the heading "Assays" hereinabove. Various concentrations of the candidate peptides were used. The results are shown in FIGS. 6A, 6B and 6C. The ATP secretion is expressed as a percentage of the mean luminescence signal generated by 10 nM thrombin in the absence of the candidate peptides; the figures shown are representative of the results of three replicate experiments.

FIG. 6A shows the results for the LDPRP peptide, which shows an $IC_{50}$ of approximately 500 mM. The LDPRP peptide contains sequences which are representative of both the cleavage site and the putative thrombin binding site. FIG. 6B shows the results obtained for the shortened SEQ ID NO: 68 peptide; the $IC_{50}$ is now approximately 200 µM.

However, as shown in FIG. 6C, the F†PRP peptide which contains an alternate form of the putative cleavage site as well as the putative binding site has an $IC_{50}$ of approximately 200 nM; this peptide is thus a more effective antagonist than either the SEQ ID NO: 68 peptide or its shortened form.

EXAMPLE 6

Preparation of Thrombin Receptor Antagonist Peptide: Synthesis of Mpr-Phe-Cha-Cha-Arg-Asn-Pro-SEQ ID NO: 51

Starting with N-α-Boc-ε-(Cl-CBZ)-Lys-O-Pam-Resin (0.5 mmol, 0.70 meq/g, Applied Biosystems, Foster City, Calif.), the Boc group was removed with TFA, neutralized, washed and the required amino acids were added in sequence by coupling as 1-hydroxybenzotriazole esters employing an Applied Biosystems 431A peptide synthesizer. The peptide was cleaved from the resin and purified by reversed-phase chromatography as described in Example 3.

Candidate peptides analogously synthesized were tested in the platelet activation/aggregation assays described above and added at various concentrations in the presence of thrombin. The concentration which resulted in 50% inhibition of activation or aggregation was designated the $IC_{50}$ and is shown for the various peptides tested in Table 3 in micromolar units.

TABLE 3

| Antagonist Activity | |
|---|---|
| | $IC_{50}$ (µM) |
| 1. SEQ ID NO: 191 | 80 |
| 2. SEQ ID NO: 192 | 108 |
| 3. SEQ ID NO: 193 | 200–400 |
| 4. SEQ ID NO: 194 | 500–1000 |
| 5. SEQ ID NO: 195 | 500–1000 |
| 6. SEQ ID NO: 196 | 400 |
| 7. SEQ ID NO: 51 | 30 |
| 8. SEQ ID NO: 52 | 40 |
| 9. SEQ ID NO: 53 | 80 |
| 10. SEQ ID NO: 54 | 75 |
| 11. SEQ ID NO: 55 | 25 |
| 12. SEQ ID NO: 56 | 50 |

TABLE 3-continued

| Antagonist Activity | |
|---|---|
| | $IC_{50}$ (µM) |
| 13. SEQ ID NO: 57 | 100 |
| 14. SEQ ID NO: 58 | 40 |
| 15. SEQ ID NO: 59 | 20 |
| 16. SEQ ID NO: 197 | 100 |
| 17. SEQ ID NO: 60 | 5 |
| 18. SEQ ID NO: 61 | 75 |
| 19. SEQ ID NO: 62 | 75 |
| 20. SEQ ID NO: 198 | >100 |
| 21. SEQ ID NO: 63 | 50 |
| 22. SEQ ID NO: 64 | 10 |
| 23. SEQ ID NO: 65 | 50 |
| 24. SEQ ID NO: 199 | 500–1000 |
| 25. SEQ ID NO: 200 | 1000 |
| 26. SEQ ID NO: 201 | 500 |
| 27. SEQ ID NO: 202 | 1000 |
| 28. SEQ ID NO: 67 | 10 |
| 29. SEQ ID NO: 203 | 50 |
| 30. SEQ ID NO: 204 | 10 |

As shown in Table 3, substitution of the amino acid Cha for the leucine and Lys for Asn residues improves the antagonist activity.

EXAMPLE 7

Generation of Active-site Thrombin Mutants

Oligonucleotide-directed mutagenesis (Kunkel, T. A., et al., *Meth Enzymol* (1987) 154: 367–383) was used to generate the active-site residue substitutions S205A and D99N/S205A in a native prothrombin cDNA cloned into a Bluescript SK-plasmid vector system (Stratagene, La Jolla, Calif.). After confirmation by DNA sequencing, DNA coding for prothrombin with the desired mutation(s) in the thrombin active site as well as native prothrombin cDNA were subcloned into a pBJ1 expression vector (derived from pcDL-SRα296) (Takabe, Y., et al., *Mol Cell Biol* (1988) 8: 466–472) and cotransfected into dihydrofolate reductase (SEQ ID NO: 205)-minus CHO cells by lipofection (Felgner, P., et al., *Proc Natl Acad Sci USA* (1987) 84: 7413–7417) with a DHFR selection marker in pSV2D (Sabramani, S., et al., *Mol Cell Biol* (1981) 2: 854–864). Stable transfectants were isolated and gene amplification was accomplished in 80 nM methotrexate.

Recombinant prothrombin production was determined by ELISA and Western blots and the highest yielding clones were grown to confluence in a 24,000 cm² surface cell "factory" (Nunc, Inter Med, Naperville, Ill.) in MEM α-nucleoside-deficient medium with 80 nM methotrexate, 100 units/ml penicillin, 100 µg/ml streptomycin, 25 mM Hepes buffer, 5 µg/ml vitamin K, 0.2 mg/ml proline, and 10% dialyzed bovine calf serum. Upon reaching full confluence, all medium was removed, all growing surfaces washed six times with phosphate-buffered saline to remove contaminating bovine prothrombin and thrombin, and cells were grown in MEM α-nucleoside-deficient medium containing 100 units/ml penicillin, 100 µg/ml streptomycin, 25 mM Hepes buffer, 5 µg/ml vitamin K, 0.2 mg/ml proline, 1 µg/ml insulin and 5 µg/ml transferrin for 36–48 hours.

Conditioned medium was cleared of cellular debris by centrifugation and filtration, diluted 1:1 with water, made to 10 mM Tris-HCl, pH 7.4, and 20 mM citrate (final concentration) and stirred overnight at 4° C. with 1% (v/v) S-Sepharose. S-Sepharose beads were removed by centrifugation and the conditioned medium was refiltered and stirred overnight at 4° C. with 1% (v/v) Q-Sepharose. Q-Sepharose was then collected in a 10 ml column and eluted in 1 ml fractions with 600 mM NaCl, 10 mM Tris-HCl, pH 7.4, 0.5% PEG 6000 and positive fractions containing recombinant prothrombin identified by Western blot using anti-human thrombin antiserum.

Positive fractions were pooled, diluted to an estimated concentration of 100 µg/ml S205A mutant prothrombin in 150 mM NaCl, 10 mM Tris-HCl, pH 7.4, 0.5% PEG 6000 and treated for 1 hr with prothrombinase complex as previously described (Krishaswamy, S., et al., *J Biol Chem* (1987) 262: 3291–3299). pH was then changed to 7.0 with 1M HCl and the S205A or D99N/S205A mutant thrombin-containing solution was treated with an approximately 1,000-fold molar excess of (p-amidinophenyl)methanesulfonyl fluoride (APMSF) to inhibit Factor Xa and any bovine thrombin that might contaminate the preparation. APMSF is a serine-dependent irreversible thrombin antagonist that rapidly inactivates native thrombin at pH 7.0 but has a half-life of only $10^{-3}$ sec at pH 8.0. For this reason, the pH of the APMSF-treated mutant thrombin preparation was then changed to 8.0 for 15 min to eliminate all APMSF.

The mutant thrombin-containing solution was then changed to pH 6.0 by addition of 1N HCl and stirred overnight at 4° C. with 1% (v/v) S-Sepharose. The S-Sepharose was collected in a 10 ml column, washed with 150 mM NaCl, 10 mM MES, pH 6.0 and subsequently eluted with 600 mM NaCl, 10 mM MES, pH 6.0, 0.5% PEG 6000 in 1 ml fractions. Positive fractions were identified by Western blot with anti-human thrombin antiserum and the concentration and purity of recombinant S205A or D99N/S205A thrombin preparations were determined by Coomassie and silver-stained SDS-PAGE gels. The mutant thrombin preparations used in these studies appeared homogeneous on silver-stained SDS-PAGE gels.

EXAMPLE 8

Fibrinogen Clotting Assay

Fibrinogen clotting activity was measured by a standard Fibro System® coagulation timer (Fisher Scientific, Springfield, N.J.) as the time required for varying thrombin concentrations to generate a fibrin clot. All fibrinogen clotting reactions were performed in a total volume of 300 µl, in 150 mM NaCl, 20 mM Tris, pH 7.4, 10 mM CaCl$_2$, 0.5% PEG 6000 at 37° C. with a final fibrinogen concentration of 3.3 mg/ml. Both standard WT and recombinant WT showed identical curves—e.g., about 10 second clotting times at 5 mM. Neither S205A nor D99N/S205A were able to induce clotting.

EXAMPLE 9

Platelet ATP Secretion and Aggregation Studies

Washed platelets were prepared as described above and suspended in modified Tyrode' buffer, pH 7.4 with 2 mM magnesium and 1 mM calcium at a concentration of $10^8$ platelets/ml. All platelet studies were performed in a total volume of 500 µl with 20 µl Chromolume® reagent (Chronolog Corporation, Havertown, Pa.). Platelet ATP secretion and aggregation were quantitated independently by measuring changes in luminescence and light transmittance, respectively, in a Chronolog dual-channel lumiaggregometer (Chronolog Corporation, Havertown, Pa.). Platelets were stirred at 300 rpm to ensure rapid and uniform distribution of agonist.

Figure 7:
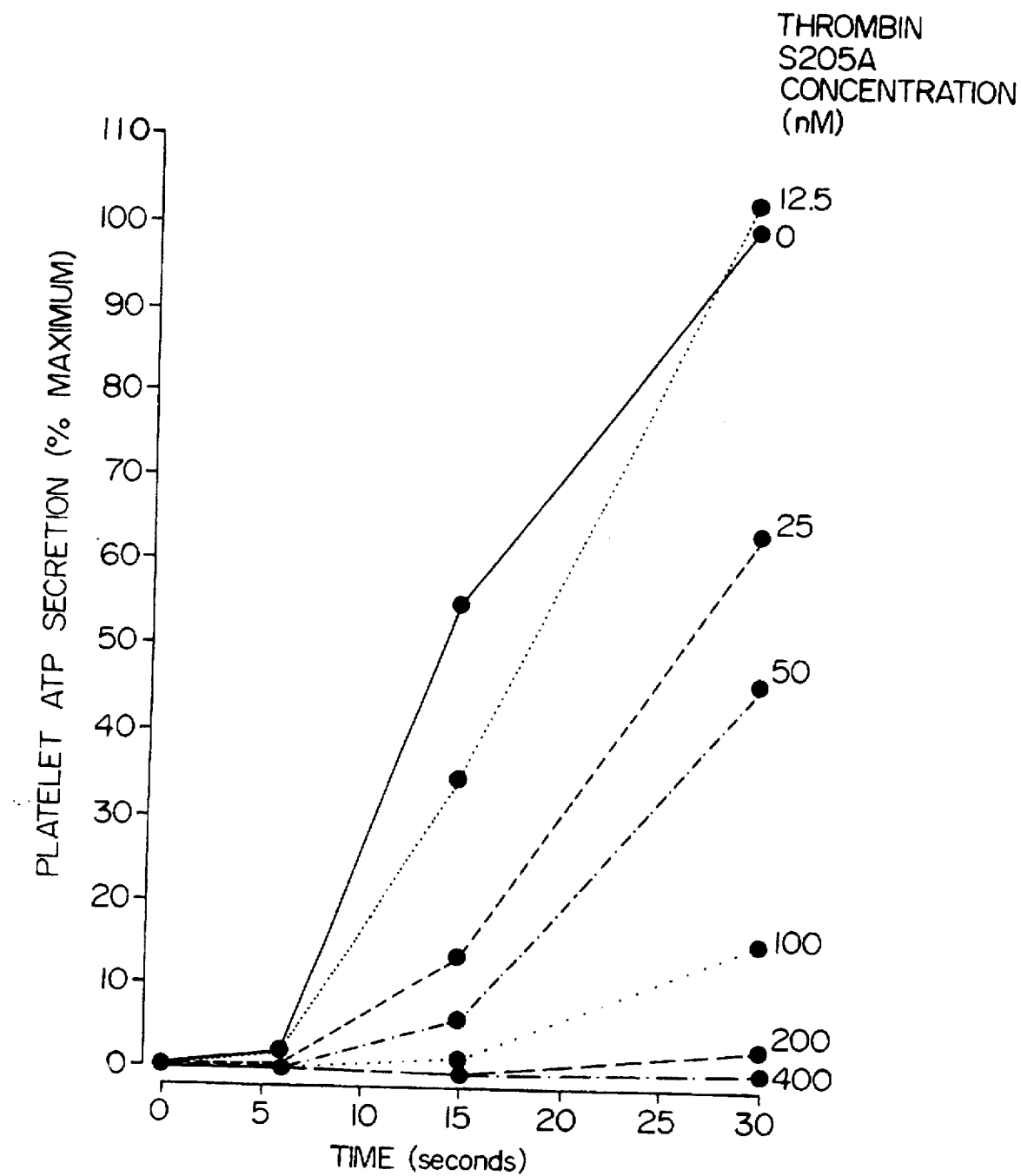
FIG. 7 shows the effect of mutant thrombin on platelet ATP secretion stimulated by thrombin.

500 µl of platelets were incubated for 15 minutes at 37° C. with 18 µl of diluted S205A stock in 600 mM NaCl, 10 mM MES, pH 6.0, 0.5% PEG 6000 buffer to give the desired final concentrations, or 18 µl of buffer alone and then challenged with native thrombin (1 mM final concentration). Platelet ATP secretion and aggregation were followed for 30 seconds after thrombin addition. Platelet ATP secretion data are expressed as a percentage of maximum, defined as the luminescence signal obtained 30 seconds after addition of 1 mM native thrombin to buffer-pretreated platelets. The results are shown in FIG. 7. Each point represents the mean of three replicate determinations, and are representative of three replicate experiments. As shown, increasing concentrations of S205A thrombin cause increasing inhibition of thrombin-induced platelet secretion. Similar results were obtained using the D99N/S205A mutant thrombin.

Figure 8:
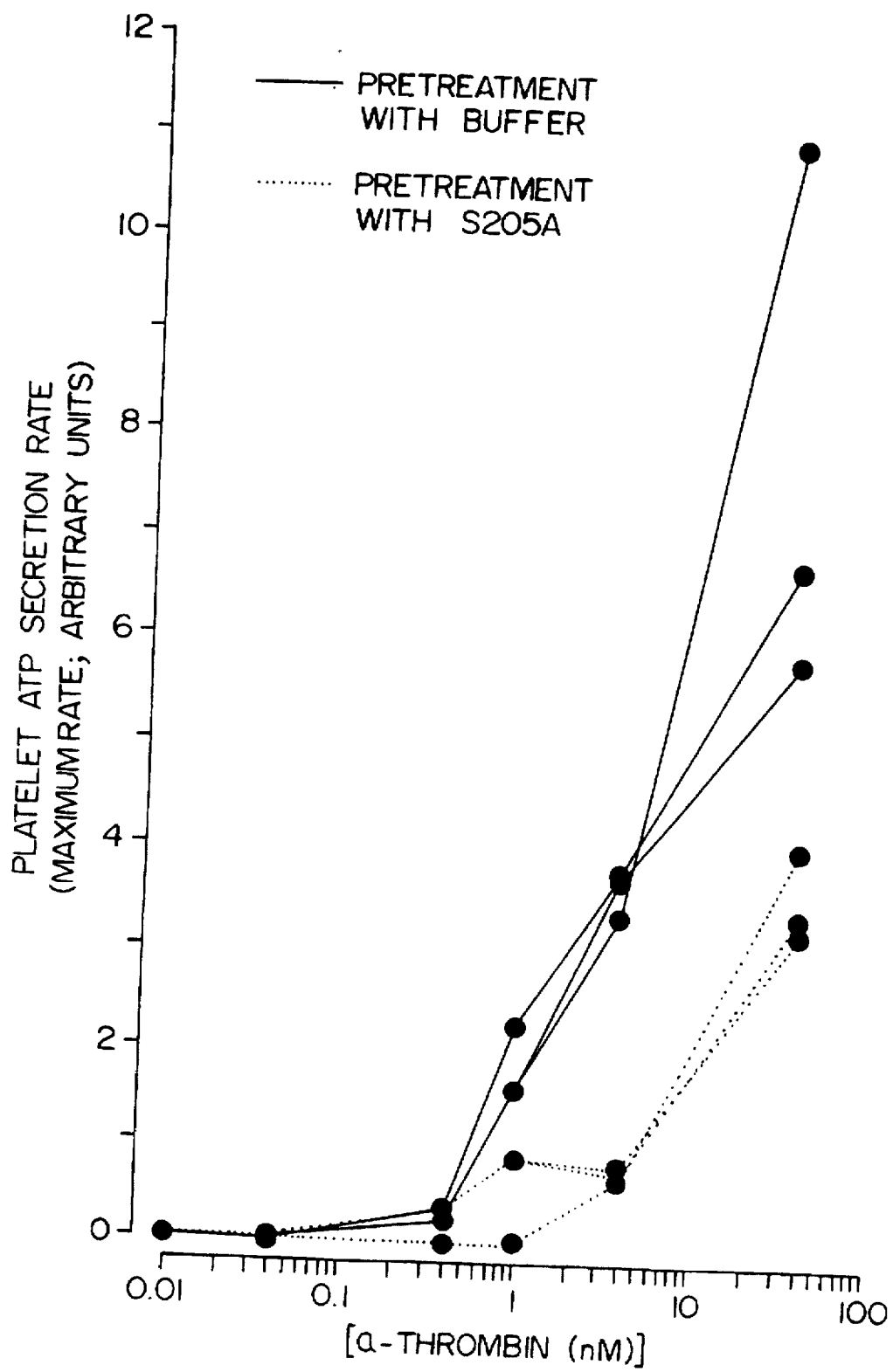
FIG. 8 shows the increase in thrombin needed to overcome inhibition of platelet ATP secretion by mutant thrombin.

In an additional determination it was shown (FIG. 8) that 400 nM S205A thrombin right-shifts the dose response of platelets to native thrombin by approximately 1 log. In this determination, 18 µl of S205A in 600 mM NaCl, 10 mM MES, pH 6.0, 0.5% PEG 6000 buffer to give a final S205A concentration of 400 nM) or an equal volume of buffer alone (solid lines) were incubated with 500 µl of platelets for 15 minutes at 37° C. Platelets were then stimulated with the indicated final concentrations of α-thrombin; platelet ATP secretion and aggregation were followed for 30 seconds after thrombin addition. The date shown reflect the maximum initial rate of platelet ATP secretion, specifically, the maximum rate of platelet ATP secretion occurring within 30 seconds of agonist addition and before any aggregation was detected. Thus, the platelet ATP secretion rates reported represent only agonist-induced and not aggregation-induced responses. Curves from three replicate experiments are shown in FIG. 5. One arbitrary unit corresponds to 33 pmoles of ATP released per second based on calibration with ATP standards.

Figure 9:
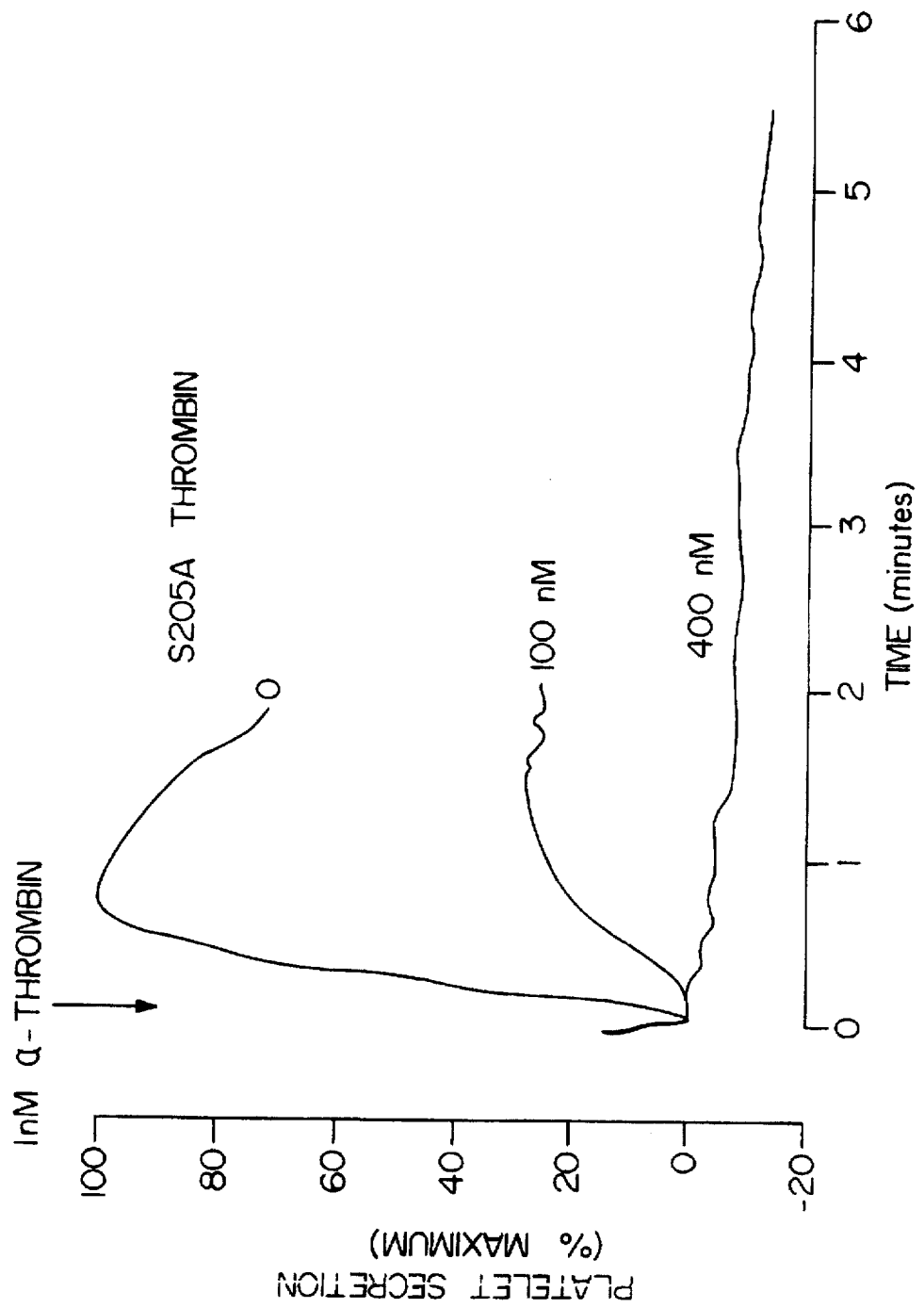
FIG. 9 shows the effect of thrombin on platelet ATP secretion by varying concentrations of thrombin mutant.

An additional experiment shows S205A thrombin inhibits the extent of native thrombin-induced platelet secretion. Platelets were preincubated with various concentrations of S205A, then stimulated with native thrombin (1 nM final concentration). To prevent aggregation-induced secretion, platelets in these experiments were suspended to a final concentration of $2 \times 10^7$ platelets/ml and were not stirred after the addition of native thrombin. Under these conditions, platelets did not aggregate but did secrete ATP in response to thrombin. Platelet secretion rate is expressed in arbitrary units as defined above. FIG. 9 shows tracings of platelet secretion curves, and are representative of the results obtained in three replicate experiments. The decrease in luminescence seen in the control curve (0 nM S205A thrombin) is characteristic of the assay and may represent end-product inhibition of luciferase.

However, S205A thrombin does not inhibit ATP secretion induced in platelets by stimulation with agonist peptide or a calcium ionophore.

EXAMPLE 10

Preparation of Antibodies

The peptides representing portions of the thrombin receptor amino terminal extension were used as immunogens to prepare polyclonal antisera and monoclonal antibodies.

The peptide SEQ ID NO: 206 (the cleavage site peptide) and the peptide SEQ ID NO: 207 (the anion exosite domain peptide) were used to generate antibodies. These antisera were tested as antagonists in the platelet activation assay described above. Both were effective in blocking activation. The polyclonal antibody preparation which is immunoreactive with the anion exosite domain peptide, Ab1047, was incubated with the platelets prior to the addition of thrombin at a 1 nM concentration was added. The inhibition was reversed by the addition of the peptide binding Ab1047, "peptide 360." Ab1047 at a 1:100 dilution almost completely inhibits the aggregation and activation of the platelets.

The peptide SEQ ID NO: 208 which contains the cleavage site and the proposed anion binding exosite of the receptor was also used to prepare potent receptor blocking monoclonal antibodies. This 40 residue peptide which has a Cys residue added at the carboxyl terminus of the native sequence was covalently attached to keyhole limpet hemocyanin (KLH) through the Cys residue using the thiol-specific reagent, m-maleimidobenzoyl-N-hydroxysulfosuccinimide ester (Sulfo-MBS, Pierce Chemical Co.). Following dialysis of the peptide-KLH conjugate, this material was used to immunize 3 BALB/c mice. Spleen cells obtained from each of the mice were fused with P3X cells to form a panel of hybridomas.

Supernatants from these hybridomas were assayed for their ability to crossreact with the native 40 residue peptide used for the immunization as well as 15-residue peptides which span the length of the 40-residue sequence in ELISA assays. Only IgG-specific clones were investigated further. Positive hybridomas were then tested for their ability to block thrombin-induced platelet aggregation in the microtiter plate shaker assay. Finally, positive hybridomas were reassayed with the ELISA assay using the 40-residue peptide under increasing salt washing conditions to choose 6 hybridomas with apparent high affinity. The 6 hybridomas were subcloned by limiting dilution resulting in clones 4-2, 10-6, 31-2, 33-1, 61-1, and 62-5.

Each of the clones was used for the production of ascites fluid by intraperitoneal injection of $1 \times 10^7$ cells/mouse cells. Ascites fluid rich in IgG was purified on protein A-sepharose, as the therapeutic potential of IgG is greater than IgM. The ability of each of these purified monoclonal antibodies to inhibit thrombin-induced platelet aggregation (using thrombin as agonist) was evaluated in washed platelets and is shown in Table 5. The $IC_{50}$s for these MoAbs ranged between 2.5–20 µg/ml of purified IgG.

TABLE 5

| Inhibition of Platelet Aggregation by Antibodies | |
|---|---|
| MoAb# | $IC_{50}$ (µg/ml Washed Platelets) |
| 4–2 | 10–20 |
| 10–6 | >20 |
| 31–2 | 2.5–5.0 |
| 33–1 | 2.5–4.0 |
| 61–1 | 2.5–5.0 |
| 62–5 | 10–20 |

We claim:

1. A peptide capable of activating thrombin receptor, which peptide is of the formula

$$AA_x\text{—}AA_y\text{—}(AA_i)_n\text{—}Z \qquad (1)$$

wherein $AA_x$ is a small amino acid or threonine, and $A_y$ is a neutral/nonpolar/aromatic amino acid residue or is a neutral/nonpolar/large/nonaromatic amino acid containing a cyclic portion;

wherein AA represents an amino acid residue and the subscript i is an integer which denotes the position of said amino acid residue downstream (N→C) of the $AA_y$ residue of formula (1), and n is an integer of 2–12 so that $(AA_i)_n$ represents $AA_1\text{-}AA_2$; $AA_1\text{-}AA_2\text{-}AA_3$; $AA_1\text{-}AA_2\text{-}AA_3\text{-}AA_4$; through $AA_1\text{-}AA_2\text{-}AA_3\text{-}AA_4\text{-}AA_5\text{-}AA_6\text{-}AA_7\text{-}AA_8\text{-}AA_9\text{-}AA_{10}\text{-}AA_{11}\text{-}AA_{12}$;

with the proviso that if n=2, Z must be of the formula NR'R' wherein at least one R' is alkyl (1–6C) containing at least one polar substituent;

$AA_1$ is a neutral or basic amino acid having a free α-amino group in the L-configuration;

$AA_2$ is a neutral or basic amino acid residue in the L-configuration;

$AA_4$–$AA_{12}$ are L-amino acid residues; and

Z is a substituent that does not prevent said activating with the proviso that said peptide is not a peptide selected from the group consisting of SFLLKNPNDKYEPF; SFLLRNPNDKYEP; SFLLRNPNDKYE; SFLLRNPNDKY; SFLLRNPNDK; SFLLRNPND; SFLLRNPN; SFLLRNP; SFLLRN; SFLLR; SFLL; and SFL, and the amidated forms thereof.

2. The peptide of claim 1 wherein $AA_X$ is a small amino acid selected from the group consisting of ser, ala, and gly or is thr.

3. The peptide of claim 1 wherein $AA_1$ and $AA_2$ are neutral/nonpolar/large amino acids.

4. The peptide of claim 3 wherein $AA_x$-$AA_y$ is selected from the group consisting of Gly-Phe, Ala-Phe, Ser-Phe, Thr-Phe, Gly-(pClPhe), Ala-p(ClPhe), Ser-(pClPhe), Thr-p (ClPhe), Gly-Thi, Ala-Thi, Ser-Thi and Thr-Thi.

5. The peptide of claim 3 wherein $AA_1$ and $AA_2$ are each independently Leu, Val, Ile, Cha, Phe, Nal or Tic.

6. The peptide of claim 1 wherein $AA_3$ and $AA_8$ are present and are each independently Arg, Lys, Har or Ala.

7. The peptide of claim 1 wherein Z comprises OR', or NR'R' wherein each R' is independently H or is a straight or branched chain alkyl of 1–6C, wherein each R' is unsubstituted or may be substituted with one or more substituents selected from the group consisting of —OR', —NR'R', and —NR'CNR'NR'R' wherein each R' is H or is a straight or branched chain alkyl of 1–6C.

8. The peptide of claim 1 which is selected from the group consisting of GFLLK; TFLLRNPNDK; S(pClPhe)LLR; S(Thi)LLR; SFFLK; SFFLRN; SF(Phg)LR; SFL(Nal)RN; SFL(Cha)R; SF(Cha)(Cha)KN; SF(Cha)(Cha)LKNPNDK; SFLLKN; SFLL(Har)N; SFLLKN; SFF(Cha)AN; SF(Cha)(Cha)RK; and the amidated forms thereof.

9. A pharmaceutical composition useful for platelet aggregation which comprises an effective amount of the peptide of claim 1 in admixture with at least one pharmaceutically acceptable excipient.

* * * * *

UNITED STATES PATENT AND TRADEMARK OFFICE
CERTIFICATE OF CORRECTION

PATENT NO. : 5,688,768
DATED : November 18, 1997
INVENTOR(S) : Shaun Coughlin and Robert Scarborough It is certified that error appears in the above-identified patent and that said Letters Patent is hereby corrected as shown below:

On the title page, item [73]

The Assignee should read -- THE REGENTS OF THE UNIVERSITY OF CALIFORNIA, Oakland, California and COR THERAPEUTICS, INC. South San Francisco, California.

Signed and Sealed this

Eighth Day of September, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 223

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

Arg Pro Glu Ser Lys Ala Thr Asn Ala Thr Leu Asp Pro Arg
1               5                   10

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

Tyr Glu Pro Phe Trp Glu Asp Glu Glu
1               5

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

Ser Phe Leu Leu Arg Asn Pro Asn Asp Lys Tyr Glu
1               5                   10

( 2 ) INFORMATION FOR SEQ ID NO:4:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( x i ) SEQUENCE DESCRIPTION: SEQ ID NO:4:

Ser Phe Leu Leu Arg Asn Pro Asn Asp Lys
1               5                   10

( 2 ) INFORMATION FOR SEQ ID NO:5:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( x i ) SEQUENCE DESCRIPTION: SEQ ID NO:5:

Ser Phe Leu Leu Arg Asn Pro Asn
1               5

( 2 ) INFORMATION FOR SEQ ID NO:6:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( x i ) SEQUENCE DESCRIPTION: SEQ ID NO:6:

Ser Phe Leu Leu Arg Asn Pro
1               5

( 2 ) INFORMATION FOR SEQ ID NO:7:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( x i ) SEQUENCE DESCRIPTION: SEQ ID NO:7:

Ser Phe Leu Leu Arg Asn
1               5

( 2 ) INFORMATION FOR SEQ ID NO:8:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( x i ) SEQUENCE DESCRIPTION: SEQ ID NO:8:

Ser Phe Leu Leu Arg
1               5

( 2 ) INFORMATION FOR SEQ ID NO:9:

( i ) SEQUENCE CHARACTERISTICS:
      ( A ) LENGTH: 5 amino acids (B) TYPE: amino acid
(C) STRANDEDNESS: single
(D) TOPOLOGY: linear (xi) SEQUENCE DESCRIPTION: SEQ ID NO:9:

Gly Phe Leu Leu Arg
1               5

(2) INFORMATION FOR SEQ ID NO:10:

(i) SEQUENCE CHARACTERISTICS:
(A) LENGTH: 10 amino acids
(B) TYPE: amino acid
(C) STRANDEDNESS: single
(D) TOPOLOGY: linear (xi) SEQUENCE DESCRIPTION: SEQ ID NO:10:

Thr Phe Leu Leu Arg Asn Pro Asn Asp Lys
1               5                   10

(2) INFORMATION FOR SEQ ID NO:11:

(i) SEQUENCE CHARACTERISTICS:
(A) LENGTH: 5 amino acids
(B) TYPE: amino acid
(C) STRANDEDNESS: single
(D) TOPOLOGY: linear (ix) FEATURE:
(A) NAME/KEY: Modified-site
(B) LOCATION: 2
(D) OTHER INFORMATION: /note= "This position is pClPhe."

(xi) SEQUENCE DESCRIPTION: SEQ ID NO:11:

Ser Xaa Leu Leu Arg
1               5

(2) INFORMATION FOR SEQ ID NO:12:

(i) SEQUENCE CHARACTERISTICS:
(A) LENGTH: 5 amino acids
(B) TYPE: amino acid
(C) STRANDEDNESS: single
(D) TOPOLOGY: linear (ix) FEATURE:
(A) NAME/KEY: Modified-site
(B) LOCATION: 2
(D) OTHER INFORMATION: /note= "This position is Thi."

(xi) SEQUENCE DESCRIPTION: SEQ ID NO:12:

Ser Xaa Leu Leu Arg
1               5

(2) INFORMATION FOR SEQ ID NO:13:

(i) SEQUENCE CHARACTERISTICS:
(A) LENGTH: 5 amino acids
(B) TYPE: amino acid
(C) STRANDEDNESS: single
(D) TOPOLOGY: linear (xi) SEQUENCE DESCRIPTION: SEQ ID NO:13:

Ser Phe Phe Leu Arg
1               5

(2) INFORMATION FOR SEQ ID NO:14:

(i) SEQUENCE CHARACTERISTICS:

(A) LENGTH: 6 amino acids
(B) TYPE: amino acid
(C) STRANDEDNESS: single
(D) TOPOLOGY: linear (xi) SEQUENCE DESCRIPTION: SEQ ID NO:14:

Ser Phe Phe Leu Arg Asn
1               5

(2) INFORMATION FOR SEQ ID NO:15:

(i) SEQUENCE CHARACTERISTICS:
(A) LENGTH: 5 amino acids
(B) TYPE: amino acid
(C) STRANDEDNESS: single
(D) TOPOLOGY: linear (ix) FEATURE:
(A) NAME/KEY: Modified-site
(B) LOCATION: 3
(D) OTHER INFORMATION: /note= "This position is Phg."

(xi) SEQUENCE DESCRIPTION: SEQ ID NO:15:

Ser Phe Xaa Leu Arg
1               5

(2) INFORMATION FOR SEQ ID NO:16:

(i) SEQUENCE CHARACTERISTICS:
(A) LENGTH: 6 amino acids
(B) TYPE: amino acid
(C) STRANDEDNESS: single
(D) TOPOLOGY: linear (ix) FEATURE:
(A) NAME/KEY: Modified-site
(B) LOCATION: 4
(D) OTHER INFORMATION: /note= "This position is Nal."

(xi) SEQUENCE DESCRIPTION: SEQ ID NO:16:

Ser Phe Leu Xaa Arg Asn
1               5

(2) INFORMATION FOR SEQ ID NO:17:

(i) SEQUENCE CHARACTERISTICS:
(A) LENGTH: 5 amino acids
(B) TYPE: amino acid
(C) STRANDEDNESS: single
(D) TOPOLOGY: linear (ix) FEATURE:
(A) NAME/KEY: Modified-site
(B) LOCATION: 4
(D) OTHER INFORMATION: /note= "This position is Cha."

(xi) SEQUENCE DESCRIPTION: SEQ ID NO:17:

Ser Phe Leu Xaa Arg
1               5

(2) INFORMATION FOR SEQ ID NO:18:

(i) SEQUENCE CHARACTERISTICS:
(A) LENGTH: 6 amino acids
(B) TYPE: amino acid
(C) STRANDEDNESS: single
(D) TOPOLOGY: linear (ix) FEATURE:
(A) NAME/KEY: Modified-site
(B) LOCATION: 3
(D) OTHER INFORMATION: /note= "This position is Cha."

( i x ) FEATURE:
    ( A ) NAME/KEY: Modified-site
    ( B ) LOCATION: 4
    ( D ) OTHER INFORMATION: /note= "This position is Cha."

( x i ) SEQUENCE DESCRIPTION: SEQ ID NO:18:

Ser  Phe  Xaa  Xaa  Arg  Asn
1                   5

( 2 ) INFORMATION FOR SEQ ID NO:19:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 3
        ( D ) OTHER INFORMATION: /note= "This position is Cha."

( i x ) FEATURE:
        ( A ) NAME/KEY: Modified-site
        ( B ) LOCATION: 4
        ( D ) OTHER INFORMATION: /note= "This position is Cha."

( x i ) SEQUENCE DESCRIPTION: SEQ ID NO:19:

Ser  Phe  Xaa  Xaa  Arg  Lys
1                   5

( 2 ) INFORMATION FOR SEQ ID NO:20:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 3
        ( D ) OTHER INFORMATION: /note= "This position is Cha."

( i x ) FEATURE:
        ( A ) NAME/KEY: Modified-site
        ( B ) LOCATION: 4
        ( D ) OTHER INFORMATION: /note= "This position is Cha."

( x i ) SEQUENCE DESCRIPTION: SEQ ID NO:20:

Ser  Phe  Xaa  Xaa  Leu  Arg  Asn  Pro  Asn  Asp  Lys
1                   5                        10

( 2 ) INFORMATION FOR SEQ ID NO:21:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:21:

Ser  Phe  Leu  Leu  Lys  Asn
1                   5

( 2 ) INFORMATION FOR SEQ ID NO:22:

( i ) SEQUENCE CHARACTERISTICS:
        ( A ) LENGTH: 6 amino acids
        ( B ) TYPE: amino acid
        ( C ) STRANDEDNESS: single ( D ) TOPOLOGY: linear ( i x ) FEATURE:
                    ( A ) NAME/KEY: Modified-site
                    ( B ) LOCATION: 5
                    ( D ) OTHER INFORMATION: /note= "This position is Har."

( x i ) SEQUENCE DESCRIPTION: SEQ ID NO:22:

Ser   Phe   Leu   Leu   Xaa   Asn
   1                       5

( 2 ) INFORMATION FOR SEQ ID NO:23:

( i ) SEQUENCE CHARACTERISTICS:
                    ( A ) LENGTH: 6 amino acids
                    ( B ) TYPE: amino acid
                    ( C ) STRANDEDNESS: single
                    ( D ) TOPOLOGY: linear ( x i ) SEQUENCE DESCRIPTION: SEQ ID NO:23:

Ser   Phe   Leu   Leu   Lys   Asn
   1                       5

( 2 ) INFORMATION FOR SEQ ID NO:24:

( i ) SEQUENCE CHARACTERISTICS:
                    ( A ) LENGTH: 6 amino acids
                    ( B ) TYPE: amino acid
                    ( C ) STRANDEDNESS: single
                    ( D ) TOPOLOGY: linear ( i x ) FEATURE:
                    ( A ) NAME/KEY: Modified-site
                    ( B ) LOCATION: 4
                    ( D ) OTHER INFORMATION: /note= "This position is Cha."

( x i ) SEQUENCE DESCRIPTION: SEQ ID NO:24:

Ser   Phe   Phe   Xaa   Ala   Asn
   1                       5

( 2 ) INFORMATION FOR SEQ ID NO:25:

( i ) SEQUENCE CHARACTERISTICS:
                    ( A ) LENGTH: 14 amino acids
                    ( B ) TYPE: amino acid
                    ( C ) STRANDEDNESS: single
                    ( D ) TOPOLOGY: linear ( i x ) FEATURE:
                    ( A ) NAME/KEY: Modified-site
                    ( B ) LOCATION: 1
                    ( D ) OTHER INFORMATION: /note= "This position is Mpr,
                              S-Me Mpr or Mba."

( x i ) SEQUENCE DESCRIPTION: SEQ ID NO:25:

Xaa   Phe   Leu   Leu   Arg   Asn   Pro   Asn   Asp   Lys   Tyr   Glu   Pro   Phe
   1                       5                             10

( 2 ) INFORMATION FOR SEQ ID NO:26:

( i ) SEQUENCE CHARACTERISTICS:
                    ( A ) LENGTH: 13 amino acids
                    ( B ) TYPE: amino acid
                    ( C ) STRANDEDNESS: single
                    ( D ) TOPOLOGY: linear ( i x ) FEATURE:
                    ( A ) NAME/KEY: Modified-site
                    ( B ) LOCATION: 1
                    ( D ) OTHER INFORMATION: /note= "This position is Mpr,
                              S-Me Mpr or Mba."

( x i ) SEQUENCE DESCRIPTION: SEQ ID NO:26:

Xaa Phe Leu Leu Arg Asn Pro Asn Asp Lys Tyr Glu Pro
1               5                   10

( 2 ) INFORMATION FOR SEQ ID NO:27:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Mpr,
            S-Me Mpr or Mba."

( x i ) SEQUENCE DESCRIPTION: SEQ ID NO:27:

Xaa Phe Leu Leu Arg Asn Pro Asn Asp Lys Tyr Glu
1               5                   10

( 2 ) INFORMATION FOR SEQ ID NO:28:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Mpr,
            S-Me Mpr or Mba."

( x i ) SEQUENCE DESCRIPTION: SEQ ID NO:28:

Xaa Phe Leu Leu Arg Asn Pro Asn Asp Lys Tyr
1               5                   10

( 2 ) INFORMATION FOR SEQ ID NO:29:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Mpr,
            S-Me Mpr or Mba."

( x i ) SEQUENCE DESCRIPTION: SEQ ID NO:29:

Xaa Phe Leu Leu Arg Asn Pro Asn Asp Lys
1               5                   10

( 2 ) INFORMATION FOR SEQ ID NO:30:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Mpr,
            S-Me Mpr or Mba."

( x i ) SEQUENCE DESCRIPTION: SEQ ID NO:30:

Xaa Phe Leu Leu Arg Asn Pro Asn Asp
1               5

( 2 ) INFORMATION FOR SEQ ID NO:31:

( i ) SEQUENCE CHARACTERISTICS:
       ( A ) LENGTH: 8 amino acids
       ( B ) TYPE: amino acid
       ( C ) STRANDEDNESS: single
       ( D ) TOPOLOGY: linear ( i x ) FEATURE:
       ( A ) NAME/KEY: Modified-site
       ( B ) LOCATION: 1
       ( D ) OTHER INFORMATION: /note= "This position is Mpr,
             S-Me Mpr or Mba."

( x i ) SEQUENCE DESCRIPTION: SEQ ID NO:31:

Xaa Phe Leu Leu Arg Asn Pro Asn
1               5

( 2 ) INFORMATION FOR SEQ ID NO:32:

( i ) SEQUENCE CHARACTERISTICS:
       ( A ) LENGTH: 7 amino acids
       ( B ) TYPE: amino acid
       ( C ) STRANDEDNESS: single
       ( D ) TOPOLOGY: linear ( i x ) FEATURE:
       ( A ) NAME/KEY: Modified-site
       ( B ) LOCATION: 1
       ( D ) OTHER INFORMATION: /note= "This position is Mpr,
             S-Me Mpr or Mba."

( x i ) SEQUENCE DESCRIPTION: SEQ ID NO:32:

Xaa Phe Leu Leu Arg Asn Pro
1               5

( 2 ) INFORMATION FOR SEQ ID NO:33:

( i ) SEQUENCE CHARACTERISTICS:
       ( A ) LENGTH: 6 amino acids
       ( B ) TYPE: amino acid
       ( C ) STRANDEDNESS: single
       ( D ) TOPOLOGY: linear ( i x ) FEATURE:
       ( A ) NAME/KEY: Modified-site
       ( B ) LOCATION: 1
       ( D ) OTHER INFORMATION: /note= "This position is Mpr,
             S-Me Mpr or Mba."

( x i ) SEQUENCE DESCRIPTION: SEQ ID NO:33:

Xaa Phe Leu Leu Arg Asn
1               5

( 2 ) INFORMATION FOR SEQ ID NO:34:

( i ) SEQUENCE CHARACTERISTICS:
       ( A ) LENGTH: 5 amino acids
       ( B ) TYPE: amino acid
       ( C ) STRANDEDNESS: single
       ( D ) TOPOLOGY: linear ( i x ) FEATURE:
       ( A ) NAME/KEY: Modified-site
       ( B ) LOCATION: 1
       ( D ) OTHER INFORMATION: /note= "This position is Mpr,
             S-Me Mpr or Mba."

( x i ) SEQUENCE DESCRIPTION: SEQ ID NO:34:

Xaa Phe Leu Leu Arg
1               5

( 2 ) INFORMATION FOR SEQ ID NO:35:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Mpr, S-Me Mpr or Mba."

( x i ) SEQUENCE DESCRIPTION: SEQ ID NO:35:

Xaa Phe Leu Leu
1

( 2 ) INFORMATION FOR SEQ ID NO:36:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Mpr, S-Me Mpr or Mba."

( i x ) FEATURE:
        ( A ) NAME/KEY: Modified-site
        ( B ) LOCATION: 3
        ( D ) OTHER INFORMATION: /note= "This position is Cha."

( i x ) FEATURE:
        ( A ) NAME/KEY: Modified-site
        ( B ) LOCATION: 4
        ( D ) OTHER INFORMATION: /note= "This position is Cha."

( x i ) SEQUENCE DESCRIPTION: SEQ ID NO:36:

Xaa Phe Xaa Xaa Arg Asn Pro Asn Asp Lys
1               5                   1 0

( 2 ) INFORMATION FOR SEQ ID NO:37:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Mpr, S-Me Mpr or Mba."

( i x ) FEATURE:
        ( A ) NAME/KEY: Modified-site
        ( B ) LOCATION: 3
        ( D ) OTHER INFORMATION: /note= "This position is Cha."

( i x ) FEATURE:
        ( A ) NAME/KEY: Modified-site
        ( B ) LOCATION: 4
        ( D ) OTHER INFORMATION: /note= "This position is Cha."

( x i ) SEQUENCE DESCRIPTION: SEQ ID NO:37:

Xaa Phe Xaa Xaa Arg Asn Pro Asn Asp Lys Tyr
1               5                       10

( 2 ) INFORMATION FOR SEQ ID NO:38:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Mpr, S-Me Mpr or Mba."

( i x ) FEATURE:
        ( A ) NAME/KEY: Modified-site
        ( B ) LOCATION: 3
        ( D ) OTHER INFORMATION: /note= "This position is Cha."

( i x ) FEATURE:
        ( A ) NAME/KEY: Modified-site
        ( B ) LOCATION: 4
        ( D ) OTHER INFORMATION: /note= "This position is Cha."

( i x ) FEATURE:
        ( A ) NAME/KEY: Modified-site
        ( B ) LOCATION: 12
        ( D ) OTHER INFORMATION: /note= "This position is E-NH2."

( x i ) SEQUENCE DESCRIPTION: SEQ ID NO:38:

Xaa Phe Xaa Xaa Arg Asn Pro Asn Asp Lys Tyr Glu
1               5                       10

( 2 ) INFORMATION FOR SEQ ID NO:39:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Mpr, S-Me Mpr or Mba."

( i x ) FEATURE:
        ( A ) NAME/KEY: Modified-site
        ( B ) LOCATION: 3
        ( D ) OTHER INFORMATION: /note= "This position is Cha."

( i x ) FEATURE:
        ( A ) NAME/KEY: Modified-site
        ( B ) LOCATION: 4
        ( D ) OTHER INFORMATION: /note= "This position is Cha."

( i x ) FEATURE:
        ( A ) NAME/KEY: Modified-site
        ( B ) LOCATION: 11
        ( D ) OTHER INFORMATION: /note= "This position is Y-NH2."

( x i ) SEQUENCE DESCRIPTION: SEQ ID NO:39:

Xaa Phe Xaa Xaa Arg Asn Pro Asn Asp Lys Tyr
1               5                       10

( 2 ) INFORMATION FOR SEQ ID NO:40:

( i ) SEQUENCE CHARACTERISTICS:
        ( A ) LENGTH: 10 amino acids (B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note= "This position is Mpr, S-Me Mpr or Mba."

(ix) FEATURE:
(A) NAME/KEY: Modified-site
(B) LOCATION: 3
(D) OTHER INFORMATION: /note= "This position is Cha."

(ix) FEATURE:
(A) NAME/KEY: Modified-site
(B) LOCATION: 4
(D) OTHER INFORMATION: /note= "This position is Cha."

(ix) FEATURE:
(A) NAME/KEY: Modified-site
(B) LOCATION: 10
(D) OTHER INFORMATION: /note= "This position is K-NH2."

(xi) SEQUENCE DESCRIPTION: SEQ ID NO:40:

Xaa Phe Xaa Xaa Arg Asn Pro Asn Asp Lys
1               5                   10

(2) INFORMATION FOR SEQ ID NO:41:

(i) SEQUENCE CHARACTERISTICS:
(A) LENGTH: 9 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note= "This position is Mpr, S-Me Mpr or Mba."

(ix) FEATURE:
(A) NAME/KEY: Modified-site
(B) LOCATION: 3
(D) OTHER INFORMATION: /note= "This position is Cha."

(ix) FEATURE:
(A) NAME/KEY: Modified-site
(B) LOCATION: 4
(D) OTHER INFORMATION: /note= "This position is Cha."

(ix) FEATURE:
(A) NAME/KEY: Modified-site
(B) LOCATION: 9
(D) OTHER INFORMATION: /note= "This position is D-NH2."

(xi) SEQUENCE DESCRIPTION: SEQ ID NO:41:

Xaa Phe Xaa Xaa Arg Asn Pro Asn Asp
1               5

(2) INFORMATION FOR SEQ ID NO:42:

(i) SEQUENCE CHARACTERISTICS:
(A) LENGTH: 6 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note= "This position is Mpr, S-Me Mpr or Mba."

( i x ) FEATURE:
  ( A ) NAME/KEY: Modified-site
  ( B ) LOCATION: 3
  ( D ) OTHER INFORMATION: /note= "This position is Cha."

( i x ) FEATURE:
  ( A ) NAME/KEY: Modified-site
  ( B ) LOCATION: 4
  ( D ) OTHER INFORMATION: /note= "This position is Cha."

( i x ) FEATURE:
  ( A ) NAME/KEY: Modified-site
  ( B ) LOCATION: 6
  ( D ) OTHER INFORMATION: /note= "This position is N-NH2."

( x i ) SEQUENCE DESCRIPTION: SEQ ID NO:42:

Xaa Phe Xaa Xaa Arg Asn
1               5

( 2 ) INFORMATION FOR SEQ ID NO:43:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /note= "This position is Mpr,
           S-Me Mpr or Mba."

( i x ) FEATURE:
    ( A ) NAME/KEY: Modified-site
    ( B ) LOCATION: 3
    ( D ) OTHER INFORMATION: /note= "This position is Cha."

( i x ) FEATURE:
    ( A ) NAME/KEY: Modified-site
    ( B ) LOCATION: 4
    ( D ) OTHER INFORMATION: /note= "This position is Cha."

( i x ) FEATURE:
    ( A ) NAME/KEY: Modified-site
    ( B ) LOCATION: 10
    ( D ) OTHER INFORMATION: /note= "This position is K-NH2."

( x i ) SEQUENCE DESCRIPTION: SEQ ID NO:43:

Xaa Phe Xaa Xaa Arg Ala Pro Asn Asp Lys
1               5                        10

( 2 ) INFORMATION FOR SEQ ID NO:44:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /note= "This position is Mpr,
           S-Me Mpr or Mba."

( i x ) FEATURE:
    ( A ) NAME/KEY: Modified-site
    ( B ) LOCATION: 3
    ( D ) OTHER INFORMATION: /note= "This position is Cha."

( i x ) FEATURE:
    ( A ) NAME/KEY: Modified-site
    ( B ) LOCATION: 4
    ( D ) OTHER INFORMATION: /note= "This position is Cha."

( i x ) FEATURE:
    ( A ) NAME/KEY: Modified-site
    ( B ) LOCATION: 10
    ( D ) OTHER INFORMATION: /note= "This position is K-NH2."

( x i ) SEQUENCE DESCRIPTION: SEQ ID NO:44:

```
Xaa  Phe  Xaa  Xaa  Arg  Gly  Pro  Asn  Asp  Lys
1                  5                        10
```

( 2 ) INFORMATION FOR SEQ ID NO:45:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i x ) FEATURE:
    ( A ) NAME/KEY: Modified-site
    ( B ) LOCATION: 1
    ( D ) OTHER INFORMATION: /note= "This position is Mpr,
        S-Me Mpr or Mba."

( i x ) FEATURE:
    ( A ) NAME/KEY: Modified-site
    ( B ) LOCATION: 3
    ( D ) OTHER INFORMATION: /note= "This position is Cha."

( i x ) FEATURE:
    ( A ) NAME/KEY: Modified-site
    ( B ) LOCATION: 4
    ( D ) OTHER INFORMATION: /note= "This position is Cha."

( i x ) FEATURE:
    ( A ) NAME/KEY: Modified-site
    ( B ) LOCATION: 10
    ( D ) OTHER INFORMATION: /note= "This position is K-NH2."

( x i ) SEQUENCE DESCRIPTION: SEQ ID NO:45:

```
Xaa  Phe  Xaa  Xaa  Arg  Lys  Pro  Asn  Asp  Lys
1                  5                        10
```

( 2 ) INFORMATION FOR SEQ ID NO:46:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i x ) FEATURE:
    ( A ) NAME/KEY: Modified-site
    ( B ) LOCATION: 1
    ( D ) OTHER INFORMATION: /note= "This position is Mpr,
        S-Me Mpr or Mba."

( i x ) FEATURE:
    ( A ) NAME/KEY: Modified-site
    ( B ) LOCATION: 3
    ( D ) OTHER INFORMATION: /note= "This position is Cha."

( i x ) FEATURE:
    ( A ) NAME/KEY: Modified-site
    ( B ) LOCATION: 4
    ( D ) OTHER INFORMATION: /note= "This position is Cha."

( i x ) FEATURE:
    ( A ) NAME/KEY: Modified-site
    ( B ) LOCATION: 10
    ( D ) OTHER INFORMATION: /note= "This position is K-NH2."

( x i ) SEQUENCE DESCRIPTION: SEQ ID NO:46:

```
Xaa  Phe  Xaa  Xaa  Arg  Asn  Ala  Asn  Asp  Lys
1                  5                        10
```

( 2 ) INFORMATION FOR SEQ ID NO:47:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Mpr, S-Me Mpr or Mba."

( i x ) FEATURE:
        ( A ) NAME/KEY: Modified-site
        ( B ) LOCATION: 3
        ( D ) OTHER INFORMATION: /note= "This position is Cha."

( i x ) FEATURE:
        ( A ) NAME/KEY: Modified-site
        ( B ) LOCATION: 4
        ( D ) OTHER INFORMATION: /note= "This position is Cha."

( i x ) FEATURE:
        ( A ) NAME/KEY: Modified-site
        ( B ) LOCATION: 10
        ( D ) OTHER INFORMATION: /note= "This position is K-NH2."

( x i ) SEQUENCE DESCRIPTION: SEQ ID NO:47:

Xaa Phe Xaa Xaa Arg Asn Pro Ala Asp Lys
1               5                   10

( 2 ) INFORMATION FOR SEQ ID NO:48:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Mpr, S-Me Mpr or Mba."

( i x ) FEATURE:
        ( A ) NAME/KEY: Modified-site
        ( B ) LOCATION: 3
        ( D ) OTHER INFORMATION: /note= "This position is Cha."

( i x ) FEATURE:
        ( A ) NAME/KEY: Modified-site
        ( B ) LOCATION: 4
        ( D ) OTHER INFORMATION: /note= "This position is Cha."

( i x ) FEATURE:
        ( A ) NAME/KEY: Modified-site
        ( B ) LOCATION: 10
        ( D ) OTHER INFORMATION: /note= "This position is A-NH2."

( x i ) SEQUENCE DESCRIPTION: SEQ ID NO:48:

Xaa Phe Xaa Xaa Arg Asn Pro Asn Asp Ala
1               5                   10

( 2 ) INFORMATION FOR SEQ ID NO:49:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i x ) FEATURE:

(A) NAME/KEY: Modified-site
(B) LOCATION: 1
(D) OTHER INFORMATION: /note= "This position is Mpr, S-Me Mpr or Mba."

(ix) FEATURE:
(A) NAME/KEY: Modified-site
(B) LOCATION: 3
(D) OTHER INFORMATION: /note= "This position is Cha."

(ix) FEATURE:
(A) NAME/KEY: Modified-site
(B) LOCATION: 4
(D) OTHER INFORMATION: /note= "This position is Cha."

(ix) FEATURE:
(A) NAME/KEY: Modified-site
(B) LOCATION: 10
(D) OTHER INFORMATION: /note= "This position is K-NH2."

(xi) SEQUENCE DESCRIPTION: SEQ ID NO:49:

Xaa Phe Xaa Xaa Arg Lys Pro Asn Glu Lys
1               5                   10

(2) INFORMATION FOR SEQ ID NO:50:

(i) SEQUENCE CHARACTERISTICS:
(A) LENGTH: 10 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note= "This position is Mpr, S-Me Mpr or Mba."

(ix) FEATURE:
(A) NAME/KEY: Modified-site
(B) LOCATION: 3
(D) OTHER INFORMATION: /note= "This position is Cha."

(ix) FEATURE:
(A) NAME/KEY: Modified-site
(B) LOCATION: 4
(D) OTHER INFORMATION: /note= "This position is Cha."

(ix) FEATURE:
(A) NAME/KEY: Modified-site
(B) LOCATION: 10
(D) OTHER INFORMATION: /note= "This position is A-NH2."

(xi) SEQUENCE DESCRIPTION: SEQ ID NO:50:

Xaa Phe Xaa Xaa Arg Lys Pro Asn Asp Ala
1               5                   10

(2) INFORMATION FOR SEQ ID NO:51:

(i) SEQUENCE CHARACTERISTICS:
(A) LENGTH: 10 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note= "This position is Mpr."

(ix) FEATURE:
(A) NAME/KEY: Modified-site
(B) LOCATION: 3
(D) OTHER INFORMATION: /note= "This position is Cha."

(ix) FEATURE:

(A) NAME/KEY: Modified-site
            (B) LOCATION: 4
            (D) OTHER INFORMATION: /note= "This position is Cha."

(xi) SEQUENCE DESCRIPTION: SEQ ID NO:51:

Xaa Phe Xaa Xaa Arg Asn Pro Asn Asp Lys
    1               5                   10

(2) INFORMATION FOR SEQ ID NO:52:

(i) SEQUENCE CHARACTERISTICS:
            (A) LENGTH: 11 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 1
            (D) OTHER INFORMATION: /note= "This position is Mpr."

(ix) FEATURE:
            (A) NAME/KEY: Modified-site
            (B) LOCATION: 3
            (D) OTHER INFORMATION: /note= "This position is Cha."

(ix) FEATURE:
            (A) NAME/KEY: Modified-site
            (B) LOCATION: 4
            (D) OTHER INFORMATION: /note= "This position is Cha."

(xi) SEQUENCE DESCRIPTION: SEQ ID NO:52:

Xaa Phe Xaa Xaa Arg Asn Pro Asn Asp Lys Tyr
    1               5                   10

(2) INFORMATION FOR SEQ ID NO:53:

(i) SEQUENCE CHARACTERISTICS:
            (A) LENGTH: 12 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 1
            (D) OTHER INFORMATION: /note= "This position is Mpr."

(ix) FEATURE:
            (A) NAME/KEY: Modified-site
            (B) LOCATION: 3
            (D) OTHER INFORMATION: /note= "This position is Cha."

(ix) FEATURE:
            (A) NAME/KEY: Modified-site
            (B) LOCATION: 4
            (D) OTHER INFORMATION: /note= "This position is Cha."

(ix) FEATURE:
            (A) NAME/KEY: Modified-site
            (B) LOCATION: 12
            (D) OTHER INFORMATION: /note= "This position is E-NH2."

(xi) SEQUENCE DESCRIPTION: SEQ ID NO:53:

Xaa Phe Xaa Xaa Arg Asn Pro Asn Asp Lys Tyr Glu
    1               5                   10

(2) INFORMATION FOR SEQ ID NO:54:

(i) SEQUENCE CHARACTERISTICS:
            (A) LENGTH: 11 amino acids
            (B) TYPE: amino acid
            (C) STRANDEDNESS: single
            (D) TOPOLOGY: linear ( i x ) FEATURE:
  ( A ) NAME/KEY: Modified-site
  ( B ) LOCATION: 1
  ( D ) OTHER INFORMATION: /note= "This position is Mpr."

( i x ) FEATURE:
  ( A ) NAME/KEY: Modified-site
  ( B ) LOCATION: 3
  ( D ) OTHER INFORMATION: /note= "This position is Cha."

( i x ) FEATURE:
  ( A ) NAME/KEY: Modified-site
  ( B ) LOCATION: 4
  ( D ) OTHER INFORMATION: /note= "This position is Cha."

( i x ) FEATURE:
  ( A ) NAME/KEY: Modified-site
  ( B ) LOCATION: 11
  ( D ) OTHER INFORMATION: /note= "This position is Y-NH2."

( x i ) SEQUENCE DESCRIPTION: SEQ ID NO:54:

Xaa Phe Xaa Xaa Arg Asn Pro Asn Asp Lys Tyr
1               5                   10

( 2 ) INFORMATION FOR SEQ ID NO:55:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /note= "This position is Mpr."

( i x ) FEATURE:
    ( A ) NAME/KEY: Modified-site
    ( B ) LOCATION: 3
    ( D ) OTHER INFORMATION: /note= "This position is Cha."

( i x ) FEATURE:
    ( A ) NAME/KEY: Modified-site
    ( B ) LOCATION: 4
    ( D ) OTHER INFORMATION: /note= "This position is Cha."

( i x ) FEATURE:
    ( A ) NAME/KEY: Modified-site
    ( B ) LOCATION: 10
    ( D ) OTHER INFORMATION: /note= "This position is K-NH2."

( x i ) SEQUENCE DESCRIPTION: SEQ ID NO:55:

Xaa Phe Xaa Xaa Arg Asn Pro Asn Asp Lys
1               5                   10

( 2 ) INFORMATION FOR SEQ ID NO:56:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /note= "This position is Mpr."

( i x ) FEATURE:
    ( A ) NAME/KEY: Modified-site
    ( B ) LOCATION: 3
    ( D ) OTHER INFORMATION: /note= "This position is Cha."

( i x ) FEATURE:

(A) NAME/KEY: Modified-site
(B) LOCATION: 4
(D) OTHER INFORMATION: /note= "This position is Cha."

(ix) FEATURE:
(A) NAME/KEY: Modified-site
(B) LOCATION: 9
(D) OTHER INFORMATION: /note= "This position is D-NH2."

(xi) SEQUENCE DESCRIPTION: SEQ ID NO:56:

Xaa Phe Xaa Xaa Arg Asn Pro Asn Asp
1               5

(2) INFORMATION FOR SEQ ID NO:57:

(i) SEQUENCE CHARACTERISTICS:
(A) LENGTH: 6 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note= "This position is Mpr."

(ix) FEATURE:
(A) NAME/KEY: Modified-site
(B) LOCATION: 3
(D) OTHER INFORMATION: /note= "This position is Cha."

(ix) FEATURE:
(A) NAME/KEY: Modified-site
(B) LOCATION: 4
(D) OTHER INFORMATION: /note= "This position is Cha."

(ix) FEATURE:
(A) NAME/KEY: Modified-site
(B) LOCATION: 6
(D) OTHER INFORMATION: /note= "This position is N-NH2."

(xi) SEQUENCE DESCRIPTION: SEQ ID NO:57:

Xaa Phe Xaa Xaa Arg Asn
1               5

(2) INFORMATION FOR SEQ ID NO:58:

(i) SEQUENCE CHARACTERISTICS:
(A) LENGTH: 10 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note= "This position is Mpr."

(ix) FEATURE:
(A) NAME/KEY: Modified-site
(B) LOCATION: 3
(D) OTHER INFORMATION: /note= "This position is Cha."

(ix) FEATURE:
(A) NAME/KEY: Modified-site
(B) LOCATION: 4
(D) OTHER INFORMATION: /note= "This position is Cha."

(ix) FEATURE:
(A) NAME/KEY: Modified-site
(B) LOCATION: 10
(D) OTHER INFORMATION: /note= "This position is K-NH2."

(xi) SEQUENCE DESCRIPTION: SEQ ID NO:58:

Xaa Phe Xaa Xaa Arg Ala Pro Asn Asp Lys ( 2 ) INFORMATION FOR SEQ ID NO:59:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Mpr."

( i x ) FEATURE:
        ( A ) NAME/KEY: Modified-site
        ( B ) LOCATION: 3
        ( D ) OTHER INFORMATION: /note= "This position is Cha."

( i x ) FEATURE:
        ( A ) NAME/KEY: Modified-site
        ( B ) LOCATION: 4
        ( D ) OTHER INFORMATION: /note= "This position is Cha."

( i x ) FEATURE:
        ( A ) NAME/KEY: Modified-site
        ( B ) LOCATION: 10
        ( D ) OTHER INFORMATION: /note= "This position is K-NH2."

( x i ) SEQUENCE DESCRIPTION: SEQ ID NO:59:

Xaa  Phe  Xaa  Xaa  Arg  Gly  Pro  Asn  Asp  Lys
    1                 5                     10

( 2 ) INFORMATION FOR SEQ ID NO:60:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Mpr."

( i x ) FEATURE:
        ( A ) NAME/KEY: Modified-site
        ( B ) LOCATION: 3
        ( D ) OTHER INFORMATION: /note= "This position is Cha."

( i x ) FEATURE:
        ( A ) NAME/KEY: Modified-site
        ( B ) LOCATION: 4
        ( D ) OTHER INFORMATION: /note= "This position is Cha."

( i x ) FEATURE:
        ( A ) NAME/KEY: Modified-site
        ( B ) LOCATION: 10
        ( D ) OTHER INFORMATION: /note= "This position is K-NH2."

( x i ) SEQUENCE DESCRIPTION: SEQ ID NO:60:

Xaa  Phe  Xaa  Xaa  Arg  Lys  Pro  Asn  Asp  Lys
    1                 5                     10

( 2 ) INFORMATION FOR SEQ ID NO:61:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i x ) FEATURE:

( A ) NAME/KEY: Modified-site
( B ) LOCATION: 1
( D ) OTHER INFORMATION: /note= "This position is Mpr."

( i x ) FEATURE:
( A ) NAME/KEY: Modified-site
( B ) LOCATION: 3
( D ) OTHER INFORMATION: /note= "This position is Cha."

( i x ) FEATURE:
( A ) NAME/KEY: Modified-site
( B ) LOCATION: 4
( D ) OTHER INFORMATION: /note= "This position is Cha."

( i x ) FEATURE:
( A ) NAME/KEY: Modified-site
( B ) LOCATION: 10
( D ) OTHER INFORMATION: /note= "This position is K-NH2."

( x i ) SEQUENCE DESCRIPTION: SEQ ID NO:61:

Xaa Phe Xaa Xaa Arg Asn Ala Asn Asp Lys
1               5                   10

( 2 ) INFORMATION FOR SEQ ID NO:62:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 1
( D ) OTHER INFORMATION: /note= "This position is Mpr."

( i x ) FEATURE:
( A ) NAME/KEY: Modified-site
( B ) LOCATION: 3
( D ) OTHER INFORMATION: /note= "This position is Cha."

( i x ) FEATURE:
( A ) NAME/KEY: Modified-site
( B ) LOCATION: 4
( D ) OTHER INFORMATION: /note= "This position is Cha."

( i x ) FEATURE:
( A ) NAME/KEY: Modified-site
( B ) LOCATION: 10
( D ) OTHER INFORMATION: /note= "This position is K-NH2."

( x i ) SEQUENCE DESCRIPTION: SEQ ID NO:62:

Xaa Phe Xaa Xaa Arg Asn Pro Ala Asp Lys
1               5                   10

( 2 ) INFORMATION FOR SEQ ID NO:63:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 1
( D ) OTHER INFORMATION: /note= "This position is Mpr."

( i x ) FEATURE:
( A ) NAME/KEY: Modified-site
( B ) LOCATION: 3
( D ) OTHER INFORMATION: /note= "This position is Cha."

( i x ) FEATURE:
( A ) NAME/KEY: Modified-site
( B ) LOCATION: 4

( D ) OTHER INFORMATION: /note= "This position is Cha."

( i x ) FEATURE:
    ( A ) NAME/KEY: Modified-site
    ( B ) LOCATION: 10
    ( D ) OTHER INFORMATION: /note= "This position is A-NH2."

( x i ) SEQUENCE DESCRIPTION: SEQ ID NO:63:

```
Xaa Phe Xaa Xaa Arg Asn Pro Asn Asp Ala
1               5                   10
```

( 2 ) INFORMATION FOR SEQ ID NO:64:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Mpr."

( i x ) FEATURE:
        ( A ) NAME/KEY: Modified-site
        ( B ) LOCATION: 3
        ( D ) OTHER INFORMATION: /note= "This position is Cha."

( i x ) FEATURE:
        ( A ) NAME/KEY: Modified-site
        ( B ) LOCATION: 4
        ( D ) OTHER INFORMATION: /note= "This position is Cha."

( i x ) FEATURE:
        ( A ) NAME/KEY: Modified-site
        ( B ) LOCATION: 10
        ( D ) OTHER INFORMATION: /note= "This position is K-NH2."

( x i ) SEQUENCE DESCRIPTION: SEQ ID NO:64:

```
Xaa Phe Xaa Xaa Arg Lys Pro Asn Glu Lys
1               5                   10
```

( 2 ) INFORMATION FOR SEQ ID NO:65:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Mpr."

( i x ) FEATURE:
        ( A ) NAME/KEY: Modified-site
        ( B ) LOCATION: 3
        ( D ) OTHER INFORMATION: /note= "This position is Cha."

( i x ) FEATURE:
        ( A ) NAME/KEY: Modified-site
        ( B ) LOCATION: 4
        ( D ) OTHER INFORMATION: /note= "This position is Cha."

( i x ) FEATURE:
        ( A ) NAME/KEY: Modified-site
        ( B ) LOCATION: 10
        ( D ) OTHER INFORMATION: /note= "This position is A-NH2."

( x i ) SEQUENCE DESCRIPTION: SEQ ID NO:65:

```
Xaa Phe Xaa Xaa Arg Lys Pro Asn Asp Ala
1               5                   10
```

( 2 ) INFORMATION FOR SEQ ID NO:66:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Mba."

( i x ) FEATURE:
        ( A ) NAME/KEY: Modified-site
        ( B ) LOCATION: 3
        ( D ) OTHER INFORMATION: /note= "This position is Cha."

( i x ) FEATURE:
        ( A ) NAME/KEY: Modified-site
        ( B ) LOCATION: 4
        ( D ) OTHER INFORMATION: /note= "This position is Cha."

( i x ) FEATURE:
        ( A ) NAME/KEY: Modified-site
        ( B ) LOCATION: 10
        ( D ) OTHER INFORMATION: /note= "This position is K-NH2."

( x i ) SEQUENCE DESCRIPTION: SEQ ID NO:66:

```
Xaa  Phe  Xaa  Xaa  Arg  Lys  Pro  Asn  Asp  Lys
1                  5                            10
```

( 2 ) INFORMATION FOR SEQ ID NO:67:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is
            SMeMpr."

( i x ) FEATURE:
        ( A ) NAME/KEY: Modified-site
        ( B ) LOCATION: 3
        ( D ) OTHER INFORMATION: /note= "This position is Cha."

( i x ) FEATURE:
        ( A ) NAME/KEY: Modified-site
        ( B ) LOCATION: 4
        ( D ) OTHER INFORMATION: /note= "This position is Cha."

( i x ) FEATURE:
        ( A ) NAME/KEY: Modified-site
        ( B ) LOCATION: 10
        ( D ) OTHER INFORMATION: /note= "This position is K-NH2."

( x i ) SEQUENCE DESCRIPTION: SEQ ID NO:67:

```
Xaa  Phe  Xaa  Xaa  Arg  Lys  Pro  Asn  Asp  Lys
1                  5                            10
```

( 2 ) INFORMATION FOR SEQ ID NO:68:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:68:

Leu Asp Pro Arg Pro
1               5

( 2 ) INFORMATION FOR SEQ ID NO:69:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( x i ) SEQUENCE DESCRIPTION: SEQ ID NO:69:

Leu Glu Pro Arg Pro
1               5

( 2 ) INFORMATION FOR SEQ ID NO:70:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( x i ) SEQUENCE DESCRIPTION: SEQ ID NO:70:

Ile Asp Pro Arg Pro
1               5

( 2 ) INFORMATION FOR SEQ ID NO:71:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( x i ) SEQUENCE DESCRIPTION: SEQ ID NO:71:

Ile Glu Pro Arg Pro
1               5

( 2 ) INFORMATION FOR SEQ ID NO:72:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( x i ) SEQUENCE DESCRIPTION: SEQ ID NO:72:

Val Asp Pro Arg Pro
1               5

( 2 ) INFORMATION FOR SEQ ID NO:73:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( x i ) SEQUENCE DESCRIPTION: SEQ ID NO:73:

Val Glu Pro Arg Pro
1               5

( 2 ) INFORMATION FOR SEQ ID NO:74:

( i ) SEQUENCE CHARACTERISTICS:
    ( A ) LENGTH: 27 amino acids
    ( B ) TYPE: amino acid
    ( C ) STRANDEDNESS: single (D) TOPOLOGY: linear (xi) SEQUENCE DESCRIPTION: SEQ ID NO:74:

Leu Asp Pro Arg Pro Phe Leu Leu Arg Asn Pro Asn Asp Lys Tyr Glu
1               5                   10                  15
Pro Phe Trp Glu Asp Glu Glu Lys Asn Glu Ser
            20              25

(2) INFORMATION FOR SEQ ID NO:75:

(i) SEQUENCE CHARACTERISTICS:
    (A) LENGTH: 26 amino acids
    (B) TYPE: amino acid
    (C) STRANDEDNESS: single
    (D) TOPOLOGY: linear (xi) SEQUENCE DESCRIPTION: SEQ ID NO:75:

Leu Asp Pro Arg Pro Phe Leu Leu Arg Asn Pro Asn Asp Lys Tyr Glu
1               5                   10                  15
Pro Phe Trp Glu Asp Glu Glu Lys Asn Glu
            20              25

(2) INFORMATION FOR SEQ ID NO:76:

(i) SEQUENCE CHARACTERISTICS:
    (A) LENGTH: 25 amino acids
    (B) TYPE: amino acid
    (C) STRANDEDNESS: single
    (D) TOPOLOGY: linear (xi) SEQUENCE DESCRIPTION: SEQ ID NO:76:

Leu Asp Pro Arg Pro Phe Leu Leu Arg Asn Pro Asn Asp Lys Tyr Glu
1               5                   10                  15
Pro Phe Trp Glu Asp Glu Glu Lys Asn
            20              25

(2) INFORMATION FOR SEQ ID NO:77:

(i) SEQUENCE CHARACTERISTICS:
    (A) LENGTH: 24 amino acids
    (B) TYPE: amino acid
    (C) STRANDEDNESS: single
    (D) TOPOLOGY: linear (xi) SEQUENCE DESCRIPTION: SEQ ID NO:77:

Leu Asp Pro Arg Pro Phe Leu Leu Arg Asn Pro Asn Asp Lys Tyr Glu
1               5                   10                  15
Pro Phe Trp Glu Asp Glu Glu Lys
            20

(2) INFORMATION FOR SEQ ID NO:78:

(i) SEQUENCE CHARACTERISTICS:
    (A) LENGTH: 23 amino acids
    (B) TYPE: amino acid
    (C) STRANDEDNESS: single
    (D) TOPOLOGY: linear (xi) SEQUENCE DESCRIPTION: SEQ ID NO:78:

Leu Asp Pro Arg Pro Phe Leu Leu Arg Asn Pro Asn Asp Lys Tyr Glu
1               5                   10                  15
Pro Phe Trp Glu Asp Glu Glu
            20

(2) INFORMATION FOR SEQ ID NO:79:

( i ) SEQUENCE CHARACTERISTICS:
  ( A ) LENGTH: 22 amino acids
  ( B ) TYPE: amino acid
  ( C ) STRANDEDNESS: single
  ( D ) TOPOLOGY: linear ( x i ) SEQUENCE DESCRIPTION: SEQ ID NO:79:

Leu Asp Pro Arg Pro Phe Leu Leu Arg Asn Pro Asn Asp Lys Tyr Glu
1               5                   10                  15

Pro Phe Trp Glu Asp Glu
            20

( 2 ) INFORMATION FOR SEQ ID NO:80:

( i ) SEQUENCE CHARACTERISTICS:
  ( A ) LENGTH: 21 amino acids
  ( B ) TYPE: amino acid
  ( C ) STRANDEDNESS: single
  ( D ) TOPOLOGY: linear ( x i ) SEQUENCE DESCRIPTION: SEQ ID NO:80:

Leu Asp Pro Arg Pro Phe Leu Leu Arg Asn Pro Asn Asp Lys Tyr Glu
1               5                   10                  15

Pro Phe Trp Glu Asp
            20

( 2 ) INFORMATION FOR SEQ ID NO:81:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( x i ) SEQUENCE DESCRIPTION: SEQ ID NO:81:

Tyr Glu Pro Phe Trp
1               5

( 2 ) INFORMATION FOR SEQ ID NO:82:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( x i ) SEQUENCE DESCRIPTION: SEQ ID NO:82:

Glu Asp Glu Glu
1

( 2 ) INFORMATION FOR SEQ ID NO:83:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( x i ) SEQUENCE DESCRIPTION: SEQ ID NO:83:

Phe Glu Pro Phe Trp
1               5

( 2 ) INFORMATION FOR SEQ ID NO:84:

( i ) SEQUENCE CHARACTERISTICS:
  ( A ) LENGTH: 5 amino acids
  ( B ) TYPE: amino acid (C) STRANDEDNESS: single
(D) TOPOLOGY: linear (x i) SEQUENCE DESCRIPTION: SEQ ID NO:84:

Tyr Asp Pro Phe Trp
1                 5

(2) INFORMATION FOR SEQ ID NO:85:

(i) SEQUENCE CHARACTERISTICS:
    (A) LENGTH: 5 amino acids
    (B) TYPE: amino acid
    (C) STRANDEDNESS: single
    (D) TOPOLOGY: linear (x i) SEQUENCE DESCRIPTION: SEQ ID NO:85:

Tyr Glu Pro Tyr Trp
1                 5

(2) INFORMATION FOR SEQ ID NO:86:

(i) SEQUENCE CHARACTERISTICS:
    (A) LENGTH: 5 amino acids
    (B) TYPE: amino acid
    (C) STRANDEDNESS: single
    (D) TOPOLOGY: linear (x i) SEQUENCE DESCRIPTION: SEQ ID NO:86:

Tyr Glu Pro Phe Tyr
1                 5

(2) INFORMATION FOR SEQ ID NO:87:

(i) SEQUENCE CHARACTERISTICS:
    (A) LENGTH: 5 amino acids
    (B) TYPE: amino acid
    (C) STRANDEDNESS: single
    (D) TOPOLOGY: linear (x i) SEQUENCE DESCRIPTION: SEQ ID NO:87:

Tyr Glu Pro Trp Tyr
1                 5

(2) INFORMATION FOR SEQ ID NO:88:

(i) SEQUENCE CHARACTERISTICS:
    (A) LENGTH: 5 amino acids
    (B) TYPE: amino acid
    (C) STRANDEDNESS: single
    (D) TOPOLOGY: linear (x i) SEQUENCE DESCRIPTION: SEQ ID NO:88:

Trp Glu Pro Phe Trp
1                 5

(2) INFORMATION FOR SEQ ID NO:89:

(i) SEQUENCE CHARACTERISTICS:
    (A) LENGTH: 4 amino acids
    (B) TYPE: amino acid
    (C) STRANDEDNESS: single
    (D) TOPOLOGY: linear (x i) SEQUENCE DESCRIPTION: SEQ ID NO:89:

Glu Asp Glu Glu
1

(2) INFORMATION FOR SEQ ID NO:90:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:90:

Gln Asp Gln Gln
1

( 2 ) INFORMATION FOR SEQ ID NO:91:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:91:

Glu Asp Glu Gln
1

( 2 ) INFORMATION FOR SEQ ID NO:92:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:92:

Gln Asp Glu Gln
1

( 2 ) INFORMATION FOR SEQ ID NO:93:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:93:

Gln Asp Glu Glu
1

( 2 ) INFORMATION FOR SEQ ID NO:94:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:94:

Glu Asp Gln Glu
1

( 2 ) INFORMATION FOR SEQ ID NO:95:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:95:

Glu Asp Gln Gln ( 2 ) INFORMATION FOR SEQ ID NO:96:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:96:

Gln Asp Gln Glu
1

( 2 ) INFORMATION FOR SEQ ID NO:97:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:97:

Trp Lys Lys Lys Lys
1                   5

( 2 ) INFORMATION FOR SEQ ID NO:98:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:98:

Lys Lys Lys Lys Trp
1                   5

( 2 ) INFORMATION FOR SEQ ID NO:99:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:99:

Gln Lys Gln Gln Trp
1                   5

( 2 ) INFORMATION FOR SEQ ID NO:100:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:100:

Trp Gln Lys Gln Gln
1                   5

( 2 ) INFORMATION FOR SEQ ID NO:101:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( x i ) SEQUENCE DESCRIPTION: SEQ ID NO:101:

```
Pro Glu Ser Lys Ala Thr Asn Ala Thr Leu Asp Pro Arg Ser Phe Leu
1               5                   10                  15

Leu Arg Asn Pro Asn Asp Lys Tyr Glu Pro Phe Trp Glu Asp Glu Glu
            20                  25                  30

Lys Asn Glu Ser Gly Leu Thr Glu Tyr
            35                  40
```

( 2 ) INFORMATION FOR SEQ ID NO:102:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO:102:

```
Tyr Tyr Phe Ser Gly Ser Asp Trp Gln Phe Gly Ser Glu Leu Cys Arg
1               5                   10                  15
```

( 2 ) INFORMATION FOR SEQ ID NO:103:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( x i ) SEQUENCE DESCRIPTION: SEQ ID NO:103:

```
Lys Glu Gln Thr Ile Gln Val Pro Gly Leu Asn Ile Thr Thr Cys His
1               5                   10                  15

Asp Val Leu Asn Glu Thr Leu Leu Glu Gly
            20                  25
```

( 2 ) INFORMATION FOR SEQ ID NO:104:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO:104:

```
His Tyr Ser Phe Leu Ser His Thr Ser Thr Thr
1               5                   10
```

( 2 ) INFORMATION FOR SEQ ID NO:105:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 6
        ( D ) OTHER INFORMATION: /note= "This position is N-NH2."

( x i ) SEQUENCE DESCRIPTION: SEQ ID NO:105:

```
Ser Phe Leu Leu Arg Asn
1               5
```

( 2 ) INFORMATION FOR SEQ ID NO:106:

( i ) SEQUENCE CHARACTERISTICS:

( A ) LENGTH: 14 amino acids
( B ) TYPE: amino acid
( C ) STRANDEDNESS: single
( D ) TOPOLOGY: linear ( x i ) SEQUENCE DESCRIPTION: SEQ ID NO:106:

Ser Phe Leu Leu Arg Asn Pro Asn Asp Lys Tyr Glu Pro Phe
1               5                   10

( 2 ) INFORMATION FOR SEQ ID NO:107:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( x i ) SEQUENCE DESCRIPTION: SEQ ID NO:107:

Phe Ser Leu Leu Arg Asn Pro Asn Asp Lys Tyr Glu Pro Phe
1               5                   10

( 2 ) INFORMATION FOR SEQ ID NO:108:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( x i ) SEQUENCE DESCRIPTION: SEQ ID NO:108:

Phe Ser Leu Leu
1

( 2 ) INFORMATION FOR SEQ ID NO:109:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( x i ) SEQUENCE DESCRIPTION: SEQ ID NO:109:

Ser Phe Leu Leu
1

( 2 ) INFORMATION FOR SEQ ID NO:110:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( x i ) SEQUENCE DESCRIPTION: SEQ ID NO:110:

Leu Leu Arg Asn Pro Asn Asp Lys Tyr Glu Pro Phe
1               5                   10

( 2 ) INFORMATION FOR SEQ ID NO:111:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( x i ) SEQUENCE DESCRIPTION: SEQ ID NO:111:

Ser Phe Leu Leu Arg Asn Pro Asn Asp Lys Tyr Glu
1               5                   10

( 2 ) INFORMATION FOR SEQ ID NO:112:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:112:

```
Ser  Phe  Leu  Leu  Arg  Asn  Pro  Asn  Asp  Lys
1                   5                        10
```

( 2 ) INFORMATION FOR SEQ ID NO:113:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:113:

```
Ser  Phe  Leu  Leu  Arg  Asn  Pro  Asn
1                   5
```

( 2 ) INFORMATION FOR SEQ ID NO:114:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 7
        ( D ) OTHER INFORMATION: /note= "This position is P-NH2."

( x i ) SEQUENCE DESCRIPTION: SEQ ID NO:114:

```
Ser  Phe  Leu  Leu  Arg  Asn  Pro
1                   5
```

( 2 ) INFORMATION FOR SEQ ID NO:115:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 6
        ( D ) OTHER INFORMATION: /note= "This position is N-NH2."

( x i ) SEQUENCE DESCRIPTION: SEQ ID NO:115:

```
Ser  Phe  Leu  Leu  Arg  Asn
1                   5
```

( 2 ) INFORMATION FOR SEQ ID NO:116:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 5
        ( D ) OTHER INFORMATION: /note= "This position is R-NH2."

5,688,768

89

90

-continued ( x i ) SEQUENCE DESCRIPTION: SEQ ID NO:116:

Ser Phe Leu Leu Arg
1                 5

( 2 ) INFORMATION FOR SEQ ID NO:117:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 4
        ( D ) OTHER INFORMATION: /note= "This position is L-NH2."

( x i ) SEQUENCE DESCRIPTION: SEQ ID NO:117:

Ser Phe Leu Leu
1

( 2 ) INFORMATION FOR SEQ ID NO:118:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Ac-S."

( x i ) SEQUENCE DESCRIPTION: SEQ ID NO:118:

Ser Phe Leu Leu Arg Asn Pro Asn Asp Tyr Lys Glu
1                 5                           10

( 2 ) INFORMATION FOR SEQ ID NO:119:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Ac-F."

( x i ) SEQUENCE DESCRIPTION: SEQ ID NO:119:

Phe Leu Leu Arg Asn Pro Asn Asp Lys Tyr Glu Pro Phe
1                 5                           10

( 2 ) INFORMATION FOR SEQ ID NO:120:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( x i ) SEQUENCE DESCRIPTION: SEQ ID NO:120:

Phe Leu Leu Arg Asn Pro Asn Asp Lys Tyr Glu Pro Phe
1                 5                           10

( 2 ) INFORMATION FOR SEQ ID NO:121:

( i ) SEQUENCE CHARACTERISTICS:

(A) LENGTH: 5 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note= "This position is
        [desaminoSer]."

(ix) FEATURE:
(A) NAME/KEY: Modified-site
(B) LOCATION: 5
(D) OTHER INFORMATION: /note= "This position is R-NH2."

(xi) SEQUENCE DESCRIPTION: SEQ ID NO:121:

Xaa Phe Leu Leu Arg
1                 5

(2) INFORMATION FOR SEQ ID NO:122:

(i) SEQUENCE CHARACTERISTICS:
(A) LENGTH: 5 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note= "This position is
        [desaminoAsn]."

(ix) FEATURE:
(A) NAME/KEY: Modified-site
(B) LOCATION: 5
(D) OTHER INFORMATION: /note= "This position is R-NH2."

(xi) SEQUENCE DESCRIPTION: SEQ ID NO:122:

Xaa Phe Leu Leu Arg
1                 5

(2) INFORMATION FOR SEQ ID NO:123:

(i) SEQUENCE CHARACTERISTICS:
(A) LENGTH: 5 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note= "This position is
        [Methylthioacetyl]."

(ix) FEATURE:
(A) NAME/KEY: Modified-site
(B) LOCATION: 5
(D) OTHER INFORMATION: /note= "This position is R-NH2."

(xi) SEQUENCE DESCRIPTION: SEQ ID NO:123:

Xaa Phe Leu Leu Arg
1                 5

(2) INFORMATION FOR SEQ ID NO:124:

(i) SEQUENCE CHARACTERISTICS:
(A) LENGTH: 5 amino acids
(B) TYPE: amino acid
(C) STRANDEDNESS: single
(D) TOPOLOGY: linear ( i x ) FEATURE:
    ( A ) NAME/KEY: Modified-site
    ( B ) LOCATION: 1
    ( D ) OTHER INFORMATION: /note= "This position is
    [ 3- Tetrahydrofuranoyl]."

( i x ) FEATURE:
    ( A ) NAME/KEY: Modified-site
    ( B ) LOCATION: 5
    ( D ) OTHER INFORMATION: /note= "This position is R-NH2."

( x i ) SEQUENCE DESCRIPTION: SEQ ID NO:124:

Xaa Phe Leu Leu Arg
1               5

( 2 ) INFORMATION FOR SEQ ID NO:125:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 2
    ( D ) OTHER INFORMATION: /note= "This position is
    ( N - MePhe )."

( x i ) SEQUENCE DESCRIPTION: SEQ ID NO:125:

Ser Xaa Leu Leu Arg Asn Pro Asn Asp Lys Tyr Glu
1               5                   10

( 2 ) INFORMATION FOR SEQ ID NO:126:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 5
    ( D ) OTHER INFORMATION: /note= "This position is R-NH2."

( x i ) SEQUENCE DESCRIPTION: SEQ ID NO:126:

Asp Phe Leu Leu Arg
1               5

( 2 ) INFORMATION FOR SEQ ID NO:127:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 5
    ( D ) OTHER INFORMATION: /note= "This position is R-NH2."

( x i ) SEQUENCE DESCRIPTION: SEQ ID NO:127:

Lys Phe Leu Leu Arg
1               5

( 2 ) INFORMATION FOR SEQ ID NO:128:

( i ) SEQUENCE CHARACTERISTICS:
    ( A ) LENGTH: 5 amino acids
    ( B ) TYPE: amino acid ( C ) STRANDEDNESS: single
( D ) TOPOLOGY: linear ( i x ) FEATURE:
 ( A ) NAME/KEY: Modified-site
 ( B ) LOCATION: 5
 ( D ) OTHER INFORMATION: /note= "This position is R-NH2."

( x i ) SEQUENCE DESCRIPTION: SEQ ID NO:128:

Phe Phe Leu Leu Arg
1        5

( 2 ) INFORMATION FOR SEQ ID NO:129:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 1
  ( D ) OTHER INFORMATION: /note= "This position is
   [ Acm-Cys]."

( i x ) FEATURE:
  ( A ) NAME/KEY: Modified-site
  ( B ) LOCATION: 5
  ( D ) OTHER INFORMATION: /note= "This position is R-NH2."

( x i ) SEQUENCE DESCRIPTION: SEQ ID NO:129:

Xaa Phe Leu Leu Arg
1        5

( 2 ) INFORMATION FOR SEQ ID NO:130:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 1
  ( D ) OTHER INFORMATION: /note= "This position is
   [ Valeryl]."

( i x ) FEATURE:
  ( A ) NAME/KEY: Modified-site
  ( B ) LOCATION: 5
  ( D ) OTHER INFORMATION: /note= "This position is R-NH2."

( x i ) SEQUENCE DESCRIPTION: SEQ ID NO:130:

Xaa Phe Leu Leu Arg
1        5

( 2 ) INFORMATION FOR SEQ ID NO:131:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 1
  ( D ) OTHER INFORMATION: /note= "This position is
   [ 2- MeButyryl]."

( i x ) FEATURE:
  ( A ) NAME/KEY: Modified-site

-continued

```
            ( B ) LOCATION: 5
            ( D ) OTHER INFORMATION: /note= "This position is R-NH2."

( x i ) SEQUENCE DESCRIPTION: SEQ ID NO:131:

Xaa  Phe  Leu  Leu  Arg
    1                    5
```

( 2 ) INFORMATION FOR SEQ ID NO:132:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is
[ desaminoOrn]."

( i x ) FEATURE:
        ( A ) NAME/KEY: Modified-site
        ( B ) LOCATION: 5
        ( D ) OTHER INFORMATION: /note= "This position is R-NH2."

( x i ) SEQUENCE DESCRIPTION: SEQ ID NO:132:

```
    Xaa  Phe  Leu  Leu  Arg
    1                    5
```

( 2 ) INFORMATION FOR SEQ ID NO:133:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is
[ N- MeSer]."

( x i ) SEQUENCE DESCRIPTION: SEQ ID NO:133:

```
    Xaa  Phe  Leu  Leu  Arg  Asn  Pro  Asn  Asp  Lys  Tyr  Glu
    1                    5                        10
```

( 2 ) INFORMATION FOR SEQ ID NO:134:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 5
        ( D ) OTHER INFORMATION: /note= "This position is R-NH2."

( x i ) SEQUENCE DESCRIPTION: SEQ ID NO:134:

```
    Cys  Phe  Leu  Leu  Arg
    1                    5
```

( 2 ) INFORMATION FOR SEQ ID NO:135:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is
              ( S - M e C y s )."

( i x ) FEATURE:
        ( A ) NAME/KEY: Modified-site
        ( B ) LOCATION: 6
        ( D ) OTHER INFORMATION: /note= "This position is N-NH2."

( x i ) SEQUENCE DESCRIPTION: SEQ ID NO:135:

Xaa Phe Leu Leu Arg Asn
1                   5

( 2 ) INFORMATION FOR SEQ ID NO:136:

( i ) SEQUENCE CHARACTERISTICS:
          ( A ) LENGTH: 5 amino acids
          ( B ) TYPE: amino acid
          ( C ) STRANDEDNESS: single
          ( D ) TOPOLOGY: linear ( i x ) FEATURE:
          ( A ) NAME/KEY: Modified-site
          ( B ) LOCATION: 1
          ( D ) OTHER INFORMATION: /note= "This position is [Beta-Ala]."

( i x ) FEATURE:
          ( A ) NAME/KEY: Modified-site
          ( B ) LOCATION: 5
          ( D ) OTHER INFORMATION: /note= "This position is R-NH2."

( x i ) SEQUENCE DESCRIPTION: SEQ ID NO:136:

Xaa Phe Leu Leu Arg
1                5

( 2 ) INFORMATION FOR SEQ ID NO:137:

( i ) SEQUENCE CHARACTERISTICS:
          ( A ) LENGTH: 5 amino acids
          ( B ) TYPE: amino acid
          ( C ) STRANDEDNESS: single
          ( D ) TOPOLOGY: linear ( i x ) FEATURE:
          ( A ) NAME/KEY: Modified-site
          ( B ) LOCATION: 5
          ( D ) OTHER INFORMATION: /note= "This position is R-NH2."

( x i ) SEQUENCE DESCRIPTION: SEQ ID NO:137:

Gly Phe Leu Leu Arg
1                5

( 2 ) INFORMATION FOR SEQ ID NO:138:

( i ) SEQUENCE CHARACTERISTICS:
          ( A ) LENGTH: 10 amino acids
          ( B ) TYPE: amino acid
          ( C ) STRANDEDNESS: single
          ( D ) TOPOLOGY: linear ( x i ) SEQUENCE DESCRIPTION: SEQ ID NO:138:

Thr Phe Leu Leu Arg Asn Pro Asn Asp Lys
1                5                   10

( 2 ) INFORMATION FOR SEQ ID NO:139:

( i ) SEQUENCE CHARACTERISTICS:
          ( A ) LENGTH: 12 amino acids
          ( B ) TYPE: amino acid ( C ) STRANDEDNESS: single
                ( D ) TOPOLOGY: linear ( x i ) SEQUENCE DESCRIPTION: SEQ ID NO:139:

Ala  Phe  Leu  Leu  Arg  Asn  Pro  Asn  Asp  Lys  Tyr  Glu
    1              5                        10

( 2 ) INFORMATION FOR SEQ ID NO:140:

( i ) SEQUENCE CHARACTERISTICS:
                ( A ) LENGTH: 12 amino acids
                ( B ) TYPE: amino acid
                ( C ) STRANDEDNESS: single
                ( D ) TOPOLOGY: linear ( x i ) SEQUENCE DESCRIPTION: SEQ ID NO:140:

Ser  Ala  Leu  Leu  Arg  Asn  Pro  Asn  Asp  Lys  Tyr  Glu
    1              5                        10

( 2 ) INFORMATION FOR SEQ ID NO:141:

( i ) SEQUENCE CHARACTERISTICS:
                ( A ) LENGTH: 5 amino acids
                ( B ) TYPE: amino acid
                ( C ) STRANDEDNESS: single
                ( D ) TOPOLOGY: linear ( i x ) FEATURE:
                ( A ) NAME/KEY: Modified-site
                ( B ) LOCATION: 5
                ( D ) OTHER INFORMATION: /note= "This position is R-NH2."

( x i ) SEQUENCE DESCRIPTION: SEQ ID NO:141:

Ser  Leu  Leu  Leu  Arg
    1              5

( 2 ) INFORMATION FOR SEQ ID NO:142:

( i ) SEQUENCE CHARACTERISTICS:
                ( A ) LENGTH: 5 amino acids
                ( B ) TYPE: amino acid
                ( C ) STRANDEDNESS: single
                ( D ) TOPOLOGY: linear ( i x ) FEATURE:
                ( A ) NAME/KEY: Modified-site
                ( B ) LOCATION: 5
                ( D ) OTHER INFORMATION: /note= "This position is R-NH2."

( x i ) SEQUENCE DESCRIPTION: SEQ ID NO:142:

Ser  Tyr  Leu  Leu  Arg
    1              5

( 2 ) INFORMATION FOR SEQ ID NO:143:

( i ) SEQUENCE CHARACTERISTICS:
                ( A ) LENGTH: 5 amino acids
                ( B ) TYPE: amino acid
                ( C ) STRANDEDNESS: single
                ( D ) TOPOLOGY: linear ( i x ) FEATURE:
                ( A ) NAME/KEY: Modified-site
                ( B ) LOCATION: 2
                ( D ) OTHER INFORMATION: /note= "This position is
                ( N O 2 P h e )."

( i x ) FEATURE:
                ( A ) NAME/KEY: Modified-site
                ( B ) LOCATION: 5
                ( D ) OTHER INFORMATION: /note= "This position is R-NH2."

( x i ) SEQUENCE DESCRIPTION: SEQ ID NO:143:

Ser Xaa Leu Leu Arg
1                 5

( 2 ) INFORMATION FOR SEQ ID NO:144:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 2
        ( D ) OTHER INFORMATION: /note= "This position is
              ( h o m o P h e )."

( i x ) FEATURE:
        ( A ) NAME/KEY: Modified-site
        ( B ) LOCATION: 5
        ( D ) OTHER INFORMATION: /note= "This position is R-NH2."

( x i ) SEQUENCE DESCRIPTION: SEQ ID NO:144:

Ser Xaa Leu Leu Arg
1                 5

( 2 ) INFORMATION FOR SEQ ID NO:145:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 2
        ( D ) OTHER INFORMATION: /note= "This position is (Phg)."

( i x ) FEATURE:
        ( A ) NAME/KEY: Modified-site
        ( B ) LOCATION: 5
        ( D ) OTHER INFORMATION: /note= "This position is R-NH2."

( x i ) SEQUENCE DESCRIPTION: SEQ ID NO:145:

Ser Xaa Leu Leu Arg
1                 5

( 2 ) INFORMATION FOR SEQ ID NO:146:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 2
        ( D ) OTHER INFORMATION: /note= "This position is (Tic)."

( i x ) FEATURE:
        ( A ) NAME/KEY: Modified-site
        ( B ) LOCATION: 5
        ( D ) OTHER INFORMATION: /note= "This position is R-NH2."

( x i ) SEQUENCE DESCRIPTION: SEQ ID NO:146:

Ser Xaa Leu Leu Arg
1                 5

( 2 ) INFORMATION FOR SEQ ID NO:147:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 2
  ( D ) OTHER INFORMATION: /note= "This position is (Cha)."

( i x ) FEATURE:
  ( A ) NAME/KEY: Modified-site
  ( B ) LOCATION: 5
  ( D ) OTHER INFORMATION: /note= "This position is R-NH2."

( x i ) SEQUENCE DESCRIPTION: SEQ ID NO:147:

Ser Xaa Leu Leu Arg
1               5

( 2 ) INFORMATION FOR SEQ ID NO:148:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 2
  ( D ) OTHER INFORMATION: /note= "This position is (Nal)."

( i x ) FEATURE:
  ( A ) NAME/KEY: Modified-site
  ( B ) LOCATION: 5
  ( D ) OTHER INFORMATION: /note= "This position is R-NH2."

( x i ) SEQUENCE DESCRIPTION: SEQ ID NO:148:

Ser Xaa Leu Leu Arg
1               5

( 2 ) INFORMATION FOR SEQ ID NO:149:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 2
  ( D ) OTHER INFORMATION: /note= "This position is
  ( OMeTyr )."

( i x ) FEATURE:
  ( A ) NAME/KEY: Modified-site
  ( B ) LOCATION: 5
  ( D ) OTHER INFORMATION: /note= "This position is R-NH2."

( x i ) SEQUENCE DESCRIPTION: SEQ ID NO:149:

Ser Xaa Leu Leu Arg
1               5

( 2 ) INFORMATION FOR SEQ ID NO:150:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear (ix) FEATURE:
    (A) NAME/KEY: Modified-site
    (B) LOCATION: 2
    (D) OTHER INFORMATION: /note= "This position is
        (pClPhe)."

(ix) FEATURE:
    (A) NAME/KEY: Modified-site
    (B) LOCATION: 5
    (D) OTHER INFORMATION: /note= "This position is R-NH2."

(xi) SEQUENCE DESCRIPTION: SEQ ID NO:150:

Ser Xaa Leu Leu Arg
1               5

(2) INFORMATION FOR SEQ ID NO:151:

(i) SEQUENCE CHARACTERISTICS:
        (A) LENGTH: 5 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 2
        (D) OTHER INFORMATION: /note= "This position is (Thi)."

(ix) FEATURE:
        (A) NAME/KEY: Modified-site
        (B) LOCATION: 5
        (D) OTHER INFORMATION: /note= "This position is R-NH2."

(xi) SEQUENCE DESCRIPTION: SEQ ID NO:151:

Ser Xaa Leu Leu Arg
1               5

(2) INFORMATION FOR SEQ ID NO:152:

(i) SEQUENCE CHARACTERISTICS:
        (A) LENGTH: 6 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 3
        (D) OTHER INFORMATION: /note= "This position is (b-Ala)."

(ix) FEATURE:
        (A) NAME/KEY: Modified-site
        (B) LOCATION: 6
        (D) OTHER INFORMATION: /note= "This position is N-NH2."

(xi) SEQUENCE DESCRIPTION: SEQ ID NO:152:

Ser Phe Xaa Leu Arg Asn
1                   5

(2) INFORMATION FOR SEQ ID NO:153:

(i) SEQUENCE CHARACTERISTICS:
        (A) LENGTH: 6 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 3
        (D) OTHER INFORMATION: /note= "This position is (Aib)."

(ix) FEATURE:
        (A) NAME/KEY: Modified-site (B) LOCATION: 6
(D) OTHER INFORMATION: /note= "This position is N-NH2."

(xi) SEQUENCE DESCRIPTION: SEQ ID NO:153:

Ser Phe Xaa Leu Arg Asn
1               5

(2) INFORMATION FOR SEQ ID NO:154:

(i) SEQUENCE CHARACTERISTICS:
  (A) LENGTH: 5 amino acids
  (B) TYPE: amino acid
  (C) STRANDEDNESS: single
  (D) TOPOLOGY: linear (ix) FEATURE:
  (A) NAME/KEY: Modified-site
  (B) LOCATION: 5
  (D) OTHER INFORMATION: /note= "This position is R-NH2."

(xi) SEQUENCE DESCRIPTION: SEQ ID NO:154:

Ser Phe Asp Leu Arg
1               5

(2) INFORMATION FOR SEQ ID NO:155:

(i) SEQUENCE CHARACTERISTICS:
  (A) LENGTH: 5 amino acids
  (B) TYPE: amino acid
  (C) STRANDEDNESS: single
  (D) TOPOLOGY: linear (ix) FEATURE:
  (A) NAME/KEY: Modified-site
  (B) LOCATION: 3
  (D) OTHER INFORMATION: /note= "This position is (N-MeLeu)."

(ix) FEATURE:
  (A) NAME/KEY: Modified-site
  (B) LOCATION: 5
  (D) OTHER INFORMATION: /note= "This position is R-NH2."

(xi) SEQUENCE DESCRIPTION: SEQ ID NO:155:

Ser Phe Xaa Leu Arg
1               5

(2) INFORMATION FOR SEQ ID NO:156:

(i) SEQUENCE CHARACTERISTICS:
  (A) LENGTH: 6 amino acids
  (B) TYPE: amino acid
  (C) STRANDEDNESS: single
  (D) TOPOLOGY: linear (ix) FEATURE:
  (A) NAME/KEY: Modified-site
  (B) LOCATION: 6
  (D) OTHER INFORMATION: /note= "This position is N-NH2."

(xi) SEQUENCE DESCRIPTION: SEQ ID NO:156:

Ser Phe His Leu Arg Asn
1               5

(2) INFORMATION FOR SEQ ID NO:157:

(i) SEQUENCE CHARACTERISTICS:
  (A) LENGTH: 12 amino acids
  (B) TYPE: amino acid
  (C) STRANDEDNESS: single
  (D) TOPOLOGY: linear ( x i ) SEQUENCE DESCRIPTION: SEQ ID NO:157:

Ser Phe Ala Leu Arg Asn Pro Asn Asp Lys Tyr Glu
1               5                   10

( 2 ) INFORMATION FOR SEQ ID NO:158:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 5
        ( D ) OTHER INFORMATION: /note= "This position is R-NH2."

( x i ) SEQUENCE DESCRIPTION: SEQ ID NO:158:

Ser Phe Trp Leu Arg
1               5

( 2 ) INFORMATION FOR SEQ ID NO:159:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 5
        ( D ) OTHER INFORMATION: /note= "This position is R-NH2."

( x i ) SEQUENCE DESCRIPTION: SEQ ID NO:159:

Ser Phe Phe Leu Arg
1               5

( 2 ) INFORMATION FOR SEQ ID NO:160:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 6
        ( D ) OTHER INFORMATION: /note= "This position is N-NH2."

( x i ) SEQUENCE DESCRIPTION: SEQ ID NO:160:

Ser Phe Phe Leu Arg Asn
1               5

( 2 ) INFORMATION FOR SEQ ID NO:161:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 3
        ( D ) OTHER INFORMATION: /note= "This position is (Phg)."

( i x ) FEATURE:
        ( A ) NAME/KEY: Modified-site
        ( B ) LOCATION: 5
        ( D ) OTHER INFORMATION: /note= "This position is R-NH2."

( x i ) SEQUENCE DESCRIPTION: SEQ ID NO:161:

Ser Phe Xaa Leu Arg
1               5

( 2 ) INFORMATION FOR SEQ ID NO:162:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i x ) FEATURE:
      ( A ) NAME/KEY: Modified-site
      ( B ) LOCATION: 5
      ( D ) OTHER INFORMATION: /note= "This position is R-NH2."

( x i ) SEQUENCE DESCRIPTION: SEQ ID NO:162:

Ser Phe Pro Leu Arg
1               5

( 2 ) INFORMATION FOR SEQ ID NO:163:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i x ) FEATURE:
      ( A ) NAME/KEY: Modified-site
      ( B ) LOCATION: 5
      ( D ) OTHER INFORMATION: /note= "This position is R-NH2."

( x i ) SEQUENCE DESCRIPTION: SEQ ID NO:163:

Ser Phe Gly Leu Arg
1               5

( 2 ) INFORMATION FOR SEQ ID NO:164:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i x ) FEATURE:
      ( A ) NAME/KEY: Modified-site
      ( B ) LOCATION: 5
      ( D ) OTHER INFORMATION: /note= "This position is R-NH2."

( x i ) SEQUENCE DESCRIPTION: SEQ ID NO:164:

Ser Phe Arg Leu Arg
1               5

( 2 ) INFORMATION FOR SEQ ID NO:165:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i x ) FEATURE:
      ( A ) NAME/KEY: Modified-site
      ( B ) LOCATION: 6
      ( D ) OTHER INFORMATION: /note= "This position is N-NH2."

( x i ) SEQUENCE DESCRIPTION: SEQ ID NO:165:

Ser Phe Tyr Leu Arg Asn 1              5

( 2 ) INFORMATION FOR SEQ ID NO:166:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 5
        ( D ) OTHER INFORMATION: /note= "This position is R-NH2."

( x i ) SEQUENCE DESCRIPTION: SEQ ID NO:166:

Ser  Phe  Ile  Leu  Arg
    1                        5

( 2 ) INFORMATION FOR SEQ ID NO:167:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 3
        ( D ) OTHER INFORMATION: /note= "This position is (Cha)."

( i x ) FEATURE:
        ( A ) NAME/KEY: Modified-site
        ( B ) LOCATION: 5
        ( D ) OTHER INFORMATION: /note= "This position is R-NH2."

( x i ) SEQUENCE DESCRIPTION: SEQ ID NO:167:

Ser  Phe  Xaa  Leu  Arg
    1                        5

( 2 ) INFORMATION FOR SEQ ID NO:168:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 3
        ( D ) OTHER INFORMATION: /note= "This position is (Cha)."

( i x ) FEATURE:
        ( A ) NAME/KEY: Modified-site
        ( B ) LOCATION: 6
        ( D ) OTHER INFORMATION: /note= "This position is N-NH2."

( x i ) SEQUENCE DESCRIPTION: SEQ ID NO:168:

Ser  Phe  Xaa  Leu  Arg  Asn
    1                        5

( 2 ) INFORMATION FOR SEQ ID NO:169:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site (B) LOCATION: 3
(D) OTHER INFORMATION: /note= "This position is (Tic)."

(ix) FEATURE:
(A) NAME/KEY: Modified-site
(B) LOCATION: 6
(D) OTHER INFORMATION: /note= "This position is N-NH2."

(xi) SEQUENCE DESCRIPTION: SEQ ID NO:169:

Ser Phe Xaa Leu Arg Asn
1               5

(2) INFORMATION FOR SEQ ID NO:170:

(i) SEQUENCE CHARACTERISTICS:
(A) LENGTH: 12 amino acids
(B) TYPE: amino acid
(C) STRANDEDNESS: single
(D) TOPOLOGY: linear (xi) SEQUENCE DESCRIPTION: SEQ ID NO:170:

Ser Phe Leu Ala Arg Asn Pro Asn Asp Lys Tyr Glu
1               5                   10

(2) INFORMATION FOR SEQ ID NO:171:

(i) SEQUENCE CHARACTERISTICS:
(A) LENGTH: 5 amino acids
(B) TYPE: amino acid
(C) STRANDEDNESS: single
(D) TOPOLOGY: linear (ix) FEATURE:
(A) NAME/KEY: Modified-site
(B) LOCATION: 5
(D) OTHER INFORMATION: /note= "This position is R-NH2."

(xi) SEQUENCE DESCRIPTION: SEQ ID NO:171:

Ser Phe Leu Pro Arg
1               5

(2) INFORMATION FOR SEQ ID NO:172:

(i) SEQUENCE CHARACTERISTICS:
(A) LENGTH: 5 amino acids
(B) TYPE: amino acid
(C) STRANDEDNESS: single
(D) TOPOLOGY: linear (ix) FEATURE:
(A) NAME/KEY: Modified-site
(B) LOCATION: 5
(D) OTHER INFORMATION: /note= "This position is R-NH2."

(xi) SEQUENCE DESCRIPTION: SEQ ID NO:172:

Ser Phe Leu Glu Arg
1               5

(2) INFORMATION FOR SEQ ID NO:173:

(i) SEQUENCE CHARACTERISTICS:
(A) LENGTH: 5 amino acids
(B) TYPE: amino acid
(C) STRANDEDNESS: single
(D) TOPOLOGY: linear (ix) FEATURE:
(A) NAME/KEY: Modified-site
(B) LOCATION: 5
(D) OTHER INFORMATION: /note= "This position is R-NH2."

(xi) SEQUENCE DESCRIPTION: SEQ ID NO:173:

Ser Phe Leu Ala Arg
1               5

(2) INFORMATION FOR SEQ ID NO:174:

(i) SEQUENCE CHARACTERISTICS:
      (A) LENGTH: 6 amino acids
      (B) TYPE: amino acid
      (C) STRANDEDNESS: single
      (D) TOPOLOGY: linear (ix) FEATURE:
      (A) NAME/KEY: Modified-site
      (B) LOCATION: 6
      (D) OTHER INFORMATION: /note= "This position is N-NH2."

(xi) SEQUENCE DESCRIPTION: SEQ ID NO:174:

Ser Phe Leu Gln Arg Asn
1               5

(2) INFORMATION FOR SEQ ID NO:175:

(i) SEQUENCE CHARACTERISTICS:
      (A) LENGTH: 6 amino acids
      (B) TYPE: amino acid
      (C) STRANDEDNESS: single
      (D) TOPOLOGY: linear (ix) FEATURE:
      (A) NAME/KEY: Modified-site
      (B) LOCATION: 6
      (D) OTHER INFORMATION: /note= "This position is N-NH2."

(xi) SEQUENCE DESCRIPTION: SEQ ID NO:175:

Ser Phe Leu Ile Arg Asn
1               5

(2) INFORMATION FOR SEQ ID NO:176:

(i) SEQUENCE CHARACTERISTICS:
      (A) LENGTH: 5 amino acids
      (B) TYPE: amino acid
      (C) STRANDEDNESS: single
      (D) TOPOLOGY: linear (ix) FEATURE:
      (A) NAME/KEY: Modified-site
      (B) LOCATION: 5
      (D) OTHER INFORMATION: /note= "This position is R-NH2."

(xi) SEQUENCE DESCRIPTION: SEQ ID NO:176:

Ser Phe Leu Phe Arg
1               5

(2) INFORMATION FOR SEQ ID NO:177:

(i) SEQUENCE CHARACTERISTICS:
      (A) LENGTH: 5 amino acids
      (B) TYPE: amino acid
      (C) STRANDEDNESS: single
      (D) TOPOLOGY: linear (ix) FEATURE:
      (A) NAME/KEY: Modified-site
      (B) LOCATION: 5
      (D) OTHER INFORMATION: /note= "This position is R-NH2."

(xi) SEQUENCE DESCRIPTION: SEQ ID NO:177:

Ser Phe Leu Arg Arg
1               5

( 2 ) INFORMATION FOR SEQ ID NO:178:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 4
        ( D ) OTHER INFORMATION: /note= "This position is (Nal)."

( i x ) FEATURE:
        ( A ) NAME/KEY: Modified-site
        ( B ) LOCATION: 6
        ( D ) OTHER INFORMATION: /note= "This position is N-NH2."

( x i ) SEQUENCE DESCRIPTION: SEQ ID NO:178:

Ser Phe Leu Xaa Arg Asn
1                  5

( 2 ) INFORMATION FOR SEQ ID NO:179:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 4
        ( D ) OTHER INFORMATION: /note= "This position is (Cha)."

( i x ) FEATURE:
        ( A ) NAME/KEY: Modified-site
        ( B ) LOCATION: 5
        ( D ) OTHER INFORMATION: /note= "This position is R-NH2."

( x i ) SEQUENCE DESCRIPTION: SEQ ID NO:179:

Ser Phe Leu Xaa Arg
1                  5

( 2 ) INFORMATION FOR SEQ ID NO:180:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 3
        ( D ) OTHER INFORMATION: /note= "This position is (Cha)."

( i x ) FEATURE:
        ( A ) NAME/KEY: Modified-site
        ( B ) LOCATION: 4
        ( D ) OTHER INFORMATION: /note= "This position is (Cha)."

( i x ) FEATURE:
        ( A ) NAME/KEY: Modified-site
        ( B ) LOCATION: 6
        ( D ) OTHER INFORMATION: /note= "This position is N-NH2."

( x i ) SEQUENCE DESCRIPTION: SEQ ID NO:180:

Ser Phe Xaa Xaa Arg Asn
1                  5

( 2 ) INFORMATION FOR SEQ ID NO:181:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 3
    ( D ) OTHER INFORMATION: /note= "This position is (Cha)."

( i x ) FEATURE:
    ( A ) NAME/KEY: Modified-site
    ( B ) LOCATION: 4
    ( D ) OTHER INFORMATION: /note= "This position is (Cha)."

( x i ) SEQUENCE DESCRIPTION: SEQ ID NO:181:

Ser Phe Xaa Xaa Leu Arg Asn Pro Asn Asp Lys
1               5                   10

( 2 ) INFORMATION FOR SEQ ID NO:182:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 6
    ( D ) OTHER INFORMATION: /note= "This position is N-NH2."

( x i ) SEQUENCE DESCRIPTION: SEQ ID NO:182:

Ser Phe Leu Leu Asp Asn
1               5

( 2 ) INFORMATION FOR SEQ ID NO:183:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 5
    ( D ) OTHER INFORMATION: /note= "This position is A-NH2."

( x i ) SEQUENCE DESCRIPTION: SEQ ID NO:183:

Ser Phe Leu Leu Ala
1               5

( 2 ) INFORMATION FOR SEQ ID NO:184:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 6
    ( D ) OTHER INFORMATION: /note= "This position is N-NH2."

( x i ) SEQUENCE DESCRIPTION: SEQ ID NO:184:

Ser Phe Leu Leu Leu Asn
1               5

( 2 ) INFORMATION FOR SEQ ID NO:185:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i x ) FEATURE:
                ( A ) NAME/KEY: Modified-site
                ( B ) LOCATION: 6
                ( D ) OTHER INFORMATION: /note= "This position is N-NH2."

( x i ) SEQUENCE DESCRIPTION: SEQ ID NO:185:

Ser Phe Leu Leu Gln Asn
    1                   5

( 2 ) INFORMATION FOR SEQ ID NO:186:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i x ) FEATURE:
                ( A ) NAME/KEY: Modified-site
                ( B ) LOCATION: 6
                ( D ) OTHER INFORMATION: /note= "This position is N-NH2."

( x i ) SEQUENCE DESCRIPTION: SEQ ID NO:186:

Ser Phe Leu Leu Lys Asn
    1                   5

( 2 ) INFORMATION FOR SEQ ID NO:187:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i x ) FEATURE:
                ( A ) NAME/KEY: Modified-site
                ( B ) LOCATION: 5
                ( D ) OTHER INFORMATION: /note= "This position is Har."

( i x ) FEATURE:
                ( A ) NAME/KEY: Modified-site
                ( B ) LOCATION: 6
                ( D ) OTHER INFORMATION: /note= "This position is N-NH2."

( x i ) SEQUENCE DESCRIPTION: SEQ ID NO:187:

Ser Phe Leu Leu Xaa Asn
    1                   5

( 2 ) INFORMATION FOR SEQ ID NO:188:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i x ) FEATURE:
                ( A ) NAME/KEY: Modified-site
                ( B ) LOCATION: 4
                ( D ) OTHER INFORMATION: /note= "This position is (Cha)."

( i x ) FEATURE:
                ( A ) NAME/KEY: Modified-site
                ( B ) LOCATION: 6
                ( D ) OTHER INFORMATION: /note= "This position is A-NH2."

( x i ) SEQUENCE DESCRIPTION: SEQ ID NO:188:

Ser Phe Phe Xaa Arg Ala
1               5

( 2 ) INFORMATION FOR SEQ ID NO:189:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 3
        ( D ) OTHER INFORMATION: /note= "This position is (Cha)."

( i x ) FEATURE:
        ( A ) NAME/KEY: Modified-site
        ( B ) LOCATION: 4
        ( D ) OTHER INFORMATION: /note= "This position is (Cha)."

( i x ) FEATURE:
        ( A ) NAME/KEY: Modified-site
        ( B ) LOCATION: 6
        ( D ) OTHER INFORMATION: /note= "This position is K-NH2."

( x i ) SEQUENCE DESCRIPTION: SEQ ID NO:189:

Ser Phe Xaa Xaa Arg Lys
1               5

( 2 ) INFORMATION FOR SEQ ID NO:190:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:190:

Leu Asp Pro Arg Pro Phe Leu Leu
1               5

( 2 ) INFORMATION FOR SEQ ID NO:191:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Mpr."

( x i ) SEQUENCE DESCRIPTION: SEQ ID NO:191:

Xaa Phe Leu Leu Arg Asn Pro Asn Asp Lys
1               5                   10

( 2 ) INFORMATION FOR SEQ ID NO:192:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "This position is Mpr."

( i x ) FEATURE:
  ( A ) NAME/KEY: Modified-site
  ( B ) LOCATION: 12
  ( D ) OTHER INFORMATION: /note= "This position is E-NH2."

( x i ) SEQUENCE DESCRIPTION: SEQ ID NO:192:

Xaa Phe Leu Leu Arg Asn Pro Asn Asp Lys Tyr Glu
1               5                       10

( 2 ) INFORMATION FOR SEQ ID NO:193:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 1
  ( D ) OTHER INFORMATION: /note= "This position is Mpr."

( i x ) FEATURE:
  ( A ) NAME/KEY: Modified-site
  ( B ) LOCATION: 5
  ( D ) OTHER INFORMATION: /note= "This position is R-NH2."

( x i ) SEQUENCE DESCRIPTION: SEQ ID NO:193:

Xaa Phe Leu Leu Arg
1               5

( 2 ) INFORMATION FOR SEQ ID NO:194:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 1
  ( D ) OTHER INFORMATION: /note= "This position is Mpr."

( i x ) FEATURE:
  ( A ) NAME/KEY: Modified-site
  ( B ) LOCATION: 6
  ( D ) OTHER INFORMATION: /note= "This position is C-NH2."

( x i ) SEQUENCE DESCRIPTION: SEQ ID NO:194:

Xaa Phe Leu Leu Arg Cys
1               5

( 2 ) INFORMATION FOR SEQ ID NO:195:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 1
  ( D ) OTHER INFORMATION: /note= "This position is Mpr."

( i x ) FEATURE:
  ( A ) NAME/KEY: Modified-site
  ( B ) LOCATION: 7
  ( D ) OTHER INFORMATION: /note= "This position is C-NH2."

( x i ) SEQUENCE DESCRIPTION: SEQ ID NO:195:

Xaa Phe Leu Leu Arg Asn Cys (2) INFORMATION FOR SEQ ID NO:196:

(i) SEQUENCE CHARACTERISTICS:
        (A) LENGTH: 9 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "This position is Mpr."

(ix) FEATURE:
        (A) NAME/KEY: Modified-site
        (B) LOCATION: 9
        (D) OTHER INFORMATION: /note= "This position is C-NH2."

(xi) SEQUENCE DESCRIPTION: SEQ ID NO:196:

Xaa Phe Leu Leu Arg Asn Pro Asn Cys
1                         5

(2) INFORMATION FOR SEQ ID NO:197:

(i) SEQUENCE CHARACTERISTICS:
        (A) LENGTH: 10 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "This position is Mpr."

(ix) FEATURE:
        (A) NAME/KEY: Modified-site
        (B) LOCATION: 3
        (D) OTHER INFORMATION: /note= "This position is (Cha)."

(ix) FEATURE:
        (A) NAME/KEY: Modified-site
        (B) LOCATION: 4
        (D) OTHER INFORMATION: /note= "This position is (Cha)."

(ix) FEATURE:
        (A) NAME/KEY: Modified-site
        (B) LOCATION: 10
        (D) OTHER INFORMATION: /note= "This position is K-NH2."

(xi) SEQUENCE DESCRIPTION: SEQ ID NO:197:

Xaa Phe Xaa Xaa Arg Phe Pro Asn Asp Lys
1                         5                       10

(2) INFORMATION FOR SEQ ID NO:198:

(i) SEQUENCE CHARACTERISTICS:
        (A) LENGTH: 10 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "This position is Mpr."

(ix) FEATURE:
        (A) NAME/KEY: Modified-site
        (B) LOCATION: 3
        (D) OTHER INFORMATION: /note= "This position is (Cha)."

(ix) FEATURE:

( A ) NAME/KEY: Modified-site
                    ( B ) LOCATION: 4
                    ( D ) OTHER INFORMATION: /note= "This position is (Cha)."

( i x ) FEATURE:
                    ( A ) NAME/KEY: Modified-site
                    ( B ) LOCATION: 10
                    ( D ) OTHER INFORMATION: /note= "This position is K-NH2."

( x i ) SEQUENCE DESCRIPTION: SEQ ID NO:198:

Xaa  Phe  Xaa  Xaa  Arg  Asn  Pro  Asn  Ala  Lys
        1                   5                        10

( 2 ) INFORMATION FOR SEQ ID NO:199:

( i ) SEQUENCE CHARACTERISTICS:
                    ( A ) LENGTH: 5 amino acids
                    ( B ) TYPE: amino acid
                    ( C ) STRANDEDNESS: single
                    ( D ) TOPOLOGY: linear ( i x ) FEATURE:
                    ( A ) NAME/KEY: Modified-site
                    ( B ) LOCATION: 1
                    ( D ) OTHER INFORMATION: /note= "This position is
                            [ Sme-Mpr]."

( i x ) FEATURE:
                    ( A ) NAME/KEY: Modified-site
                    ( B ) LOCATION: 5
                    ( D ) OTHER INFORMATION: /note= "This position is R-NH2."

( x i ) SEQUENCE DESCRIPTION: SEQ ID NO:199:

Xaa  Phe  Leu  Leu  Arg
        1                   5

( 2 ) INFORMATION FOR SEQ ID NO:200:

( i ) SEQUENCE CHARACTERISTICS:
                    ( A ) LENGTH: 5 amino acids
                    ( B ) TYPE: amino acid
                    ( C ) STRANDEDNESS: single
                    ( D ) TOPOLOGY: linear ( i x ) FEATURE:
                    ( A ) NAME/KEY: Modified-site
                    ( B ) LOCATION: 1
                    ( D ) OTHER INFORMATION: /note= "This position is
                            [ Cam-Mpr]."

( i x ) FEATURE:
                    ( A ) NAME/KEY: Modified-site
                    ( B ) LOCATION: 5
                    ( D ) OTHER INFORMATION: /note= "This position is R-NH2."

( x i ) SEQUENCE DESCRIPTION: SEQ ID NO:200:

Xaa  Phe  Leu  Leu  Arg
        1                   5

( 2 ) INFORMATION FOR SEQ ID NO:201:

( i ) SEQUENCE CHARACTERISTICS:
                    ( A ) LENGTH: 5 amino acids
                    ( B ) TYPE: amino acid
                    ( C ) STRANDEDNESS: single
                    ( D ) TOPOLOGY: linear ( i x ) FEATURE:
                    ( A ) NAME/KEY: Modified-site
                    ( B ) LOCATION: 1
                    ( D ) OTHER INFORMATION: /note= "This position is Mvl."

( i x ) FEATURE:
                    ( A ) NAME/KEY: Modified-site (B) LOCATION: 5
(D) OTHER INFORMATION: /note= "This position is R-NH2."

( x i ) SEQUENCE DESCRIPTION: SEQ ID NO:201:

Xaa Phe Leu Leu Arg
1               5

( 2 ) INFORMATION FOR SEQ ID NO:202:

( i ) SEQUENCE CHARACTERISTICS:
(A) LENGTH: 5 amino acids
(B) TYPE: amino acid
(C) STRANDEDNESS: single
(D) TOPOLOGY: linear ( i x ) FEATURE:
(A) NAME/KEY: Modified-site
(B) LOCATION: 1
(D) OTHER INFORMATION: /note= "This position is Pivaloyl."

( i x ) FEATURE:
(A) NAME/KEY: Modified-site
(B) LOCATION: 5
(D) OTHER INFORMATION: /note= "This position is R-NH2."

( x i ) SEQUENCE DESCRIPTION: SEQ ID NO:202:

Xaa Phe Leu Leu Arg
1               5

( 2 ) INFORMATION FOR SEQ ID NO:203:

( i ) SEQUENCE CHARACTERISTICS:
(A) LENGTH: 10 amino acids
(B) TYPE: amino acid
(C) STRANDEDNESS: single
(D) TOPOLOGY: linear ( i x ) FEATURE:
(A) NAME/KEY: Modified-site
(B) LOCATION: 1
(D) OTHER INFORMATION: /note= "This position is (2-Mba)."

( i x ) FEATURE:
(A) NAME/KEY: Modified-site
(B) LOCATION: 3
(D) OTHER INFORMATION: /note= "This position is (Cha)."

( i x ) FEATURE:
(A) NAME/KEY: Modified-site
(B) LOCATION: 4
(D) OTHER INFORMATION: /note= "This position is (Cha)."

( i x ) FEATURE:
(A) NAME/KEY: Modified-site
(B) LOCATION: 10
(D) OTHER INFORMATION: /note= "This position is K-NH2."

( x i ) SEQUENCE DESCRIPTION: SEQ ID NO:203:

Xaa Phe Xaa Xaa Arg Lys Pro Asn Asp Lys
1               5                   10

( 2 ) INFORMATION FOR SEQ ID NO:204:

( i ) SEQUENCE CHARACTERISTICS:
(A) LENGTH: 9 amino acids
(B) TYPE: amino acid
(C) STRANDEDNESS: single
(D) TOPOLOGY: linear ( i x ) FEATURE:
(A) NAME/KEY: Modified-site
(B) LOCATION: 1
(D) OTHER INFORMATION: /note= "This position is Mpr."

( i x ) FEATURE:
    ( A ) NAME/KEY: Modified-site
    ( B ) LOCATION: 3
    ( D ) OTHER INFORMATION: /note= "This position is (Cha)."

( i x ) FEATURE:
    ( A ) NAME/KEY: Modified-site
    ( B ) LOCATION: 4
    ( D ) OTHER INFORMATION: /note= "This position is (Cha)."

( x i ) SEQUENCE DESCRIPTION: SEQ ID NO:204:

Xaa Phe Xaa Xaa Arg Asn Pro Asn Asp
1               5

( 2 ) INFORMATION FOR SEQ ID NO:205:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:205:

Asp His Phe Arg
1

( 2 ) INFORMATION FOR SEQ ID NO:206:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( x i ) SEQUENCE DESCRIPTION: SEQ ID NO:206:

Pro Glu Ser Lys Ala Thr Asn Ala Thr Leu Asp Pro Arg Ser Phe Leu
1               5                   10                  15
Leu Cys ( 2 ) INFORMATION FOR SEQ ID NO:207:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( x i ) SEQUENCE DESCRIPTION: SEQ ID NO:207:

Tyr Glu Pro Phe Trp Glu Asp Glu Glu Lys Asn Glu Ser Gly Leu Thr
1               5                   10                  15
Glu Tyr Cys ( 2 ) INFORMATION FOR SEQ ID NO:208:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( x i ) SEQUENCE DESCRIPTION: SEQ ID NO:208:

Pro Glu Ser Lys Ala Thr Asn Ala Thr Leu Asp Pro Arg Ser Phe Leu
1               5                   10                  15
Leu Arg Asn Pro Asn Asp Lys Tyr Glu Pro Phe Trp Glu Asp Glu Glu
                20                  25                  30
Lys Asn Glu Ser Gly Leu Thr Glu Cys (2) INFORMATION FOR SEQ ID NO:209:

(i) SEQUENCE CHARACTERISTICS:
(A) LENGTH: 37 amino acids
(B) TYPE: amino acid
(C) STRANDEDNESS: single
(D) TOPOLOGY: linear (xi) SEQUENCE DESCRIPTION: SEQ ID NO:209:

```
Arg Pro Glu Ser Lys Ala Thr Asn Ala Thr Leu Asp Pro Arg Ser Phe
 1               5                  10                  15
Leu Leu Arg Asn Pro Asn Asp Lys Tyr Glu Pro Phe Trp Glu Asp Glu
            20                  25                  30
Glu Lys Asn Glu Ser
            35
```

(2) INFORMATION FOR SEQ ID NO:210:

(i) SEQUENCE CHARACTERISTICS:
(A) LENGTH: 40 amino acids
(B) TYPE: amino acid
(C) STRANDEDNESS: single
(D) TOPOLOGY: linear (xi) SEQUENCE DESCRIPTION: SEQ ID NO:210:

```
Pro Glu Ser Lys Ala Thr Asn Ala Thr Leu Asp Pro Arg Ser Phe Leu
 1               5                  10                  15
Leu Arg Asn Pro Asn Asp Lys Tyr Glu Pro Phe Trp Glu Asp Glu Glu
            20                  25                  30
Lys Asn Glu Ser Gly Leu Thr Glu
            35                  40
```

(2) INFORMATION FOR SEQ ID NO:211:

(i) SEQUENCE CHARACTERISTICS:
(A) LENGTH: 17 amino acids
(B) TYPE: amino acid
(C) STRANDEDNESS: single
(D) TOPOLOGY: linear (xi) SEQUENCE DESCRIPTION: SEQ ID NO:211:

```
Pro Glu Ser Lys Ala Thr Asn Ala Thr Leu Asp Pro Arg Ser Phe Leu
 1               5                  10                  15
Leu
```

(2) INFORMATION FOR SEQ ID NO:212:

(i) SEQUENCE CHARACTERISTICS:
(A) LENGTH: 18 amino acids
(B) TYPE: amino acid
(C) STRANDEDNESS: single
(D) TOPOLOGY: linear (xi) SEQUENCE DESCRIPTION: SEQ ID NO:212:

```
Tyr Glu Pro Phe Trp Glu Asp Glu Glu Lys Asn Glu Ser Gly Leu Thr
 1               5                  10                  15
Glu Tyr
```

(2) INFORMATION FOR SEQ ID NO:213:

(i) SEQUENCE CHARACTERISTICS:
(A) LENGTH: 16 amino acids
(B) TYPE: amino acid (C) STRANDEDNESS: single
(D) TOPOLOGY: linear (xi) SEQUENCE DESCRIPTION: SEQ ID NO:213:

| Tyr | Tyr | Phe | Ser | Gly | Ser | Asp | Trp | Gln | Phe | Gly | Ser | Glu | Leu | Cys | Arg |
|---|---|---|---|---|---|---|---|---|---|---|---|---|---|---|---|
| 1 | | | | 5 | | | | | 10 | | | | | 15 | |

(2) INFORMATION FOR SEQ ID NO:214:

(i) SEQUENCE CHARACTERISTICS:
(A) LENGTH: 26 amino acids
(B) TYPE: amino acid
(C) STRANDEDNESS: single
(D) TOPOLOGY: linear (xi) SEQUENCE DESCRIPTION: SEQ ID NO:214:

| Lys | Glu | Gln | Thr | Ile | Gln | Val | Pro | Gly | Leu | Asn | Ile | Thr | Thr | Cys | His |
|---|---|---|---|---|---|---|---|---|---|---|---|---|---|---|---|
| 1 | | | | 5 | | | | | 10 | | | | | 15 | |

| Asp | Val | Leu | Asn | Glu | Thr | Leu | Leu | Glu | Gly |
|---|---|---|---|---|---|---|---|---|---|
| | | | 20 | | | | | 25 | |

(2) INFORMATION FOR SEQ ID NO:215:

(i) SEQUENCE CHARACTERISTICS:
(A) LENGTH: 11 amino acids
(B) TYPE: amino acid
(C) STRANDEDNESS: single
(D) TOPOLOGY: linear (xi) SEQUENCE DESCRIPTION: SEQ ID NO:215:

| His | Tyr | Ser | Phe | Leu | Ser | His | Thr | Ser | Thr | Thr |
|---|---|---|---|---|---|---|---|---|---|---|
| 1 | | | | 5 | | | | | 10 | |

(2) INFORMATION FOR SEQ ID NO:216:

(i) SEQUENCE CHARACTERISTICS:
(A) LENGTH: 16 amino acids
(B) TYPE: amino acid
(C) STRANDEDNESS: single
(D) TOPOLOGY: linear (xi) SEQUENCE DESCRIPTION: SEQ ID NO:216:

| Tyr | Tyr | Phe | Ser | Gly | Ser | Asp | Trp | Gln | Phe | Gly | Ser | Glu | Leu | Cys | Arg |
|---|---|---|---|---|---|---|---|---|---|---|---|---|---|---|---|
| 1 | | | | 5 | | | | | 10 | | | | | 15 | |

(2) INFORMATION FOR SEQ ID NO:217:

(i) SEQUENCE CHARACTERISTICS:
(A) LENGTH: 26 amino acids
(B) TYPE: amino acid
(C) STRANDEDNESS: single
(D) TOPOLOGY: linear (xi) SEQUENCE DESCRIPTION: SEQ ID NO:217:

| Lys | Glu | Gln | Thr | Ile | Gln | Val | Pro | Gly | Leu | Asn | Ile | Thr | Thr | Cys | His |
|---|---|---|---|---|---|---|---|---|---|---|---|---|---|---|---|
| 1 | | | | 5 | | | | | 10 | | | | | 15 | |

| Asp | Val | Leu | Asn | Glu | Thr | Leu | Leu | Glu | Gly |
|---|---|---|---|---|---|---|---|---|---|
| | | | 20 | | | | | 25 | |

(2) INFORMATION FOR SEQ ID NO:218:

(i) SEQUENCE CHARACTERISTICS:
(A) LENGTH: 11 amino acids
(B) TYPE: amino acid
(C) STRANDEDNESS: single
(D) TOPOLOGY: linear (xi) SEQUENCE DESCRIPTION: SEQ ID NO:218:

His Tyr Ser Phe Leu Ser His Thr Ser Thr Thr
1               5                    10

( 2 ) INFORMATION FOR SEQ ID NO:219:

( i ) SEQUENCE CHARACTERISTICS:
       ( A ) LENGTH: 3480 base pairs
       ( B ) TYPE: nucleic acid
       ( C ) STRANDEDNESS: single
       ( D ) TOPOLOGY: linear ( i x ) FEATURE:
       ( A ) NAME/KEY: CDS
       ( B ) LOCATION: 225..1499

( x i ) SEQUENCE DESCRIPTION: SEQ ID NO:219:

```
GCGCCCGCGC GACCGCGCGC CCCAGTCCCG CCCCGCCCCG CTAACCGCCC CAGACACAGC        60

GCTCGCCGAG GGTCGCTTGG ACCCTGATCT TACCCGTGGG CACCCTGCGC TCTGCCTGCC       120

GCGAAGACCG GCTCCCCGAC CCGCAGAAGT CAGGAGAGAG GGTGAAGCGG AGCAGCCCGA       180

GGCGGGGCAG CCTCCCGGAG CAGCGCCGCG CAGAGCCCGG GACA ATG GGG CCG CGG       236
                                                  Met Gly Pro Arg
                                                   1

CGG CTG CTG CTG GTG GCC GCC TGC TTC AGT CTG TGC GGC CCG CTG TTG       284
Arg Leu Leu Leu Val Ala Ala Cys Phe Ser Leu Cys Gly Pro Leu Leu
 5               10                  15                  20

TCT GCC CGC ACC CGG GCC CGC AGG CCA GAA TCA AAA GCA ACA AAT GCC       332
Ser Ala Arg Thr Arg Ala Arg Arg Pro Glu Ser Lys Ala Thr Asn Ala
             25                  30                  35

ACC TTA GAT CCC CGG TCA TTT CTT CTC AGG AAC CCC AAT GAT AAA TAT       380
Thr Leu Asp Pro Arg Ser Phe Leu Leu Arg Asn Pro Asn Asp Lys Tyr
         40                  45                  50

GAA CCA TTT TGG GAG GAT GAG GAG AAA AAT GAA AGT GGG TTA ACT GAA       428
Glu Pro Phe Trp Glu Asp Glu Glu Lys Asn Glu Ser Gly Leu Thr Glu
     55                  60                  65

TAC AGA TTA GTC TCC ATC AAT AAA AGC AGT CCT CTT CAA AAA CAA CTT       476
Tyr Arg Leu Val Ser Ile Asn Lys Ser Ser Pro Leu Gln Lys Gln Leu
 70                  75                  80

CCT GCA TTC ATC TCA GAA GAT GCC TCC GGA TAT TTG ACC AGC TCC TGG       524
Pro Ala Phe Ile Ser Glu Asp Ala Ser Gly Tyr Leu Thr Ser Ser Trp
 85               90                  95                 100

CTG ACA CTC TTT GTC CCA TCT GTG TAC ACC GGA GTG TTT GTA GTC AGC       572
Leu Thr Leu Phe Val Pro Ser Val Tyr Thr Gly Val Phe Val Val Ser
             105                 110                 115

CTC CCA CTA AAC ATC ATG GCC ATC GTT GTG TTC ATC CTG AAA ATG AAG       620
Leu Pro Leu Asn Ile Met Ala Ile Val Val Phe Ile Leu Lys Met Lys
         120                 125                 130

GTC AAG AAG CCG GCG GTG GTG TAC ATG CTG CAC CTG GCC ACG GCA GAT       668
Val Lys Lys Pro Ala Val Val Tyr Met Leu His Leu Ala Thr Ala Asp
     135                 140                 145

GTG CTG TTT GTG TCT GTG CTC CCC TTT AAG ATC AGC TAT TAC TTT TCC       716
Val Leu Phe Val Ser Val Leu Pro Phe Lys Ile Ser Tyr Tyr Phe Ser
 150                 155                 160

GGC AGT GAT TGG CAG TTT GGG TCT GAA TTG TGT CGC TTC GTC ACT GCA       764
Gly Ser Asp Trp Gln Phe Gly Ser Glu Leu Cys Arg Phe Val Thr Ala
 165                 170                 175                 180

GCA TTT TAC TGT AAC ATG TAC GCC TCT ATC TTG CTC ATG ACA GTC ATA       812
Ala Phe Tyr Cys Asn Met Tyr Ala Ser Ile Leu Leu Met Thr Val Ile
             185                 190                 195

AGC ATT GAC CGG TTT CTG GCT GTG GTG TAT CCC ATG CAG TCC CTC TCC       860
Ser Ile Asp Arg Phe Leu Ala Val Val Tyr Pro Met Gln Ser Leu Ser
```

-continued

|  |  |  |  |  |  |  |  |  |  |  |  |  |  |  |  |  |
|---|---|---|---|---|---|---|---|---|---|---|---|---|---|---|---|---|
|  |  | 200 |  |  |  |  | 205 |  |  |  |  | 210 |  |  |  |  |
| TGG | CGT | ACT | CTG | GGA | AGG | GCT | TCC | TTC | ACT | TGT | CTG | GCC | ATC | TGG | GCT | 908 |
| Trp | Arg | Thr | Leu | Gly | Arg | Ala | Ser | Phe | Thr | Cys | Leu | Ala | Ile | Trp | Ala |  |
|  |  | 215 |  |  |  |  | 220 |  |  |  |  | 225 |  |  |  |  |
| TTG | GCC | ATC | GCA | GGG | GTA | GTG | CCT | CTC | GTC | CTC | AAG | GAG | CAA | ACC | ATC | 956 |
| Leu | Ala | Ile | Ala | Gly | Val | Val | Pro | Leu | Val | Leu | Lys | Glu | Gln | Thr | Ile |  |
|  |  | 230 |  |  |  |  | 235 |  |  |  |  | 240 |  |  |  |  |
| CAG | GTG | CCC | GGG | CTC | AAC | ATC | ACT | ACC | TGT | CAT | GAT | GTG | CTC | AAT | GAA | 1004 |
| Gln | Val | Pro | Gly | Leu | Asn | Ile | Thr | Thr | Cys | His | Asp | Val | Leu | Asn | Glu |  |
| 245 |  |  |  |  | 250 |  |  |  |  | 255 |  |  |  |  | 260 |  |
| ACC | CTG | CTC | GAA | GGC | TAC | TAT | GCC | TAC | TAC | TTC | TCA | GCC | TTC | TCT | GCT | 1052 |
| Thr | Leu | Leu | Glu | Gly | Tyr | Tyr | Ala | Tyr | Tyr | Phe | Ser | Ala | Phe | Ser | Ala |  |
|  |  |  |  | 265 |  |  |  |  | 270 |  |  |  |  | 275 |  |  |
| GTC | TTC | TTT | TTT | GTG | CCG | CTG | ATC | ATT | TCC | ACG | GTC | TGT | TAT | GTG | TCT | 1100 |
| Val | Phe | Phe | Phe | Val | Pro | Leu | Ile | Ile | Ser | Thr | Val | Cys | Tyr | Val | Ser |  |
|  |  |  | 280 |  |  |  |  | 285 |  |  |  |  | 290 |  |  |  |
| ATC | ATT | CGA | TGT | CTT | AGC | TCT | TCC | GCA | GTT | GCC | AAC | CGC | AGC | AAG | AAG | 1148 |
| Ile | Ile | Arg | Cys | Leu | Ser | Ser | Ser | Ala | Val | Ala | Asn | Arg | Ser | Lys | Lys |  |
|  |  | 295 |  |  |  |  | 300 |  |  |  |  | 305 |  |  |  |  |
| TCC | CGG | GCT | TTG | TTC | CTG | TCA | GCT | GCT | GTT | TTC | TGC | ATC | TTC | ATC | ATT | 1196 |
| Ser | Arg | Ala | Leu | Phe | Leu | Ser | Ala | Ala | Val | Phe | Cys | Ile | Phe | Ile | Ile |  |
|  | 310 |  |  |  |  | 315 |  |  |  |  | 320 |  |  |  |  |  |
| TGC | TTC | GGA | CCC | ACA | AAC | GTC | CTC | CTG | ATT | GCG | CAT | TAC | TCA | TTC | CTT | 1244 |
| Cys | Phe | Gly | Pro | Thr | Asn | Val | Leu | Leu | Ile | Ala | His | Tyr | Ser | Phe | Leu |  |
| 325 |  |  |  |  | 330 |  |  |  |  | 335 |  |  |  |  | 340 |  |
| TCT | CAC | ACT | TCC | ACC | ACA | GAG | GCT | GCC | TAC | TTT | GCC | TAC | CTC | CTC | TGT | 1292 |
| Ser | His | Thr | Ser | Thr | Thr | Glu | Ala | Ala | Tyr | Phe | Ala | Tyr | Leu | Leu | Cys |  |
|  |  |  |  | 345 |  |  |  |  | 350 |  |  |  |  | 355 |  |  |
| GTC | TGT | GTC | AGC | AGC | ATA | AGC | TCG | TGC | ATC | GAC | CCC | CTA | ATT | TAC | TAT | 1340 |
| Val | Cys | Val | Ser | Ser | Ile | Ser | Ser | Cys | Ile | Asp | Pro | Leu | Ile | Tyr | Tyr |  |
|  |  |  | 360 |  |  |  |  | 365 |  |  |  |  | 370 |  |  |  |
| TAC | GCT | TCC | TCT | GAG | TGC | CAG | AGG | TAC | GTC | TAC | AGT | ATC | TTA | TGC | TGC | 1388 |
| Tyr | Ala | Ser | Ser | Glu | Cys | Gln | Arg | Tyr | Val | Tyr | Ser | Ile | Leu | Cys | Cys |  |
|  |  | 375 |  |  |  |  | 380 |  |  |  |  | 385 |  |  |  |  |
| AAA | GAA | AGT | TCC | GAT | CCC | AGC | AGT | TAT | AAC | AGC | AGT | GGG | CAG | TTG | ATG | 1436 |
| Lys | Glu | Ser | Ser | Asp | Pro | Ser | Ser | Tyr | Asn | Ser | Ser | Gly | Gln | Leu | Met |  |
|  | 390 |  |  |  |  | 395 |  |  |  |  | 400 |  |  |  |  |  |
| GCA | AGT | AAA | ATG | GAT | ACC | TGC | TCT | AGT | AAC | CTG | AAT | AAC | AGC | ATA | TAC | 1484 |
| Ala | Ser | Lys | Met | Asp | Thr | Cys | Ser | Ser | Asn | Leu | Asn | Asn | Ser | Ile | Tyr |  |
| 405 |  |  |  | 410 |  |  |  |  | 415 |  |  |  |  | 420 |  |  |
| AAA | AAG | CTG | TTA | ACT | TAGGAAAAGG | GACTGCTGGG | AGGTTAAAAA | GAAAAGTTTA |  |  |  |  |  |  |  | 1539 |
| Lys | Lys | Leu | Leu | Thr |  |  |  |  |  |  |  |  |  |  |  |  |
|  |  |  |  | 425 |  |  |  |  |  |  |  |  |  |  |  |  |

| TAAAAGTGAA | TAACCTGAGG | ATTCTATTAG | TCCCCACCCA | AACTTTATTG | ATTCACCTCC | 1599 |
|---|---|---|---|---|---|---|
| TAAAACAACA | GATGTACGAC | TTGCATACCT | GCTTTTATG | GGAGCTGTCA | AGCATGTATT | 1659 |
| TTTGTCAATT | ACCAGAAAGA | TAACAGGACG | AGATGACGGT | GTTATTCCAA | GGGAATATTG | 1719 |
| CCAATGCTAC | AGTAATAAAT | GAATGTCACT | TCTGGATATA | GCTAGGTGAC | ATATACATAC | 1779 |
| TTACATGTGT | GTATATGTAG | ATGTATGCAC | ACACATATAT | TATTTGCAGT | GCAGTATAGA | 1839 |
| ATAGGCACTT | TAAAACACTC | TTTCCCCGCA | CCCCAGCAAT | TATGAAAATA | ATCTCTGATT | 1899 |
| CCCTGATTTA | ATATGCAAAG | TCTAGGTTGG | TAGAGTTTAG | CCCTGAACAT | TCATGGTGT | 1959 |
| TCATCAACAG | TGAGAGACTC | CATAGTTTGG | GCTTGTACCA | CTTTTGCAAA | TAAGTGTATT | 2019 |
| TTGAAATTGT | TTGACGGCAA | GGTTTAAGTT | ATTAAGAGGT | AAGACTTAGT | ACTATCTGTG | 2079 |
| CGTAGAAGTT | CTAGTGTTTT | CAATTTTAAA | CATATCCAAG | TTTGAATTCC | TAAAATTATG | 2139 |
| GAAACAGATG | AAAAGCCTCT | GTTTTGATAT | GGGTAGTATT | TTTTACATTT | TACACACTGT | 2199 |

-continued

| | | | | | |
|---|---|---|---|---|---|
| ACACATAAGC | CAAAACTGAG | CATAAGTCCT | CTAGTGAATG | TAGGCTGGCT | TTCAGAGTAG | 2259 |
| GCTATTCCTG | AGAGCTGCAT | GTGTCCGCCC | CCGATGGAGG | ACTCCAGGCA | GCAGACACAT | 2319 |
| GCCAGGGCCA | TGTCAGACAC | AGATTGGCCA | GAAACCTTCC | TGCTGAGCCT | CACAGCAGTG | 2379 |
| AGACTGGGGC | CACTACATTT | GCTCCATCCT | CCTGGGATTG | GCTGTGAACT | GATCATGTTT | 2439 |
| ATGAGAAACT | GGCAAAGCAG | AATGTGATAT | CCTAGGAGGT | AATGACCATG | AAAGACTTCT | 2499 |
| CTACCCATCT | TAAAAACAAC | GAAGAAGGC | ATGGACTTCT | GGATGCCCAT | CCACTGGGTG | 2559 |
| TAAACACATC | TAGTAGTTGT | TCTGAAATGT | CAGTTCTGAT | ATGGAAGCAC | CCATTATGCG | 2619 |
| CTGTGGCCAC | TCCAATAGGT | GCTGAGTGTA | CAGAGTGGAA | TAAGACAGAG | ACCTGCCCTC | 2679 |
| AAGAGCAAAG | TAGATCATGC | ATAGAGTGTG | ATGTATGTGT | AATAAATATG | TTTCACACAA | 2739 |
| ACAAGGCCTG | TCAGCTAAAG | AAGTTTGAAC | ATTTGGGTTA | CTATTTCTTG | TGGTTATAAC | 2799 |
| TTAATGAAAA | CAATGCAGTA | CAGGACATAT | ATTTTTAAA | ATAAGTCTGA | TTTAATTGGG | 2859 |
| CACTATTTAT | TTACAAATGT | TTTGCTCAAT | AGATTGCTCA | AATCAGGTTT | TCTTTTAAGA | 2919 |
| ATCAATCATG | TCAGTCTGCT | TAGAAATAAC | AGAAGAAAAT | AGAATTGACA | TTGAAATCTA | 2979 |
| GGAAAATTAT | TCTATAATTT | CCATTTACTT | AAGACTTAAT | GAGACTTTAA | AAGCATTTTT | 3039 |
| TAACCTCCTA | AGTATCAAGT | ATAGAAAATC | TTCATGGAAT | TCACAAAGTA | ATTTGGAAAT | 3099 |
| TAGGTTGAAA | CATATCTCTT | ATCTTACGAA | AAAATGGTAG | CATTTAAAC | AAAATAGAAA | 3159 |
| GTTGCAAGGC | AAATGTTTAT | TTAAAAGAGC | AGGCCAGGCG | CGGTGGCTCA | CGCCTGTAAT | 3219 |
| CCCAGCACTT | TGGGAGGCTG | AGGCGGGTGG | ATCACGAGGT | CAGGAGATCG | AGACCATCCT | 3279 |
| GGCTAACACG | GTGAAACCCG | TCTCTACTAA | AAATGCAAAA | AAAATTAGCC | GGGCGTGGTG | 3339 |
| GCAGGCACCT | GTAGTCCCAG | CTACTCGGGA | GGCTGAGGCA | GGAGACTGGC | GTGAACCCAG | 3399 |
| GAGGCGGACC | TTGTAGTGAG | CCGAGATCGC | GCCACTGTGC | TCCAGCCTGG | GCAACAGAGC | 3459 |
| AAGACTCCAT | CTCAAAAAAA | A | | | | 3480 |

( 2 ) INFORMATION FOR SEQ ID NO:220:

( i ) SEQUENCE CHARACTERISTICS:
        ( A ) LENGTH: 425 amino acids
        ( B ) TYPE: amino acid
        ( D ) TOPOLOGY: linear ( i i ) MOLECULE TYPE: protein ( x i ) SEQUENCE DESCRIPTION: SEQ ID NO:220:

```
Met Gly Pro Arg Arg Leu Leu Leu Val Ala Ala Cys Phe Ser Leu Cys
1               5                   10                  15

Gly Pro Leu Leu Ser Ala Arg Thr Arg Ala Arg Arg Pro Glu Ser Lys
            20                  25                  30

Ala Thr Asn Ala Thr Leu Asp Pro Arg Ser Phe Leu Leu Arg Asn Pro
            35                  40                  45

Asn Asp Lys Tyr Glu Pro Phe Trp Glu Asp Glu Lys Asn Glu Ser
    50                  55                  60

Gly Leu Thr Glu Tyr Arg Leu Val Ser Ile Asn Lys Ser Ser Pro Leu
65                  70                  75                  80

Gln Lys Gln Leu Pro Ala Phe Ile Ser Glu Asp Ala Ser Gly Tyr Leu
                85                  90                  95

Thr Ser Ser Trp Leu Thr Leu Phe Val Pro Ser Val Tyr Thr Gly Val
                100                 105                 110

Phe Val Val Ser Leu Pro Leu Asn Ile Met Ala Ile Val Phe Ile
                115                 120                 125
```

| | | | | | | | | | | | | | |
|---|---|---|---|---|---|---|---|---|---|---|---|---|---|
| Leu | Lys<br>130 | Met | Lys | Val | Lys<br>135 | Lys | Pro | Ala | Val | Val<br>140 | Tyr | Met | Leu | His | Leu |
| Ala<br>145 | Thr | Ala | Asp | Val | Leu<br>150 | Phe | Val | Ser | Val | Leu<br>155 | Pro | Phe | Lys | Ile | Ser<br>160 |
| Tyr | Tyr | Phe | Ser | Gly<br>165 | Ser | Asp | Trp | Gln | Phe<br>170 | Gly | Ser | Glu | Leu | Cys<br>175 | Arg |
| Phe | Val | Thr | Ala<br>180 | Ala | Phe | Tyr | Cys | Asn<br>185 | Met | Tyr | Ala | Ser | Ile<br>190 | Leu | Leu |
| Met | Thr | Val<br>195 | Ile | Ser | Ile | Asp | Arg<br>200 | Phe | Leu | Ala | Val | Val<br>205 | Tyr | Pro | Met |
| Gln | Ser<br>210 | Leu | Ser | Trp | Arg | Thr<br>215 | Leu | Gly | Arg | Ala | Ser<br>220 | Phe | Thr | Cys | Leu |
| Ala<br>225 | Ile | Trp | Ala | Leu | Ala<br>230 | Ile | Ala | Gly | Val | Val<br>235 | Pro | Leu | Val | Leu | Lys<br>240 |
| Glu | Gln | Thr | Ile | Gln<br>245 | Val | Pro | Gly | Leu | Asn<br>250 | Ile | Thr | Thr | Cys | His<br>255 | Asp |
| Val | Leu | Asn | Glu<br>260 | Thr | Leu | Leu | Glu | Gly<br>265 | Tyr | Tyr | Ala | Tyr | Tyr<br>270 | Phe | Ser |
| Ala | Phe | Ser<br>275 | Ala | Val | Phe | Phe | Phe<br>280 | Val | Pro | Leu | Ile | Ile<br>285 | Ser | Thr | Val |
| Cys | Tyr<br>290 | Val | Ser | Ile | Ile | Arg<br>295 | Cys | Leu | Ser | Ser | Ser<br>300 | Ala | Val | Ala | Asn |
| Arg<br>305 | Ser | Lys | Lys | Ser | Arg<br>310 | Ala | Leu | Phe | Leu | Ser<br>315 | Ala | Ala | Val | Phe | Cys<br>320 |
| Ile | Phe | Ile | Ile | Cys<br>325 | Phe | Gly | Pro | Thr | Asn<br>330 | Val | Leu | Leu | Ile | Ala<br>335 | His |
| Tyr | Ser | Phe | Leu<br>340 | Ser | His | Thr | Ser | Thr<br>345 | Thr | Glu | Ala | Ala | Tyr<br>350 | Phe | Ala |
| Tyr | Leu | Leu<br>355 | Cys | Val | Cys | Val | Ser<br>360 | Ser | Ile | Ser | Ser | Cys<br>365 | Ile | Asp | Pro |
| Leu | Ile<br>370 | Tyr | Tyr | Tyr | Ala | Ser<br>375 | Ser | Glu | Cys | Gln | Arg<br>380 | Tyr | Val | Tyr | Ser |
| Ile<br>385 | Leu | Cys | Cys | Lys | Glu<br>390 | Ser | Ser | Asp | Pro | Ser<br>395 | Ser | Tyr | Asn | Ser | Ser<br>400 |
| Gly | Gln | Leu | Met | Ala<br>405 | Ser | Lys | Met | Asp | Thr<br>410 | Cys | Ser | Ser | Asn | Leu<br>415 | Asn |
| Asn | Ser | Ile | Tyr<br>420 | Lys | Lys | Leu | Leu | Thr<br>425 | | | | | | | |

( 2 ) INFORMATION FOR SEQ ID NO:221:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 18
        ( D ) OTHER INFORMATION: /note= "This position is -."

( i x ) FEATURE:
        ( A ) NAME/KEY: Modified-site
        ( B ) LOCATION: 21
        ( D ) OTHER INFORMATION: /note= "This position is -."

( i x ) FEATURE:
        ( A ) NAME/KEY: Modified-site
        ( B ) LOCATION: 22
        ( D ) OTHER INFORMATION: /note= "This position is -."

```
( i x ) FEATURE:
          ( A ) NAME/KEY: Modified-site
          ( B ) LOCATION: 30
          ( D ) OTHER INFORMATION: /note= "This position is -."

( i x ) FEATURE:
          ( A ) NAME/KEY: Modified-site
          ( B ) LOCATION: 31
          ( D ) OTHER INFORMATION: /note= "This position is -."

( x i ) SEQUENCE DESCRIPTION: SEQ ID NO:221:

Asn  Ala  Thr  Leu  Asp  Pro  Arg  Ser  Phe  Leu  Leu  Arg  Asn  Pro  Asn  Asp
1                  5                             10                            15

Lys  Xaa  Tyr  Glu  Xaa  Xaa  Pro  Phe  Trp  Glu  Asp  Glu  Glu  Xaa  Xaa  Lys
                20                           25                           30

Asn  Glu ( 2 ) INFORMATION FOR SEQ ID NO:222:

( i ) SEQUENCE CHARACTERISTICS:
            ( A ) LENGTH: 34 amino acids
            ( B ) TYPE: amino acid
            ( C ) STRANDEDNESS: single
            ( D ) TOPOLOGY: linear ( x i ) SEQUENCE DESCRIPTION: SEQ ID NO:222:

Asp  Ala  Thr  Val  Asn  Pro  Arg  Ser  Phe  Phe  Leu  Arg  Asn  Pro  Ser  Glu
1                  5                             10                            15

Asn  Thr  Phe  Glu  Leu  Val  Pro  Leu  Gly  Asp  Glu  Glu  Glu  Glu  Glu  Lys
                20                           25                           30

Asn  Glu ( 2 ) INFORMATION FOR SEQ ID NO:223:

( i ) SEQUENCE CHARACTERISTICS:
            ( A ) LENGTH: 13 amino acids
            ( B ) TYPE: amino acid
            ( C ) STRANDEDNESS: single
            ( D ) TOPOLOGY: linear ( i x ) FEATURE:
            ( A ) NAME/KEY: Modified-site
            ( B ) LOCATION: 7
            ( D ) OTHER INFORMATION: /note= "This position is -."

( i x ) FEATURE:
            ( A ) NAME/KEY: Modified-site
            ( B ) LOCATION: 8
            ( D ) OTHER INFORMATION: /note= "This position is -."

( x i ) SEQUENCE DESCRIPTION: SEQ ID NO:223:

Asp  Phe  Glu  Glu  Ile  Pro  Xaa  Xaa  Glu  Glu  Tyr  Leu  Gln
1                  5                             10
```